US009115355B2

(12) United States Patent
Han et al.

(10) Patent No.: US 9,115,355 B2
(45) Date of Patent: Aug. 25, 2015

(54) EXONUCLEASE RESISTANT POLYNUCLEOTIDE AND RELATED DUPLEX POLYNUCLEOTIDES, CONSTRUCTS, COMPOSITIONS, METHODS AND SYSTEMS

(71) Applicants: CALIFORNIA INSTITUTE OF TECHNOLOGY, Pasadena, CA (US); CITY OF HOPE, Duarte, CA (US)

(72) Inventors: Si-ping Han, Yorba Linda, CA (US); William A. Goddard, III, Pasadena, CA (US); Lisa Scherer, Monrovia, CA (US); John J. Rossi, Azusa, CA (US)

(73) Assignees: CALIFORNIA INSTITUTE OF TECHNOLOGY, Pasadena, CA (US); CITY OF HOPE, Duarte, CA (US)

( * ) Notice: Subject to any disclaimer, the term of this patent is extended or adjusted under 35 U.S.C. 154(b) by 0 days.

(21) Appl. No.: 14/093,387

(22) Filed: Nov. 29, 2013

(65) Prior Publication Data
US 2014/0329880 A1 Nov. 6, 2014

Related U.S. Application Data

(63) Continuation-in-part of application No. 13/848,687, filed on Mar. 21, 2013.

(60) Provisional application No. 61/731,420, filed on Nov. 29, 2012, provisional application No. 61/613,617, filed on Mar. 21, 2012.

(51) Int. Cl.
C12N 15/113 (2010.01)
C12N 15/11 (2006.01)

(52) U.S. Cl.
CPC ............ *C12N 15/113* (2013.01); *C12N 15/111* (2013.01); *C12N 2310/14* (2013.01); *C12N 2310/3519* (2013.01); *C12N 2320/32* (2013.01); *C12N 2320/51* (2013.01)

(58) Field of Classification Search
CPC . C12N 15/111; C12N 15/113; C12N 2310/14
See application file for complete search history.

(56) References Cited

U.S. PATENT DOCUMENTS

| 8,710,199 B2 | 4/2014 | Han et al. |
| 2006/0088864 A1 | 4/2006 | Smokle et al. |
| 2009/0082217 A1 | 3/2009 | Smokle et al. |
| 2009/0234109 A1 | 9/2009 | Han et al. |

FOREIGN PATENT DOCUMENTS

| WO | 2007/107162 | 9/2007 |
| WO | 2011/163526 | 12/2011 |

OTHER PUBLICATIONS

Lee, H. et al. *Molecular Dynamics Studies of Polyethylene Oxide and Polyethylene Glycol: Hydrodynamic Radius and Shape Anisotropy.* Biophysical Journal, vol. 95, Aug. 2008, pp. 1590-1599.

Yurke, B. et al. *A DNA-fuelled molecular machine made of DNA.* Nature, vol. 406, Aug. 10, 2000, pp. 605-608.
IDT-Integrated DNA Technologies. *OligoAnalyzer 3.1.* Web. Retrieved from <http://www.idtdna.com/calc/analyzer> on Nov. 19, 2014.
NUPACK—Nucleic Acid Package. Web. Retrieved from <http://www.nupack.org> on Nov. 19, 2014.
GeneLink. *Gene Assays & SPCT.* Web. Retrieved from <http://genelink.com> on Nov. 19, 2014.
Restriction Requirement issued for U.S. Appl. No. 13/848,687, filed Mar. 21, 2013 in the name of California Institute of Technology et al. mail date: Nov. 7, 2014.
Restriction Requirement issued for U.S. Appl. No. 11/978,219, filed Oct. 26, 2007 in the name of Si-ping Han et al. mail date: Jun. 4, 2014.
Non-Final Office Action issued for U.S. Appl. No. 11/978,219, filed Oct. 26, 2007 in the name of Si-ping Han et al. mail date: Sep. 30, 2014.
Patterning Definition. Retrieved on Dec. 5, 2014 from the internet: <https://www.google.com/search?q=patterning+definition&spell=1>.
Song, J.H., et al., *Crystal Overgrowth on Gold Nanorods: Tuning the Shape, Facet, Aspect Ratio, and Composition of the Nanorods.* Chem. Eur. J. vol. 11, pp. 910-916. 2005.
Wang, J., et al. *Silver Enhanced Colloidal Gold Electrochemical Stripping Detection of DNA Hybridization.* Langmuir, vol. 17, pp. 5739-5741. 2001.
Gu, Q. et al. *DNA nanowire fabrication.* Nanotechnology, vol. 17, R14-R25. 2006.
Foultier, B., et al. *Comparison of DNA detection methods using nanoparticles and silver enhancement.* IEE Proc.-Nanobiotechnolo., vol. 152(1), pp. 3-12. 2005.
Barish, R.D. et al. *An information-bearing seed for nucleating algorithmic self-assembly.* PNAS, 106, pp. 6054-6059. 2009.
Fu, T.J., et al. *DNA Double-Crossover Molecules.* Biochemistry, 32, pp. 3211-3220. 1993.
Winfree, E., et al. *Design and self-assembly of two-dimensional DNA crystals.* Nature, vol. 394, pp. 539-544. 1998.
Zhang, Y., et al. *Construction of a DNA-Truncated Octahedron.* J. Am. Chem. Soc., vol. 116, pp. 1661-1669. 1994.
Chen, J., et al. *Synthesis from DNA of a molecule with the connectivity of a cube.* Nature, vol. 350, pp. 631-633. Apr. 1991.
Rothemund, P.W.K. *Folding DNA to create nanoscale shapes and patterns.* Nature, vol. 440, pp. 297-302. 2006.
Rothemund, P.W.K. et al. *Algorithmic Self-Assembly of DNA Sierpinski Triangles.* PLoS Biology 2(12), e424, pp. 2041-2053. 2004.
Barish, R.D., et al. *Two Computational Primitives for Algorithmic Self-Assembly: Copying and Counting.* Nano Letters, vol. 5(12), pp. 2586-2592. 2005.

(Continued)

*Primary Examiner* — J. E. Angell
(74) *Attorney, Agent, or Firm* — Steinfl & Bruno LLP

(57) ABSTRACT

Provided herein are exonuclease resistant polynucleotides and related constructs, compositions, methods and systems.

26 Claims, 18 Drawing Sheets

(56) References Cited

OTHER PUBLICATIONS

Yan, H., et al. *Directed nucleation assembly of DNA tile complexes for barcode-patterned lattices.* Proc. Natl. Acad. Sci., vol. 100(14), pp. 8103-8108. 2003.
Schulman, R. et al. *Programmable Control of Nucleation for Algorithmic Self-assembly.* DNA Computing 10. Springer-Verlag: Berlin, Heidelberg, pp. 319-328. 2005.
Winfree-E. *Self-healing Tile Sets*, In Nanotechnology: Science and Computation, pp. 55-78. 2006.
*Undecagold.* Nanoprobes. Revised 1.1. 2 pgs. Mar. 2000.
*Goldenhance.* Nanoprobes. Revised 1.5. 3 pgs. Oct. 2013.
Wu, H., et al., "Properties of cloned and expressed human RNase H1," *The Journal of Biological Chemistry*, 1999, vol. 274, pp. 28270-28278.
Zamaratski, E., et al., "A critical survey of the structure-function of the antisense oligo/RNA heteroduplex as substrate for RNase H," *Journal of Biochemical and Biophysical Methods*, 2001, vol. 48, pp. 189-208.
Cazenave, C., et al., "Characterization and subcellular localization of ribonuclease Activities From Xenopus laevia oocytes," *The Journal of Biological Chemistry*, 1994, vol. 269, pp. 25185-25192.
Nowotny, M., et al. Crystal structures of RNase H bound to an RNA/DNA hybrid: substrate specificity and metal-dependent catalysis, *Cell*, 2005, vol. 121, pp. 1005-1016.
Song, J. J. et al., "The crystal structure of the Argonaute2 PAZ domain reveals an RNA binding motif in RNAi effector complexes", *Nature Structural Biology*, vol. 10, pp. 1026-1032 (2003).
Ma, J. B. et al., "Structural basis for overhang-specific small interfering RNA recognition by the PAZ domain", *Nature*, vol. 429, pp. 318-322 (2004).
Yan, K. S. et al., "Structure and conserved RNA binding of the PAZ domain", *Nature*, vol. 426, pp. 468-265 (2003).
Lingel, A. et al., "Structure and nucleic-acid binding of the Drosophila Argonaute 2 PAZ domain", *Nature*, vol. 426, pp. 465-469 (2003).
Behlke, M. A. et al., "Chemical modification of siRNAs for in vivo use", *Oligonucleotides*, vol. 18, pp. 305-320 (2008).
Rose, S. D. et al., "Functional polarity is introduced by Dicer processing of short substrate RNAs", *Nucleic Acids Research*, vol. 33, pp. 4140-4156 (2005).
Tomari, Y., et al., "A Protein Sensor for siRNA Asymmetry", *Science*, vol. 306, pp. 1377-1380, (2004).
Susan M. Freier and Karl-Heinz Altman, "The ups and downs of nucleic acid duplex stability: structure-stability studies on chemically-modified DNA:RNA duplexes," *Nucleic Acids Research*, 1997, vol. 25, No. 22 4429-4443.
Majlessi, M. et al. "Advantages of 2'-O-methyl oligoribonucleotide probes for detecting RNA targets," *Nucleic Acids Research*, 1998, vol. 26, No. 9, pp. 2224-2229.
Kierzek, E. et al. "The influence of locked nucleic acid residues on the thermodynamic properties of 2'-O-methyl RNA/RNA heteroduplexes," *Nucleic Acids Research*, 2005, vol. 33, No. 16, pp. 5082-5093.
Yakovchuk, P. et al. "Base-stacking and base-pairing contributions into thermal stability of the DNA double helix *Nucleic Acids Research*," 2006, vol. 34, No. 2, pp. 564-574.
Han, H. et al. "Sequence-specific recognition of double helical RNA and RNA.DNA by triple helix formation," *PNAS* May 1, 1993 vol. 90, pp. 3806-3810.
Burge S, Parkinson GN, Hazel P, Todd AK, Neidle S (2006). "Quadruplex DNA: sequence, topology and structure". *NAR* 34 (19): 5402-5415. doi:10.1093/nar/gkl655.
J.N. Zadeh, C.D. Steenberg, J.S. Bois, B.R. Wolfe, M.B. Pierce, A.R. Khan, R.M. Dirks, N.A. Pierce. "NUPACK: analysis and design of nucleic acid systems." *J Comput Chem*, 32, 170-173, 2011.
R.M. Dirks, J.S. Bois, J.M. Schaeffer, E. Winfree, and N.A. Pierce. (2007) "Thermodynamic analysis of interacting nucleic acid strands." *SIAM Rev*, 49, 65-88.
R.M. Dirks and N.A. Pierce. (2003) "A partition function algorithm for nucleic acid secondary structure including pseudoknots." *J Comput Chem*, 24, 1664-1677.
R.M. Dirks and N.A. Pierce. (2004) "An algorithm for computing nucleic acid base-pairing probabilities including pseudoknots." *J Comput Chem*, 25, 1295-1304.
J.N. Zadeh, B.R. Wolfe, N.A. Pierce. "Nucleic acid sequence design via efficient ensemble defect optimization." *J Comput Chem*, 32, 439-452, 2011.
M. Zuker. "Mfold web server for nucleic acid folding and hybridization prediction." *Nucleic Acids Res*. 31 (13), 3406-3415, 2003.
Waugh, P. Gendron, R. Altman, J. W. Brown, D. Case, D. Gautheret, S. C. Harvey, N. Leontis, J. Westbrook, E. Westhof, M. Zuker & F. Major." RNAML: A standard syntax for exchanging RNA information." *RNA* 8 (6), 707-717, 2002.
M. Zuker & A. B. Jacobson. "Using Reliability Information to Annotate RNA Secondary Structures." *RNA* 4, 669-679, 1998. [Abstract][Preprint] Note: Explains color annotation of secondary structure.
N. R. Markham & M. Zuker. "UNAFold: Software for Nucleic Acid Folding and Hybridization. In Data, Sequence Analysis, and Evolution," J. Keith, ed., *Bioinformatics*: vol. 2, Chapter 1, pp. 1-33, Humana Press Inc., 2008.
M. Zuker, D. H. Mathews & D. H. Turner. "Algorithms and Thermodynamics for RNA Secondary Structure Prediction: A Practical Guide in RNA Biochemistry and Biotechnology,"pp. 1-23, J. Barciszewski and B. F. C. Clark, eds. , NATO ASI Series, Kluwer Academic Publishers, Dordrecht, NL, 1999.
M. Zuker. "Prediction of RNA Secondary Structure by Energy Minimization. In Computer Analysis of Sequence Data" A. M. Griffin and H. G. Griffin eds. Methods in Molecular Biology, Humana Press Inc. , 267-294, 1994.
J. A. Jaeger, D. H. Turner & M. Zuker. "Predicting Optimal and Suboptimal Secondary Structure for RNA." In Molecular Evolution: Computer Analysis of Protein and Nucleic Acid Sequences, R. F. Doolittle ed. Methods in Enzymology 183, 281-306, 1990.
M. Zuker. "On Finding All Suboptimal Foldings of an RNA Molecule." *Science* 244, 48-52, 1989.
D. H. Mathews, J. Sabina, M. Zuker & D. H. Turner. "Expanded Sequence Dependence of Thermodynamic Parameters Improves Prediction of RNA Secondary Structure," J. Mol. Biol. 288, 911-940, 1999.
E. Walter, D. H. Turner, J. Kim, M. H. Lyttle, P. Müller, D. H. Mathews & M. Zuker. "Coaxial stacking of helixes enhances binding of oligoribonucleotides and improves predictions of RNA folding." *Proc. Natl. Acad. Sci. USA* 91, 9218-9222, 1994.
Mathews, D. H. et al. "RNA Secondary Structure Prediction." *In Current Protocols in Nucleic Acid Chemistry* S. Beaucage, D. E. Bergstrom, G. D. Glick, and R. A. Jones eds., John Wiley & Sons, New York, 11. 2. 1-11. 2. 10, (2007) DOI: 10.1002/0471142700. nc1102s28.
D. H. Mathews, S. J. Schroeder, D. H. Turner & M. Zuker. "Predicting RNA Secondary Structure." In the RNA World, R. F. Gesteland, T. R. Cech and J. F. Atkins eds., 3rd edition, Cold Spring Harbor Laboratory Press, Cold Spring Harbor, New York, Chapter 22, 631-657, 2006.
D. H. Mathews & M. Zuker."Predictive Methods Using RNA Sequences." In Bioinformatics: A Practical Guide to the Analysis of Genes and Proteins, A. Baxevanis and F. Ouellette eds. ,3rd edition, John Wiley & Sons, New York, Chapter 6, 143-164, 2005.
D. H. Mathews, M. D. Disney, J. L. Childs, S. J. Schroeder, M. Zuker & D. H. Turner."Incorporating chemical modification constraints into a dynamic programming algorithm for prediction of RNA secondary structure." Proc. Natl. Acad. Sci. USA 101 (19), 7287-7292, 2004.
M. Zuker & D. Sankoff."RNA Secondary Structures and their Prediction." Bull. Mathematical Biology 46, 591-621, 1984.
M. Zuker & P. Stiegler. "Optimal computer folding of large RNA sequences using thermodynamics and auxiliary information." *Nucleic Acids Res*. 9, 133-148, 1981.
J. -M. Rouillard, M. Zuker & E. Gulari. "OligoArray 2. 0: design of oligonucleotide probes for DNA microarrays using a thermodynamic approach." *Nucleic Acids Res*. 31 (12), 3057-3062, 2003.

(56) References Cited

OTHER PUBLICATIONS

J. -M. Rouillard, C. J. Herbert & M. Zuker. "OligoArray: Genome-scale oligonucleotide design for microarrays." *Bioinformatics* 18 (3), 486-487, 2002.
Ding, Y. et al. "RNA secondary structure prediction by centroids in a Boltzmann weighted ensemble," *RNA* 2005. 11: pp. 1157-1166.
Braasch, D.A. et al. "RNA Interference in Mammalian Cells by Chemically-Modified RNA," *Biochemistry* 2003,42, pp. 7967-7975.
Jin-Biao Ma, Keqiong Ye & Dinshaw J. Patel"Structural basis for overhang specific small interfering RNA recognition by the PAZ domain," *Nature*, 429, 318-322 (2004).
Whitehead, K.A. et al. Nature Reviews Drug Discovery 8, 129-138 (Feb. 2009) | doi:10.1038/nrd2742, "Knocking down barriers: advances in siRNA delivery".
Simeoni, F. "Insight into the mechanism of the peptide.based gene delivery system MPG: implications for delivery of siRNA into mammalian cells." *Nucleic acids research* 31.11 (2003):2717-2724.
Liu, Z., Winters, M., Holodniy, M. and Dai, H. (2007), "siRNA Delivery into Human T Cells and Primary Cells with Carbon-Nanotube Transporters." *Angewandte Chemie*, 119: 2069-2073. doi: 10.1002/ange.200604295.
Chu, T.C. et al. "Aptamer mediated siRNA delivery," *Nucl. Acids Res.* 34(10): e73 doi:10.1093/nar/gkl388, 2006.
Rozema, D.B. et al. "Dynamic PolyConjugates for targeted in vivo delivery of siRNA to hepatocytes," *PNAS* 2007 104 (32) 12982-12987.
Derfus, A.M. et al. "Targeted Quantum Dot Conjugates for siRNA Delivery," *Bioconjugate Chem.*, 2007, 18 (5), pp. 1391-1396, DOI: 10.1021/bc060367e.
Kumar, P. et al. "T Cell-Specific siRNA Delivery Suppresses HIV-1 Infection in Humanized Mice," *Cell*, vol. 134, Issue 4, Aug. 22, 2008, pp. 577-586.
Rinaudo, K. et al. "A universal RNAi-based logic evaluator that operates in mammalian cells," *Nature Biotechnology* 25, 795-801 (2007).
Ehsani, A. et al. "Rational Design of Micro-RNA-like Bifunctional siRNAs Targeting HIV and the HIV Coreceptor CCR5" *Molecular Therapy* (2010) 18:4, pp. 796-802. doi:10.1038/mt.2009.321.
Tiemann, K. et al."Dual-targeting siRNAs" *RNA* (2010), 16: pp. 1275-1284.
Judge, A.D. et al. "Design of Noninflammatory Synthetic siRNA Mediating Potent Gene Silencing in Vivo," *Molecular Therapy* (2006) 13, pp. 494-505.
Blight K.J. et al., "Secondary Structure Determination of the Conserved 98-Base Sequence at the 3' Terminus of Hepatitis C Virus Genome RNA" Journal of Virology, Oct. 1997, vol. 71, pp. 7345-7352.
Ehsani, A. et al. "Rational Design of Micro-RNA-like Bifunctional siRNAs Targeting HIV and the HIV Coreceptor CCR5," Molecular Therapy (2010) 18;3, pp. 796-802. doi;10.138/mt.2009.321.
PCT International Search Report mailed on Feb. 24, 2012 for PCT Application No. PCT/US2011/041703 filed Jun. 23, 2011 in the name of California Institute of Technology et al.
PCT Written Opinion completed on Feb. 24, 2012 for PCT Application No. PCT/US2011/041703 filed Jun. 23, 2011 in the name of California Institute of Technology et al.
Li, J. et al., "Enzymatic signal amplification of molecular beacons for sensitive DNA detection," Nucleic Acid Research 2008, 36: 1-17.
Weissleder, R., et al "In vivo imaging of tumors with protease-activated near-infrared fluorescent probes," Nature Biotechnology 1999, 17: 375-378.
PCT International Search Report mailed on Jul. 9, 2013 for PCT Application No. PCT/US2013/033380 filed Mar. 21, 2013 in the name of California Institute of Technology et al.
PCT Written Opinion mailed on Jul. 9, 2013 for PCT Application No. PCT/US2013/033380 filed Mar. 21, 2013 in the name of California Institute of Technology et al.
De Paula, D. et al. "Hydrophobization and bioconjugation for enhanced siRNA delivery and targeting." RNA, vol. 13, pp. 431-456, 2007.
Kim, J. et al. "Intracellular small interfering RNA delivery using genetically engineered double-stranded RNA binding protein domain." The Journal of Gene Medicine. vol. 11, pp. 804-812, 2009.
Wang, H.W. et al. "Structural Insights into RNA Processing by the Human RISC-Loading Complex." Nat Struct Mol Biol., vol. 16(1), pp. 1148-1153, 2009.
Mathews, D.H. et al. "Folding and Finding RNA Secondary Structure." Cold Spring Harbor Perspectives in Biology. 2010.
Restriction Requirement issued for U.S. Appl. No. 13/167,672, filed Jun. 23, 2011 filed in the name of Si-Ping Han mailed on Dec. 14, 2012.
Non-Final Office Action issued for U.S. Appl. No. 13/167,672, filed Jun. 23, 2011 filed in the name of Si-Ping Han mailed on Apr. 1, 2013.
Notice of Allowance issued for U.S. Appl. No. 13/167,672, filed Jun. 23, 2011 filed in the name of Si-Ping Han mailed on Dec. 12, 2013.
Matsukura, M. et al. "Phosphorothioate analogs of oligodeoxynucleotides: inhibitors of replication and cytopathic effects of human immunodeficiency virus." *Proceedings of the National Academy of Sciences* 84, 7706-7710 1987.
Collingwood, M., et al. "Chemical Modification Patterns Compatible with High Potency Dicer-Substrate Small Interfering RNAs." *Oligonucleotides* 18, 187-200 2008.
Lennox, K. A., et al. "Improved Performance of Anti-miRNA Oligonucleotides Using a Novel Non-Nucleotide Modifier." *Mol Ther Nucleic Acids* 2, e117, doi:10.1038/mtna.2013.46 2013.
Bramsen, J. B., et al. "A large-scale chemical modification screen identifies design rules to generate siRNAs with high activity, high stability and low toxicity." *Nucleic Acids Research* 37, 1-15, doi:10.1093/nar/gkp106 2009.
Mathy, N., et al. "5'-to-3' Exoribonuclease Activity in Bacteria: Role of RNase J1 in rRNA Maturation and 5' Stability of mRNA." *Cell* 129, 681-692 2007.
Yang X. et al. "Studies of the 5' Exonuclease and Endonuclease Activities of CPSF-73 in Histone Pre-mRNA Processing." *Molecular and Cellular Biology* 29, 31-42, doi:10.1128/mcb.00776-08 2009.
Efthymiou, T. C. et al "Evaluation of siRNAs that contain internal variable-length spacer linkages." *Bioorganic & Medicinal Chemistry Letters* 22, 5590-5594, doi:http://dx.doi.org/10.1016/j.bmcl.2012.07.006 2012.
Zhou, J., et al. Selection, characterization and application of new RNA HIV gp 120 aptamers for facile delivery of Dicer substrate siRNAs into HIV infected cells. *Nucleic Acids Research* 37, 3094-3109, doi:10.1093/nar/gkp185 2009.
Non-Final Office Action issued for U.S. Appl. No. 13/848,687, filed Mar. 21, 2013 in the name of Si-ping Han et al. mailed on Mar. 9, 2015.
Exiqon. *LNA$^{TM}$ Oligo Tools and Design Guidelines*. Web. Retrieved from <https://www.exiqon.com/oligo-tools> on Mar. 16, 2015.
"Worm-like Chain." Wikipedia: The Free Encyclopedia. Wikimedia Foundation, Inc. Web. Retrieved from < http://en.wikipedia.org/wiki/Worm-like_chain> on Mar. 26, 2015.
"Int Cy5$^{TM}$." IDT—Integrated DNA Technologies. Web. Retrieved from <http://www.idtdna.com/site/Catalog/Modifications/Product/1476> on Mar. 26, 2015.
"The mfold Web Server." The RNA Institute College of Arts and Sciences. Web. Retrieved from <http://mfold.rna.albany.edu/?q=mfold> on Mar. 26, 2015.
"Sfold." Software for Statistical Folding of Nucleic Acids and Studies of Regulatory RNAs. Web. Retrieved from <http://sfold.wadsworth.org/cgi-bin/index.pl> on Mar. 26, 2015.
Diao, J.J. et al. "Self assembled nanoparticle wires by discontinuous vertical colloidal deposition." Applied Physics Letters, vol. 87, 103113, pp. 1-3 (2005).
"Divalent." Wikipedia: The Free Encyclopedia. Wikimedia Foundation, Inc. Web. Retrieved from <http://en.wikipedia.org/wiki/Divalent> on Mar. 16, 2015.
Northern, D.B.L. et al. "Atomic Force Microscopy of Mica Surface After Ion Replacement." Proceedings of the 49$^{th}$ Annual Meeting of the Electron Microscopy Society of America. San Francisco Press, Inc.: San Francisco. 1991.
Scheibel, T. et al. "Conducting nanowires built by controlled self-assembly of amyloid fibers and selective metal deposition." PNAS, vol. 100(8), pp. 4527-4532. 2003.

(56) References Cited

OTHER PUBLICATIONS

Seeman, N.C. "DNA in a material world." Nature, vol. 421, pp. 427-431. 2003.
Rothemund, P.W.K. "Folding DNA to create nanoscale shapes and patterns." Nature, vol. 440, pp. 297-302. 2006.
Castello, A. et al. "Insights into RNA Biology from an Atlas of Mammalian mRNA-Binding Proteins." Cell, vol. 149, pp. 1393-1406. 2012.
Chen, H. et al. "Ionic strength-dependent persistence lengths of single-stranded RNA and DNA." PNAS, vol. 109(3), pp. 799-804. 2012.
Delebecque, C.J. et al. "Organization of Intracellular Reactions with Rationally Designed RNA Assemblies." Science, vol. 333, pp. 470-474. 2011.
Delebecque, C.J. et al. "Supporting Online Material for Organization of Intracellular Reactions with Rationally Designed RNA Assemblies." Science, vol. 333, S1-S27. 2011.
Ding, Y. et al. "Sfold web server for statistical folding and rational design of nucleic acids." Nucleic Acids Research, vol. 32, W135-W141. 2004.
Geary, C. et al. "A single-stranded architecture for cotranscriptional folding of RNA nanostructures." Science, vol. 345, pp. 799-804. 2014.
Gohlke, C. et al. "Kinking of DNA and RNA helices by bulged nucleotides observed by fluorescence resonance energy transfer." Proc. Natl. Acad. Sci., vol. 91, pp. 11660-11664. 1994.
Hochrein, L.M. et al. Conditional Dicer Substrate Formation via Shape and Sequence Transduction with Small Conditional RNAs. Journal of the American Chemical Society, vol. 135, pp. 17322-17330. 2013.
Kahan, M. et al. "Towards molecular computers that operate in a biological environment." Physica D, vol. 237, pp. 1165-1172. 2008.
Kertesz, M. et al. "Genome-wide Measurement of RNA Secondary Structure in Yeast." Nature, vol. 467, pp. 103-107. 2010.
Lu, J. et al. "Iron-binding activity of human iron-sulfur cluster assembly protein hIscA1." Biochem. vol. 428, pp. 125-131. 2010.
Mizukoshi, T. et al. "Structural study of DNA duplexes containing the (6-4) photoproduct by fluorescence resonance of transfer." Nucleic Acids Research, vol. 29(24), pp. 4948-4954. 2001.
Pettersen, E.F. et al. "UCSF Chimera—A Visualization System for Exploratory Research and Analysis." J. Comput. Chem, vol. 25, pp. 1605-1612. 2004.
Rapaport, D.C. "The art of molecular dynamics simulation." Cambridge University Press. 2004. 13 pgs.
Scherer, L.J. "Optimization and characterization of tRNA-shRNA expression constructs." Nucleic Acids Research, vol. 35(8), pp. 2620-2628. 2007.
Srinivas, N. et al. "On the biophysics and kinetics of toehold-mediated DNA strand displacement." Nucleic Acids Research, vol. 41(22), pp. 10641-10658. 2013.
Tan, R. et al. "Structural variety of arginine-rich RNA-binding peptides." Proc. Natl. Acad. Sci. vol. 92, pp. 5282-5286. 1995.
Watts, J.M. et al. "Architecture and Secondary Structure of an Entire HIV-1 RNA Genome." Nature, vol. 460, pp. 711-716. 2009.
Zhang, D. Y. et al. "Dynamic DNA nanotechnology using strand-displacement reactions." Nature, vol. 3, pp. 103-113. 2011.
Zhang, F. et al. "Structureal DNA Nanotechnology: State of the Art and Future Perspective." Journal of the American Chemical Society, vol. 136, pp. 11198-11211. 2014.
Dreyfuss, G., et al. "Messenger-RNA-binding proteins and the messages they carry." Nat. Rev. Mol. Cell Biol., vol. 3, pp. 195-205. 2002.
Yusupov, M. M., et al. "Crystal structure of the ribosome at 5.5 A resolution." Science, vol. 292, pp. 883-896. 2001.
Douglas, S. M., et al. "A Logic-Gated Nanorobot for Targeted Transport of Molecular Payloads." Science, vol. 335, pp. 831-834. 2012.
Green, L. S., et al. "Inhibitory DNA Ligands to Platelet-Derived Growth Factor B-Chain." *Biochemistry* vol. 35, pp. 14413-14424, (1996).
Kienberger, F., et al. "Static and Dynamical Properties of Single Poly(Ethylene Glycol) Molecules Investigated by Force Spectrocopy." Single Molecules, vol. 1, pp. 123-128. 2000.
Lilley, D. M. et al. "Fluorescence resonance energy transfer as a structural tool for nucleic acids." Current Opinion in Chemical Biology, vol. 4, pp. 507-517. 2000.
Fürtig, B., et al. "Time-Resolved NMR Studies of RNA Folding." Biopolymers, vol. 86, pp. 360-383. 2007.
Varani, G., et al. NMR Investigation of RNA structure. Progress in Nuclear Magnetic Resonance Spectroscopy, vol. 29, pp. 51-127. 1996.
Russell, R. et al. "Small angle X-ray scattering reveals a compact intermediate in RNA folding." Nat Struct Mol Biol, vol. 7, pp. 367-370. 2000.
Lipfert, J. et al. "Small-Angle X-Ray Scattering from RNA, Proteins, and Protein Complexes." Annual Review of Biophysics and Biomolecular Structure. vol. 36, 307-327. 2007.
Takada, S. "Coarse-grained molecular simulations of large biomolecules." Current Opinion in Structural Biology, vol. 22, pp. 130-137. 2012.
Pascal, T. A., et al. "Role of Specific Cations and Water Entropy on the Stability of Branched DNA Motif Structures." The Journal of Physical Chemistry B, vol. 116, pp. 12159-12167. 2012.
Sim, A. Y. L., et al. "Modeling nucleic acids." Current Opinion in Structural Biology, vol. 22, pp. 273-278. 2012.
Dragan, A. I. Use of Fluorescence Resonance Energy Transfer (FRET) in Studying Protein-Induced DNA Bending. Methods in Enzymology. vol. 450 (Eds Brand Ludwig & L. Johnson Michael), Chapter 9, pp. 185-199. Academic Press. 2008.
Bassi, G.S. et al. "Ion-Induced folding of the hammerhead ribozyme: a fluorescence resonance energy transfer study." The EMBO Journal, vol. 16, pp. 7481-7489. 1997.
Houseley, J., et al. RNA-quality control by the exosome. Nat Rev Mol Cell Biol, vol. 7, pp. 529-539 2006.
Tinland, B. et al. "Persistence Length of Single-Stranded DNA." Macromolecules, vol. 30, pp. 5763-5765. 1997.
Restriction Requirement issued for U.S. Appl. No. 11/978,219, filed Oct. 26, 2007 filed in the name of Si-Ping Han et al. Mailed on Jun. 4, 2014.
Non-Final Office Action issued for U.S. Appl. No. 11/978,219, filed Oct. 26, 2007 filed in the name of Si-Ping Han et al. Mailed on Sep. 30, 2014.

EXONUCLEASE RESISTANT POLYNUCLEOTIDE AND RELATED DUPLEX POLYNUCLEOTIDES, CONSTRUCTS, COMPOSITIONS, METHODS AND SYSTEMS

CROSS REFERENCE TO RELATED APPLICATIONS

This application is a continuation in part of U.S. application Ser. No. 13/848,687 entitled "Targeting Domain And Related Signal Activated Molecular Delivery" filed on Mar. 21, 2013, which claims priority to U.S. Provisional Application entitled "Pseudoknot construct for signal activated RNA interference" Ser. No. 61/613,617, filed on Mar. 21, 2012, the disclosure of which is incorporated herein by reference in its entirety. The Application is also related to U.S. Provisional Application entitled "Controlled Release Of Therapeutic Cargo By Exonucleases" Ser. No. 61/731,420, filed on Nov. 29, 2012, the disclosure of which is incorporated herein by reference in its entirety. The present application might also be related to US application entitled "Signal Activated Molecular Delivery" Ser. No. 13/167,672 filed on Jun. 23, 2011, and to International Application "Signal Activated Molecular Delivery" Serial No. PCT/US11/41703 filed on Jun. 23, 2011, the disclosure of each of which is also incorporated by reference in its entirety.

FIELD

The present disclosure relates to exonuclease resistant polynucleotide and related duplex polynucleotides, constructs, compositions, methods and systems.

BACKGROUND

Exonucleases are enzymes that work by cleaving nucleotides one at a time from the end (exo) of a polynucleotide chain. For example, eukaryotes and prokaryotes have three types of exonucleases involved in the normal turnover of mRNA.

Various applications in which polynucleotides can be desirably protected in environments where exonucleases are present (e.g. a cell environment) are known in the field of biology and in particular, in the field of biological molecule analysis.

In particular, protection of polynucleotides from exonucleases can be desired in applications aimed at obtaining controlled delivery of analytes of interest to specific environments. Whether for medical applications or for fundamental biology studies, several methods are commonly used for the delivery of various classes of biomaterials and biomolecules which involve delivery of one or more polynucleotides in cell environments or other environments where exonucleases are present.

For example, protection of polynucleotide in specific environments where exonucleases are present, e.g. specific cell types and/or tissues of individuals in vitro and/or in vivo is currently still challenging, especially when directed at providing controlled release of the polynucleotides in a controllable conformation, typically associated to a biological activity.

SUMMARY

Provided herein, are exonuclease resistant polynucleotides and related duplex polynucleotides, constructs, compositions, methods and systems.

According to a first aspect, an exonuclease resistant polynucleotide is described. The exonuclease resistant polynucleotide has a 5' end and a 3' end and comprises a blocker domain having a non-nucleic acid polymer segment and a phosphorothioate segment. The non-nucleic acid polymer segment comprises a non-nucleic acid linear polymer having a first end and a second end. In the exonuclease resistant polynucleotide, the non-nucleic acid linear polymer has two to six residues linked one linked to another by a residue-to-residue bond with an end to end distance for the non-nucleic acid linear polymer in a fully extended conformation of up to about 1 nm. In the exonuclease resistant polynucleotide, the non-nucleic acid linear polymer has a persistence length up to about 0.5 nm. The phosphorothioate segment comprises one to five nucleotides linked by phosphorothioate linkages to form a phosphorothioate sequence having a 5' and a 3' end, and attaching at the 5' end of the phosphorothioate sequence the first end of the non-nucleic acid linear polymer through a phosphodiester linkage, the second end of the non-nucleic acid linear polymer presented at the 5' end of the exonuclease resistant polynucleotide.

According to a second aspect, an exonuclease resistant duplex polynucleotide is described. The duplex polynucleotide comprises a duplex RNA having a length of about 17 to about 30 bp and comprising a guide strand complementary bound to a passenger strand, each of the guide strand and passenger strand having a 5' end and a 3' end, the duplex RNA having at least one configuration allowing processing of the guide strand by dicer and/or an argonaute enzyme, the passenger strand comprising the exonuclease resistant polynucleotide herein described, in a configuration in which the second end of non-nucleic acid polymer is presented at the 5' end of the passenger strand. In some embodiments, the exonuclease resistant duplex polynucleotide is a targeting domain.

According to a third aspect, a molecular construct is described, the molecular construct comprising the exonuclease resistant duplex polynucleotide herein described attached to at least one vehicle moiety, the molecular construct having at least one configuration in which the 5' passenger strand of the exonuclease resistant duplex polynucleotide is presented for binding to an exonuclease.

According to a fourth aspect a method and system to provide exonuclease resistant polynucleotide is described, the method comprising providing a polynucleotide comprising a blocker domain having a non-nucleic acid polymer segment and a phosphorothioate segment. In the method, the non-nucleic acid polymer segment comprises a linear polymer having a first end and a second end. The phosphorothioate segment comprises at least three nucleotides linked by phosphorothioate linkages to form a phosphorothioate sequence having a 5' and a 3' end, and attaching at the 5' end of the phosphorothioate sequence, the first end of the non-nucleic acid polymer segment through a phosphodiester linkage. In the method, the providing is performed to have the second end of the non-nucleic acid polymer segment presented at the 5' end of the resulting exonuclease resistant polynucleotide.

According to a fifth aspect, a method and system to provide an exonuclease resistant duplex polynucleotide is described, the method comprising providing a duplex polynucleotide comprising an exonuclease resistant polynucleotide herein described. In the method, the duplex polynucleotide has a length of about 19 to about 30 bp and comprising a guide strand complementary bound to a passenger strand, each of the guide strand and passenger strand having a 5' end and a 3' end, the duplex RNA being in a configuration allowing processing of the guide strand by dicer and/or an argonaute enzyme. In the method the providing is performed to have the second end of non-nucleic acid polymer presented at the 5' end of the passenger strand.

According to a sixth aspect a method and system to provide a molecular construct having an exonuclease resistant moiety are described. The method comprises, providing an exonuclease resistant duplex polynucleotide herein described attaching at least one additional moiety in at least one configuration of the exonuclease resistant molecular construct in which the 5' passenger strand of the exonuclease resistant duplex polynucleotide is presented for binding to an exonuclease.

According to a seventh aspect, a composition is described, the composition comprising one or more exonuclease resistant polynucleotide, one or more exonuclease resistant duplex polynucleotide and/or an exonuclease resistant molecular construct herein described together with a suitable vehicle.

The exonuclease resistant polynucleotides, duplexes, constructs, systems, compositions and methods herein described, allow in several embodiments to control and in particular minimize polynucleotide degradation due to exonuclease enzymatic reaction while maintaining a duplex RNA configuration processable by Dicer and/or Argonaute.

The exonuclease resistant polynucleotides, duplexes, constructs, systems, compositions and methods herein described can be used in connection with applications wherein control and in particular, minimization of polynucleotide degradation due to exonuclease enzymatic reaction is desired in particular when the polynucleotide comprises a dicer and/or argonaute processable duplex RNA. Exemplary applications include but are not limited to medical applications, biological analysis, research and diagnostics including but not limited to clinical, therapeutic and pharmaceutical applications, such as cell type specific drug delivery, cell type specific modeling or therapy, including but not limited to gene therapy and RNAi.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 1A shows a schematic of binding of the RNA duplex by Dicer. FIG. 1B, shows a schematic representation of the product resulting from correct Dicer processing of the exemplary RNA duplex shown.

FIG. 3A shows a schematic representation of an exemplary duplex polynucleotide comprising an exemplary exonuclease resistant polynucleotide (indicated as B7) having an unmodified 5' overhang domain comprising only RNA bases and phosphodiester backbone connections. FIG. 3B shows a schematic representation of an exemplary duplex polynucleotide comprising an exemplary exonuclease resistant polynucleotide (indicated as B10) comprising RNA residues connected by phosphorothioate linkage and having a 5' terminal hexaethyleneglycol. FIG. 3C shows a schematic representation of an exemplary duplex polynucleotide comprising an exemplary exonuclease resistant polynucleotide (indicated as B11), comprising a 5' overhang domain wherein the residues adjacent to the exemplary non-nucleic acid linear are attached by phosphodiester linages. FIG. 3D shows a schematic representation of an exemplary duplex polynucleotide comprising an exemplary exonuclease resistant polynucleotide (indicated as B12), comprising a 5' overhang in which three residues are linked by phosphorothioate linkage.

FIG. 4A shows a schematic representation of an exemplary duplex polynucleotide comprising an exemplary exonuclease resistant polynucleotide (indicated as B7) having an unmodified 5' overhang domain comprising only RNA bases and phosphodiester backbone connections. FIG. 4B shows a schematic representation of an exemplary duplex polynucleotide comprising an exemplary exonuclease resistant polynucleotide (indicated as B10) comprising RNA residues connected by phosphorothioate linkage and having a 5' terminal hexaethyleneglycol. FIG. 4C shows a schematic representation of an exemplary duplex polynucleotide comprising an exemplary exonuclease resistant polynucleotide (indicated as B11), comprising a 5' overhang domain wherein the residues adjacent to the exemplary non-nucleic acid linear are attached by phosphodiester linages. FIG. 4D shows a schematic representation of an exemplary duplex polynucleotide comprising an exemplary exonuclease resistant polynucleotide (indicated as B12), comprising a 5' overhang in which three residues are linked by phosphorothioate linkage where indicated.

FIG. 5A shows a schematic representation of an exonuclease resistant duplex polynucleotide suitable to be used as Dicer substrate siRNA and comprising a blocker domain. FIG. 5B shows a schematic representation of the same duplex polynucleotide of FIG. 5A without the blocker domain. In the schematic illustration of FIG. 5B the 5' overhang domain is attached via phosphodiester linkage to unmodified RNA bases.

FIG. 6A shows an exemplary exonuclease resistant duplex polynucleotide suitable to be used as Dicer substrate siRNA in the guide strand and a blocking domain at the 5' base of the passenger strand. FIG. 6B shows a schematic representation of the same duplex polynucleotide of FIG. 6A, further comprising two LNA modified bases where indicated.

FIG. 8A and FIG. 8B show data from the same assay. In particular FIG. 8A shows the result for duplex polynucleotides G pA Pb (SEQ ID NO. 1; SEQ ID NO. 13; SEQ ID NO. 14), G pA B6b (SEQ ID NO. 1; SEQ ID NO. 13; SEQ ID NO. 17; SEQ ID NO. 17), G pA B6b-R (SEQ ID NO. 1; SEQ ID NO. 13; SEQ ID NO. 19). FIG. 8B shows the result for duplex polynucleotides G2 Ac4 B7c (SEQ ID NO. 20; SEQ ID NO. 24; SEQ ID NO. 38), G2 Ac4 B7 (SEQ ID NO. 20; SEQ ID NO. 24; SEQ ID NO. 25; SEQ ID NO. 26), G2 Ac4 B10 (SEQ ID NO. 20; SEQ ID NO. 24; SEQ ID NO. 27; SEQ ID NO. 28), G2 Ac4 B11 (SEQ ID NO. 20; SEQ ID NO. 24; SEQ ID NO. 29; SEQ ID NO. 30), G2 Ac4 B12 (SEQ ID NO. 20; SEQ ID NO. 24; SEQ ID NO. 31; SEQ ID NO. 32). The figure legend refers to the final nanomolar concentration of exemplary constructs used in the dual luciferase assay.

FIG. 9A and FIG. 9B show data from the same assay. FIG. 9A shows the result for duplex polynucleotides G2 Ac4 B7c (SEQ ID NO. 20; SEQ ID NO. 24; SEQ ID NO. 38), G2 Ac4 B7 (SEQ ID NO. 20; SEQ ID NO. 24; SEQ ID NO. 25; SEQ ID NO. 26), G2 Ac4 B10 (SEQ ID NO. 20; SEQ ID NO. 24; SEQ ID NO. 27; SEQ ID NO. 28), G2 Ac4 B11 (SEQ ID NO. 20; SEQ ID NO. 24; SEQ ID NO. 29; SEQ ID NO. 30), G2 Ac4 B12 (SEQ ID NO. 20; SEQ ID NO. 24; SEQ ID NO. 31; SEQ ID NO. 32). FIG. 9B shows the result for duplex polynucleotides G3 Ac4 B7c (SEQ ID NO. 22; SEQ ID NO. 24; SEQ ID NO. 38), G3 Ac4 B7 (SEQ ID NO. 22; SEQ ID NO. 24; SEQ ID NO. 25; SEQ ID NO. 26), G3 Ac4 B10 (SEQ ID NO. 22; SEQ ID NO. 24; SEQ ID NO. 27; SEQ ID NO. 28), G3 Ac4 B11 (SEQ ID NO. 22; SEQ ID NO. 24; SEQ ID NO. 29; SEQ ID NO. 30), G3 Ac4 B12 (SEQ ID NO. 22; SEQ ID NO. 24; SEQ ID NO. 31; SEQ ID NO. 32). The figure legend refers to the final nanomolar concentration of exemplary constructs used in the dual luciferase assay.

FIG. 13 shows the inactive conformation of Medusa GA1B6b (SEQ ID NO. 1; SEQ ID NO. 3; SEQ ID NO. 17; SEQ ID NO. 18).

FIG. 14C shows a schematic representation after degradation of the 5' sensor extension by cellular exoribonuclease that results in a Dicer processing facilitating terminal phosphate.

FIG. 16A shows the inactive conformation and FIG. 16B shows the active conformation of the molecular construct.

FIG. 17A shows the inactive conformation and FIG. 17B shows the active conformation.

FIG. 18A shows a schematic representation of an exemplary exonuclease resistant duplex polynucleotide connected to a delivery vehicle by a 5' RNA linker. In the illustration of FIG. 18A, the linker is connected to the Dicer substrate siRNA via a blocker domain. FIG. 18B shows a schematic representation where exoribonuclease I (XRN1) processively degrades the linker from the 5' end of the molecular construct of FIG. 18A. FIG. 18C shows a schematic representation where processive degradation of the linker from the 5' end the molecular construct of FIG. 18A releases the Dicer substrate siRNA. FIG. 18D shows a schematic representation where the Dicer substrate siRNA released from the molecular construct of FIG. 18A is processed by Dicer.

DETAILED DESCRIPTION

Figure 1:
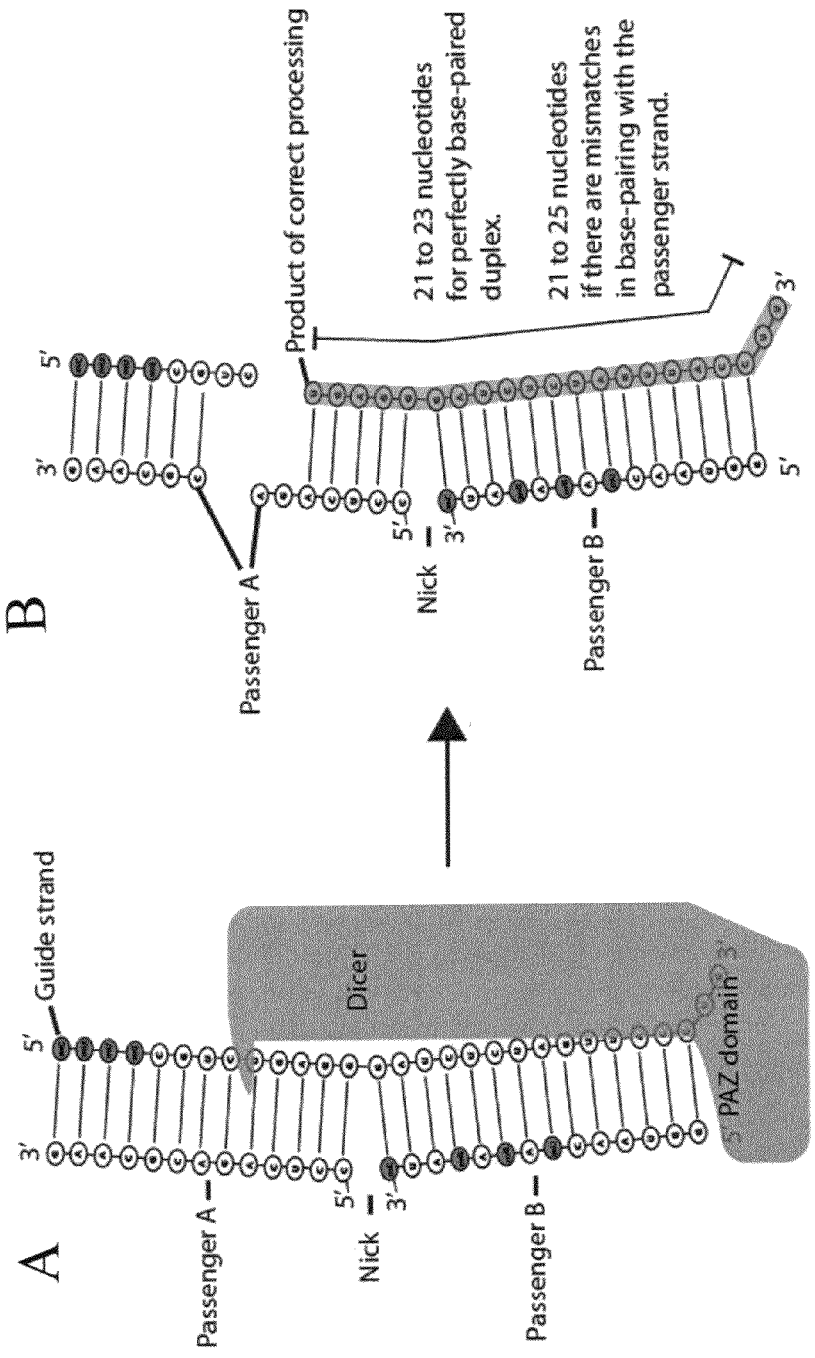
FIG. 1 shows a schematic representation of processing by Dicer of an exemplary RNA duplex suitable to be used as siRNA. In particular.

Herein described are exonuclease resistant polynucleotides and related polynucleotide duplexes, constructs, compositions, methods and systems.

The term "exonuclease" as used herein, indicates a type of enzyme that works by cleaving nucleotides one at a time from the end (exo) of a polynucleotide chain. A hydrolyzing reaction that breaks phosphodiester bonds at either the 3' or the 5' end occurs. A 3' and 5' exonuclease can degrade RNA and DNA in cells, and can degrade RNA and DNA in the interstitial space between cells and in plasma, with a high efficiency and a fast kinetic rate. Its close relative is the endonuclease, which cleaves phosphodiester bonds in the middle (endo) of a polynucleotide chain. 3' and 5' exonuclease and exonucleolytic complexes can degrade RNA and DNA in cells, and can degrade RNA and DNA in the interstitial space between cells and in plasma. The term "exoribonuclease" as used herein, is an exonuclease ribonuclease, which are enzymes that degrade RNA by removing terminal nucleotides from either the 5' end or the 3' end of the RNA molecule. Enzymes that remove nucleotides from the 5' end are called 5'-3' exoribonucleases, and enzymes that remove nucleotides from the 3' end are called 3'-5' exoribonucleases.

The term "exonuclease resistant" as used herein with reference to a molecule and in particular a polynucleotide, indicates resistance to exonucleolytic degradation. Exonucleolytic degradation is the processive degradation of an oligonucleotide from the 5' or 3' end by enzymes called exonucleases. Exonucleases are enzymes that work by cleaving nucleotides one at a time from the end (exo) of a polynucleotide chain. A hydrolyzing reaction that breaks phosphodiester bonds occurs. Its close relative is the endonuclease, which cleaves phosphodiester bonds in the middle (endo) of a polynucleotide chain.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Exemplary functional groups that can be comprised in an analog include methyl groups and hydroxyl groups and additional groups identifiable by a skilled person.

Exemplary monomers of a polynucleotide comprise deoxyribonucleotide, ribonucleotides, Locked Nucleic Acid (LNA) nucleotides and Peptide Nucleic Acid (PNA) nucleotides. The term "deoxyribonucleotide" refers to the monomer, or single unit, of DNA, or deoxyribonucleic acid. Each deoxyribonucleotide comprises three parts: a nitrogenous base, a deoxyribose sugar, and one or more phosphate groups. The nitrogenous base is typically bonded to the 1' carbon of the deoxyribose, which is distinguished from ribose by the presence of a proton on the 2' carbon rather than an —OH group. The phosphate group is typically bound to the 5' carbon of the sugar. The term "ribonucleotide" refers to the monomer, or single unit, of RNA, or ribonucleic acid. Ribonucleotides have one, two, or three phosphate groups attached to the ribose sugar. The term "locked nucleic acids" (LNA) as used herein indicates a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. The locked ribose conformation enhances base stacking and backbone pre-organization. This significantly increases the thermal stability (melting temperature) of oligonucleotides. LNA oligonucleotides display unprecedented hybridization affinity toward complementary single-stranded RNA and complementary single- or double-stranded DNA. Structural studies have shown that LNA oligonucleotides induce A-type (RNA-like) duplex conformations. The term "polyamide polynucleotide", "peptide nucleic acid" or "PNA" as used herein indicates a type of artificially synthesized polymer composed of monomers linked to form a backbone composed of repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. In some embodiments, polynucleotides can comprise one or more non-nucleotidic or non nucleosidic monomers identifiable by a skilled person.

Accordingly, the term "polynucleotide" includes nucleic acids of any length, and in particular DNA, RNA, analogs thereof, such as LNA and PNA, and fragments thereof, possibly including non-nucleotidic or non-nucleosidic monomers, a each of which can be isolated from natural sources, recombinantly produced, or artificially synthesized. Polynucleotides can typically be provided in single-stranded form or double-stranded form (herein also duplex form, or duplex).

A "single-stranded polynucleotide" refers to an individual string of monomers linked together through an alternating sugar phosphate backbone. In particular, the sugar of one nucleotide is bond to the phosphate of the next adjacent nucleotide by a phosphodiester bond. Depending on the sequence of the nucleotides, a single-stranded polynucleotide can have various secondary structures, such as the stem-loop or hairpin structure, through intramolecular self-base-paring. A hairpin loop or stem loop structure occurs when two regions of the same strand, usually complementary in nucleotide sequence when read in opposite directions, base-pairs to form a double helix that ends in an unpaired loop. The resulting lollipop-shaped structure is a key building block of many RNA secondary structures. The term "small hairpin RNA" or "short hairpin RNA" or "shRNA" as used herein indicate a sequence of RNA that makes a tight hairpin turn and can be used to silence gene expression via RNAi.

A "double-stranded polynucleotide", "duplex polynucleotide" refers to two single-stranded polynucleotides bound to each other through complementarily binding. The duplex typically has a helical structure, such as double-stranded DNA (dsDNA) molecule or double stranded RNA, is maintained largely by non-covalent bonding of base pairs between the strands, and by base stacking interactions.

In embodiments herein described, an exonuclease resistant polynucleotide comprises a blocker domain providing the polynucleotide with exonuclease resistance.

A "domain" in the sense of the present disclosure indicates a part of a given polynucleotide having a structure specifically associated with a function and that exist independently of the rest of the polynucleotide. The structure/function association in a domain is typically conserved during the chemical and/or biological reaction associated with the polynucleotide. A "blocker domain" in the sense of the present disclosure indicates a part of the polynucleotide having the function of reducing polynucleotide degradation by exonuclease activity.

In exonuclease resistant polynucleotide herein described, the blocker domain is formed by a non-nucleic acid polymer segment and a phosphorothioate segment.

The term "non-nucleic acid polymer" as used herein refers to molecule composed of repeated subunits, known as monomers which do not comprise nucleotides or modified nucleotides linked by a phosphodiester or phosphothioate linkages. The physical properties of a polymer, such as flexibility, chain mobility strength and toughness are dependent on the size or length of the polymer chain. A common means of expressing the length of a chain is the degree of polymerization, which quantifies the number of monomers incorporated into the chain. As with other molecules, a polymer's size can also be expressed in terms of molecular weight. The weight of a polymer is often expressed statistically to describe the distribution of chain lengths present in the same. Common examples are the number average molecular weight and weight average molecular weight. The ratio of these two values is the polydispersity index, commonly used to express the "width" of the molecular weight distribution. An additional measurement is contour length, which can be understood as the length of the chain backbone in its fully extended state. Exemplary non-nucleic acid polymers comprise alkanes, polyamides, polyethers, polyesters, polycarbonates, polysaccharides, polypeptides, polypropylenes, aliphatic chains, polymers with heterogeneous residues and residue to residue linkage chemistry and additional polymers identifiable by a skilled person.

The term "linear polymer" as used herein indicates a polymer wherein the residues are connected in a single linear and non-circular chain without branches. The flexibility of an unbranched chain polymer is characterized by its persistence length. The term "persistence length" as used herein refers to the length over which correlation in the direction of the ends of the polymer are lost. The persistence length is a basic mechanical property quantifying the stiffness of a polymer and is measurable with methods identifiable The term "segment" as used herein indicates a portion of a polynucleotide or construct having chemical and/or biological properties that are functional to the chemical and/or biological properties of the entire polynucleotide or construct as a whole. The term "segment" as used herein in connection with a signal activated construct indicates a portion of a signal activated construct having chemical and/or biological properties that are functional to changes in conformation of the signal activated construct or components thereof, and/or to a related ability to perform the enzyme assisted release herein described.

In particular, in blocker domain herein described the non-nucleic acid polymer segment comprises a linear polymer having two to six monomer residues linked by residue to residue bonds. The term "residue to residue bond" refers to a covalent bond connecting consecutive residues of the polymer.

In particular, in embodiments herein described, the end to end distance for the non-nucleic acid linear polymer in fully extended conformation can be up to about 1.00 nm, and in particular can be about 0.2 nm, about 0.4 nm, about 0.5 nm, about 0.65, about 0.8 nm, about 0.9 nm and about 1 nm. The end to end distance for the fully extended polymer can be determined by drawing the polymer in a maximally extended configuration with optimal bond length and bond angles expected for the monomer residues and measuring the distance between the first atom and the last atom in the polymer chain (see Examples section and in particular Example 11 and Example 12).

In embodiments herein described, the non-nucleic acid linear polymer has a persistence length of the polymer up to about 0.5 nm. In particular in embodiments herein described the persistence length can be about 0.38 nm. (see Examples section and in particular Example 11 and Example 12).

In embodiments herein described the non-nucleic acid linear polymer has stability such that polymer degradation is not faster than an unmodified RNA with the same number of monomers measured by gel shift assay or mass spectroscopy. Polymer degradation is not faster than an unmodified RNA when under comparable degradation conditions the average length of the polymer is equal to or longer than the length of the unmodified RNA. For example, a polymer of N residues can be incubated in cell lysate at 37° C. and compared with a control oligonucleotide with an equal number of nucleotides and the average length of the polymer over time can be measured by mass spectroscopy and compared to the control oligonucleotide. Under these conditions, the half-life of the full length polymer is longer than the half-life of the full length control oligonucleotide when the polymer degradation is not faster than an unmodified RNA.

In embodiments herein described the non-nucleic acid linear polymer has no covalent cross reactivity with the PAZ domain of Dicer which can be determined by radiolabeling experiments comprising providing a PAZ domain in a cell lysate buffer, contacting a candidate polymer labeled with a terminal $P_{32}$ at 25 C temperature for a time and under condition to allow interaction of the PAZ domain and the labeled non-nucleic acid linear polymer. Following the contacting the method comprises further extracting the protein under denaturing conditions and detecting the radioactivity using suitable techniques such as Western Blot or other techniques identifiable by a skilled person. Additional methodology to measure covalent cross reactivity between the non-nucleic acid linear polymer and PAZ domain are identifiable by a skilled person.

In embodiments herein described, the degradation can occur as fast, or faster than the unmodified RNA as long as the degradation occurs such that a terminal phosphate is exposed or a terminal —OH group that can be phosphorylated by a kinase is exposed. A method to test the kination is to incubate the —OH terminated polymer with the target kinase in the appropriate buffer with P32 labeled Adenosine triphosphate as a source of the phosphate and detect labeling of the polymer with radioactive P32.

In some embodiments, polymers suitable to be comprised in the non-nucleic acid polymer segment as non-nucleic acid linear polymer herein described comprise a substituted or unsubstituted alkyl chain, a polyether, a polypeptide (alkanes, polyamides, polyethers, polyesters, polycarbonates, polysaccharides, polypeptides, polypropylenes, aliphatic chains, polymers with heterogeneous residues and residue to residue linkage chemistry) as well as additional polymers that show the required number of residues, end-to-end distance, persistence length, stability and cross reactivity as will be understood by a skilled person. In particular in some embodiments, non-nucleic acid linear polymers comprising different but chemically compatible monomer units (e.g. an amino acid flanked by an alkyl monomer) can be comprised in the non-nucleic acid polymer segment as long as such the required number of residues, end-to-end distance, persistence length, stability and cross reactivity as will be understood by a skilled person In exonuclease resistant polynucleotide herein described the phosphorothioate segment of the blocker domain comprises at least one to five nucleotides linked by phosphorothioate linkages to form a phosphorothioate sequence having a 5' and a 3' end, and attaching at the 5' end the first end of the non-nucleic acid polymer segment through a phosphodiester linkage.

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. The term "phosphorothioate linkage" as used herein, indicates a bond between nucleotides in which one of the nonbridging oxygens is replaced by a sulfur. The term "phosphodiester linkage" as described herein indicates the normal sugar phosphate backbone linkage in DNA and RNA wherein a phosphate bridges the two sugars.

In particular, in a blocker domain herein described the phosphorothioate sequence comprises at least two bases wherein the at least two bases are connected by a phosphorothioate linkage. The bases can be modified or unmodified nucleotides, nucleosides, and related analog forming RNA, DNA, or alternative nucleic acids as would be understood by a person skilled in the art.

The term "modified nucleotides" refers to a nucleic acid monomer that is not the standard DNA or RNA nucleotide or nucleoside. In particular, modified nucleotides comprise nucleotide analogs presenting one or more individual atoms which have been replaced with a different atom or with a different functional group. Exemplary functional groups that can be comprised in an analog include methyl groups and hydroxyl groups and additional groups identifiable by a skilled person.

The term "present" as used herein with reference to a compound or functional group indicates attachment performed to maintain the chemical reactivity of the compound or functional group as attached. Accordingly, a functional group presented on residue, a segment, or a molecule is able to perform under the appropriate conditions the one or more chemical reactions that chemically characterize the functional group.

In particular, a modified nucleotide in the sense of the disclosure can be any nucleotides or nucleosides modified in the 2' position with a group that interferes with hydrogen bonding. In particular, modified nucleotide such has 2' O-methyl, 2'F 2'NH$_4$ and additional groups identifiable by a skilled person can be used in polynucleotides herein described. Exemplary modified nucleotide can also include locked nucleic acids alone or in combination with be 2' O-methyl, and/or 2' Fluoro modified residues.

In some embodiments, the phosphorothioate segment can have two to three residues modified to present a 2' O-methyl. In an exemplary modification schematically illustrated in FIG. 2, a first phosphorothioate links the first nucleotide, a mG, to a second nucleotide mG, and a second phosphorothioate links the second nucleotide mG to the third nucleotide mU.

In embodiments of the exonuclease resistant polynucleotide herein described, inclusion of a phosphodiester linkage between the phosphorothioate sequence and the linear polymer of the non-nucleic acid polymer segment allows the resulting polynucleotide, when comprised at the 5' end of either strands of a duplex polynucleotide configured to allow processing by Dicer and/or argonaute to maintain the duplex' processability by Dicer and/or Argonaute (see FIG. 1 and related description).

Figure 8:
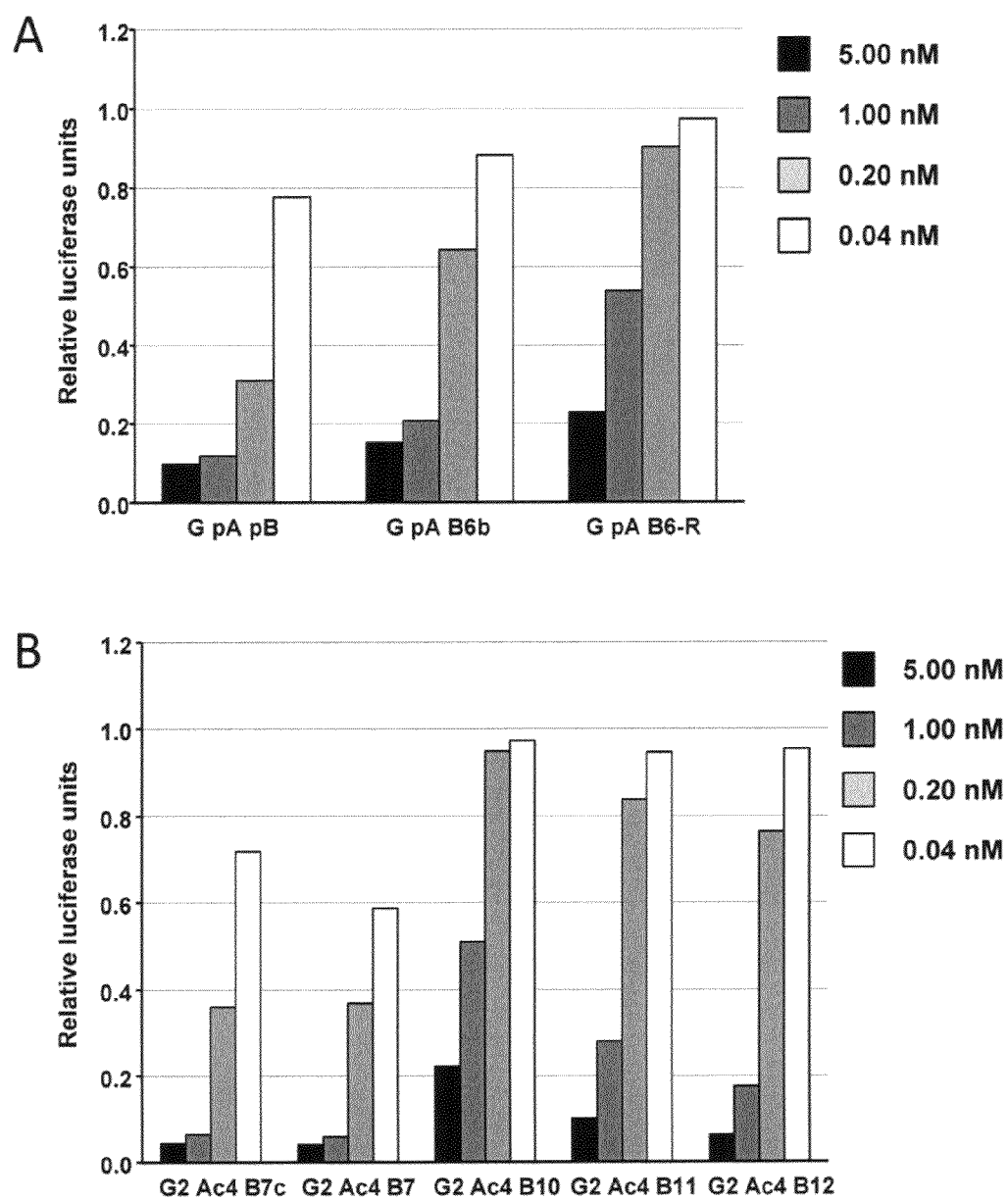
FIG. 8 shows a diagram illustrating the results of a luciferase assay of exemplary constructs comprising an exonuclease resistant duplex polynucleotide herein described, where the y-axis represents relative luciferase units and the x-axis represents the exemplary complexes used in the assay.
Figure 9:
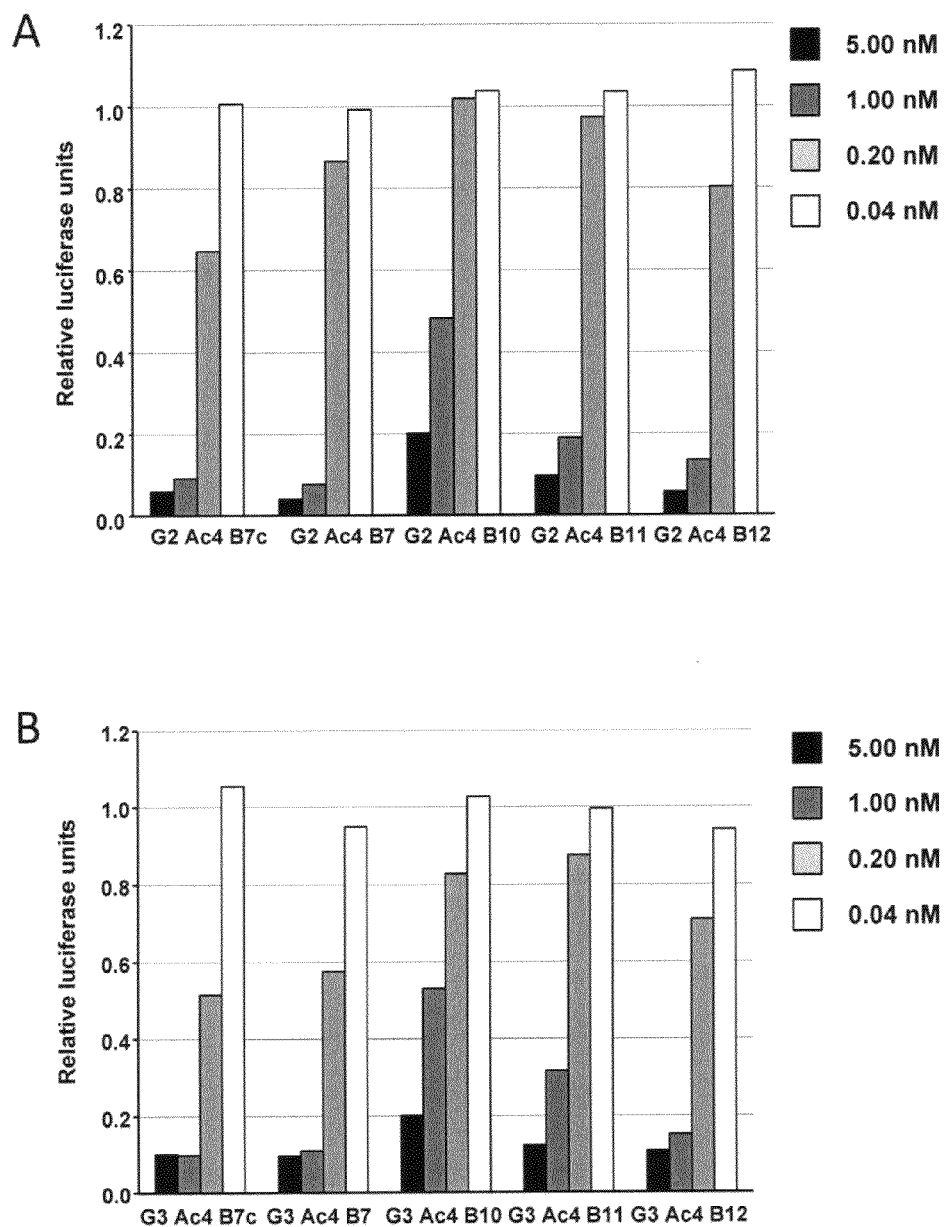
FIG. 9 shows a diagram illustrating the results of a luciferase assay of exemplary constructs comprising an exonuclease resistant duplex polynucleotide herein described, where the y-axis represents relative luciferase units and the x-axis represents the exemplary complexes used in the assay.
Figure 10:
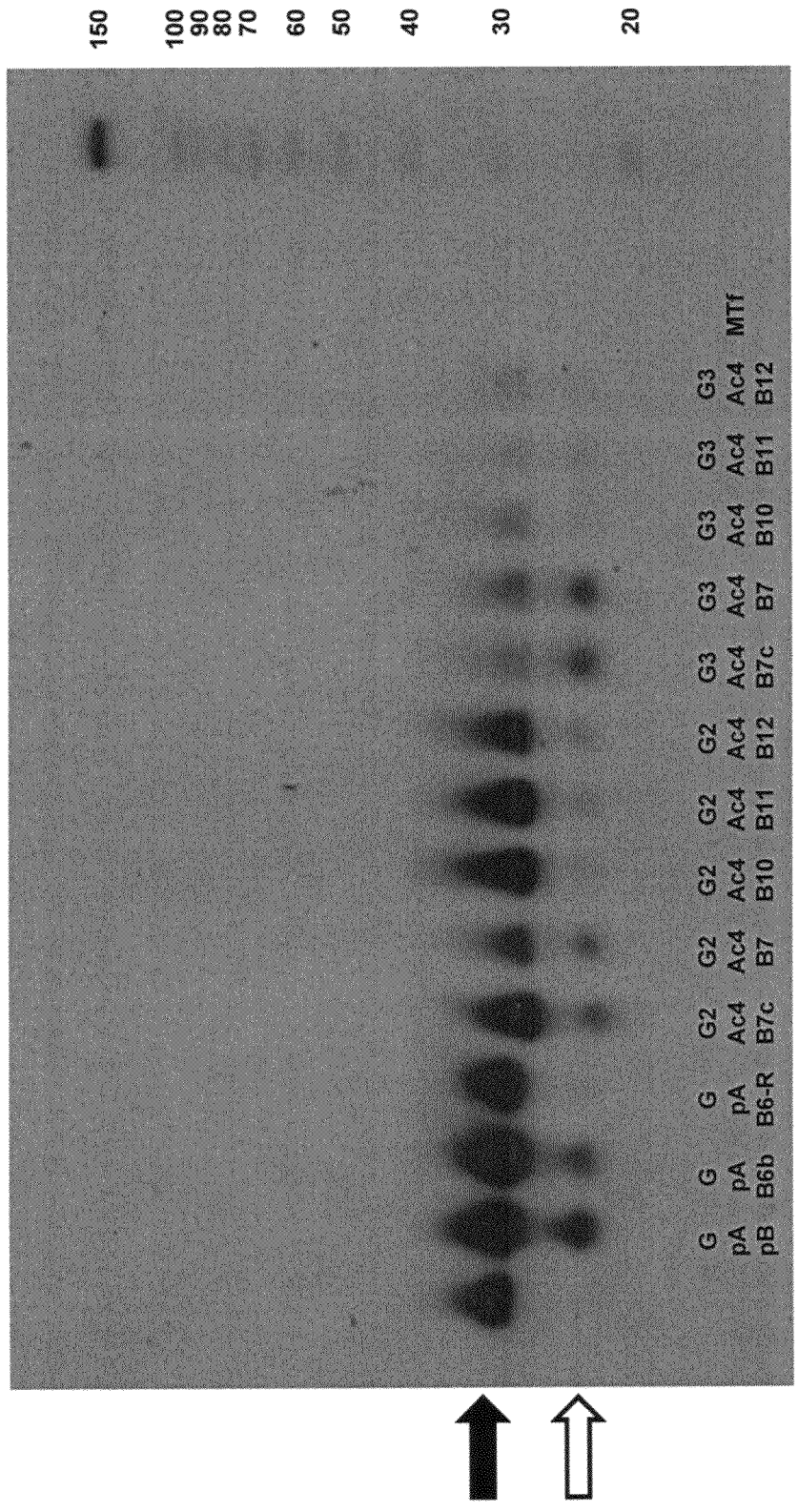
FIG. 10 shows a Northern blot performed with a probe for the guide strand of exemplary constructs comprising an exonuclease resistant duplex polynucleotide herein described. In particular, in the illustration of FIG. 10, Lane 1, contains an irrelevant construct; lane 2, G pA pB (SEQ ID NO. 1; SEQ ID NO. 13; SEQ ID NO. 14); lane 3, G pA B6b (SEQ ID NO. 1; SEQ ID NO. 13; SEQ ID NO. 17; SEQ ID NO. 18); lane 4 G pA B6-R (SEQ ID NO. 1; SEQ ID NO. 13; SEQ ID NO. 19); lane 5, G2 Ac4 B7c (SEQ ID NO. 20; SEQ ID NO. 24; SEQ ID NO. 38); lane 6, G2 Ac4 B7 (SEQ ID NO. 20; SEQ ID NO. 24; SEQ ID NO. 25; SEQ ID NO. 26); lane 7, G2 Ac4 B10 (SEQ ID NO. 20; SEQ ID NO. 24; SEQ ID NO. 27; SEQ ID NO. 28; SEQ ID NO. 29); lane 8, G2 Ac4 B11 (SEQ ID NO. 20; SEQ ID NO. 24; SEQ ID NO. 29; SEQ ID NO. 30); lane 9, G2 Ac4 B12 (SEQ ID NO. 20; SEQ ID NO. 24; SEQ ID NO. 31; SEQ ID NO. 32); lane 10, G3 Ac4 B7c (SEQ ID NO. 22; SEQ ID NO. 24; SEQ ID NO. 38); lane 11, G3 Ac4 B7 (SEQ ID NO. 22; SEQ ID NO. 24; SEQ ID NO. 25; SEQ ID NO. 26); lane 12, G3 Ac4 B10 (SEQ ID NO. 22; SEQ ID NO. 24; SEQ ID NO. 27; SEQ ID NO. 28); lane 13, G3 Ac4 B11 (SEQ ID NO. 22; SEQ ID NO. 24; SEQ ID NO. 29; SEQ ID NO. 30); lane 14, G2 Ac4 B12 (SEQ ID NO. 22; SEQ ID NO. 24; SEQ ID NO. 31; SEQ ID NO. 32); lane Mtf, Mock transfected (carrier only); Lane M, RNA size markers, number of nucleotides is indicated.

Reference is made to the Examples section and in particular to Examples 10, 11, and 12, showing that when the exonuclease resistant polynucleotide herein described is included in a Dicer and/or argonaute processable duplex, the exonuclease resistant polynucleotide maintains the ability of the duplex to be processed by Dicer. FIGS. 8 and 9 show the RNAi activity of the exemplary constructs incorporation. FIG. 10 measures processing of the exemplary constructs by Dicer.

In some embodiments, in exonuclease resistant polynucleotides herein described any number of unmodified nucleotides, depending on the experimental design, can be placed adjacent to the phosphorothioate sequence upstream of the blocking domain from the direction of exonucleases cleavage as long as the resulting segment does not prevent presentation of the second end of the non-nucleic acid linear polymer. In some embodiments, downstream of the blocker domain, the exonuclease resistant polynucleotide herein described comprises no further nucleotide. In some embodiments, any number of modified or unmodified bases can be placed downstream of the blocker domain, and the pattern can be adjusted according to requirements of the particular application depending on experimental design with the constraint that the number and sequence does not prevent presentation of the second end of the non-nucleic acid linear polymer at the 5' end of the polynucleotide.

In some embodiments, the exonuclease resistant polynucleotide further comprises a 5' overhang domain having a 5' end and a 3' end, which is presented on the 5' end of the exonuclease resistant polynucleotide attached to the second end of the non-nucleic acid polymer segment.

The term "overhang" as described herein, refers to a stretch of unpaired nucleotides at one of the ends of a double stranded polynucleotide. In particular, in an overhang the unpaired nucleotides can be on either strand of the polynucleotide, and can be included at either the 3' end of the strand ('3' overhangs) or at the 5' end of the strand (5' overhangs).

In embodiments, herein described, the 5' overhang domain can comprise any number of modified or unmodified nucleotides in accordance with the experimental design where the number and sequence is compatible with a desired folding of the polynucleotide and/or related duplex polynucleotides and/or molecular constructs. In some embodiments, the 5' overhang domain can comprise between 1 and 10,000 nucleotides. In some embodiments, one or more phosphodiester linkage in the 5' overhang domain can be substituted with phosphorothioate linkage.

In particular, in some embodiments, the 5' overhang domain can comprise modified or unmodified nucleotides with possible substitution of one or more phosphodiester linkage with a phosphorothioate linkage, according to a pattern configured to control rate of degradation. In particular, as shown in the present disclosure, the substitution of RNA and DNA bases with modified nucleotide alone or in combination with presence of phosphorothioate linkage can be used to reduce the rate of nuclease degradation with respect to the rate of a base sequence in a controllable fashion as shown in FIG. 3, FIG. 4, FIG. 8 and FIG. 9, and related Example 11 and Example 12. In particular, an increased presence of modified nucleotides and/or phosphorothioate linkages in the 5' overhang domain is associated with an increased resistance as will be understood by a skilled person upon reading of the present disclosure.

Therefore, in some embodiments the number and composition of the 5' overhang domain compatible with a set folding of the exonuclease resistant duplex polynucleotide or related construct, is selected to have a pattern of modifications and/or substitutions configured to control rate of degradation of the 5' overhang domain as measured, for example, by time point measurements (Example 11 and Example 12) and/or additional methods identifiable by a skilled person. Identification of a pattern associated with a set controlled rate of degradation can be performed by providing one or more candidate patterns for a desired polynucleotide sequence, detecting the resulting degradation rate under set conditions and selecting the candidate pattern associated with the set degradation rate.

In general, in some embodiments, an exonuclease resistant polynucleotide herein described can comprise along the entire polynucleotide modified nucleotides such as 2' O-methyl, 2'Fluoro, LNA (Locked Nucleic Acid), and others as can be understood by persons of skill in the art. In some embodiments an exonuclease resistant polynucleotide herein described can comprises a modified backbone comprising a phosphorothioate, peptide, or other non-phosphodiester linkages along the entire polynucleotide in accordance with the experimental design. In some embodiments an exonuclease resistant polynucleotide can comprise a modification of the 5' or 3' end of the polynucleotide such as a polyethylene glycol, an inverted dT, a polypeptide thereby preventing access thereto by a blocking group. In some embodiments, a polynucleotide base paired with the 5' or 3' segments or a protein complexed to the 5' or 3' segments. Additional exonuclease resistant polynucleotides embodiments include combinations of for example the modified nucleotides, modified backbone, and blocking groups. Additional exonuclease resistant polynucleotide include those understood by persons skilled in the art to block or limit the ability of exonuclease to act. Exonuclease resistance can be detected with several methods identifiable by a skilled person. In accordance with an exemplary method to detect exonuclease resistance, a candidate exonuclease resistant strand and a control strand that is known to not be exonuclease resistant can be both incubated with for example exonuclease I, and the amount of intact strand can be compared, by for example either gel shift assay or mass spectrometry for quantitative and/or qualitative detection of degradation as will be understood by a skilled person.

In some embodiments, the exonuclease resistant polynucleotide can have the following formula $$5'-(A_1)n-X-N_1N_2N_3-A_2-3' \quad \text{(SEQ ID NO. 49)} \tag{I}$$

wherein $A_1$ is an oligonucleotide comprising any number of modified or unmodified nucleotides, and in particular can comprise 2 to 10 Kb or more, more particularly about up to 100 nucleotides;

$A_2$ is any number of modified or unmodified nucleotides, in particular $A_2$ can comprise up to 100 modified or unmodified nucleotides and in particular from 2 to 67 modified or unmodified nucleotides, and more particularly A2 can be an oligonucleotide comprising from 2 to 47 modified or unmodified nucleotides;

$N_1$ $N_2$ and $N_3$ are independently any modified or unmodified nucleotides, and in particular can comprise one or more of 2' O-methyl, 2'F, and/or 2'NH4 alone or in combination with one LNA residue or $X_1$ is a non-nucleic acid polymer and in particular can be an alkyl, polyether or polypeptide polymer, more particularly a C2-C6 alkyl, a 2×PEG to 3×PEG or a two amino acid polypeptide;

n, can be 0 or 1, wherein each of $A_1$ and $N_1$ is lined to X through a phosphodiester linkage and each of $N_1$ and $N_3$ is linked to $N_2$ through a phosphorothioate linkage In particular, in embodiments where the exonuclease resistant polynucleotide has Formula I, the blocker domain is formed by the moiety 5'X-$N_1$-$N_2$-$N_3$-3', in which X is the non-nucleic acid polymer segment and 5'$N_1$-$N_2$-$N_3$-3' is the phosphorothioate segment A1 is the 5' overhang domain and $A_2$ is the sequence upstream to the blocker domain.

In some embodiments, $A_t$ can be formed by DNA, RNA bases, or modified nucleotides that are not nuclease resistant and/or contain one or more phosphorotiate lingage in accordance with a pattern to control the $A_1$ degradation rate.

In some embodiments $X_1$ can be a $C_3$ alkyl chain, or a longer alkyl segment such as a $C_1$, $C_2$, $C_4$, $C_5$, a tri-ethylene glycol, or a hexa-ethylene glycol.

In some embodiments, $N_1$, $N_2$ and $N_3$ can be 2-O-methyl nucleotides. In addition or in the alternative at least one of $N_1$, $N_2$ and $N_3$ can be 2'-F, or LNA.

In some embodiments, $A_2$ can be an oligonucleotide that can be modified or unmodified, as needed for the particular design.

In some embodiments, the exonuclease resistant polynucleotide herein described, has sequence

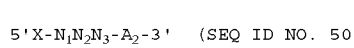
5'-X-N₁N₂N₃-A₂-3' (SEQ ID NO. 50) (II)

wherein X, N₁, N₂, N₃ and A₂ have the meaning indicated for the exonuclease resistant polynucleotide of Formula (I).

In an embodiment described herein, the exonuclease resistant polynucleotide has sequence

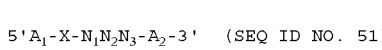
5'-A₁-X-N₁N₂N₃-A₂-3' (SEQ ID NO. 51) (III)

wherein X, N₁, N₂, N₃ and A₂ have the meaning indicated for the exonuclease resistant polynucleotide of Formula (I).

Figure 3:
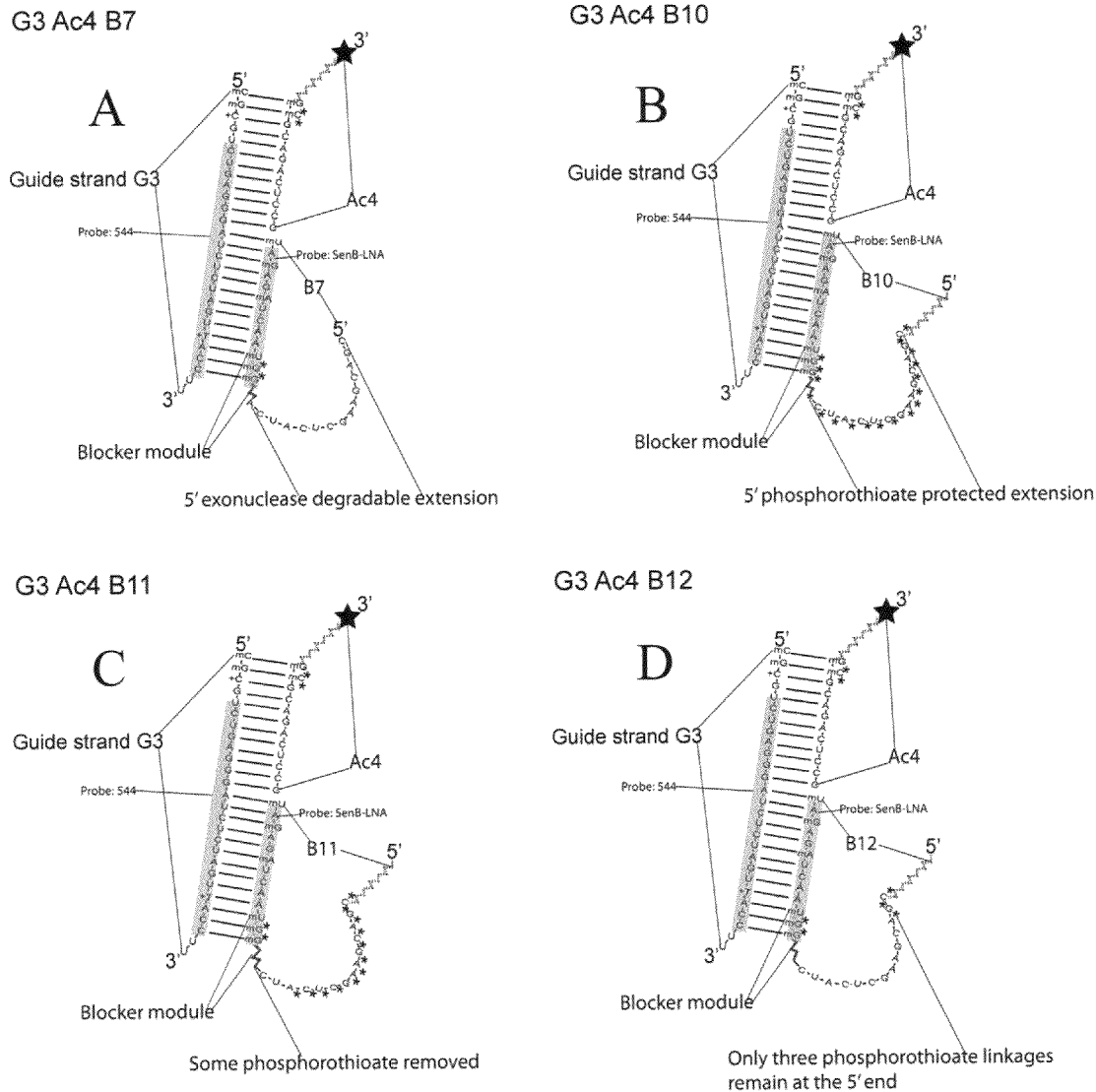
FIG. 3 shows a schematic representation of exemplary exonuclease resistant duplex polynucleotides wherein the blocker domain attaches a 5' overhang domain and the guide strand comprises two LNA bases. The positions probed by Northern blot probes 544 and SenB-LNA are shown highlighted in gray. In particular.
Figure 4:
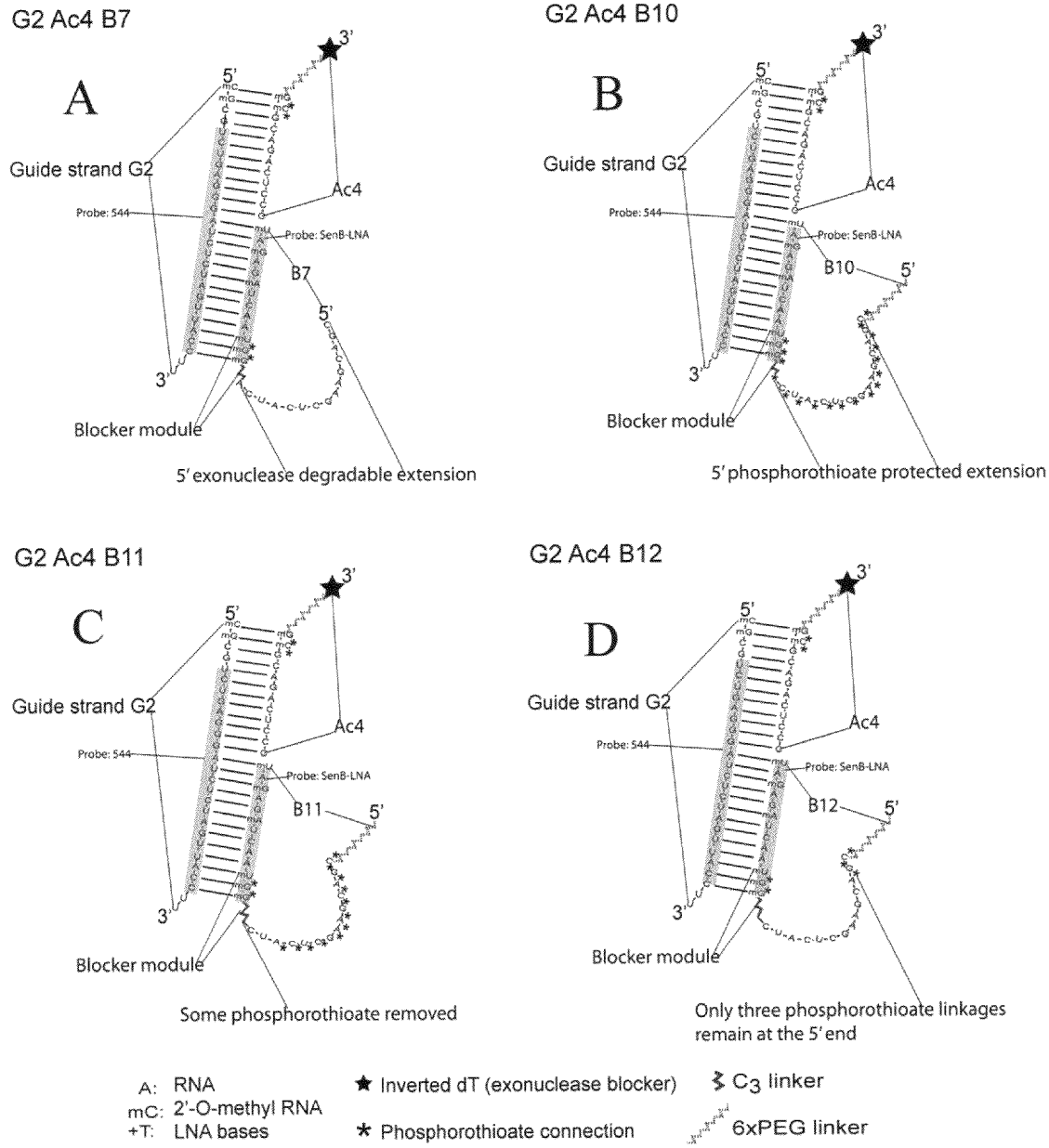
FIG. 4 shows a schematic representation of exemplary exonuclease resistant duplex polynucleotides wherein the blocker domain attaches a 5' overhang domain and which does not comprise LNA residues in the guide strand. The positions probed by Northern blot probes 544 and SenB-LNA are shown highlighted in gray. In particular.

In some embodiments, an exonuclease polynucleotide of formula (I), (II) and (III) minimizes 5'→3' exonuclease degradation at position X. as schematically illustrated for example in FIGS. 3 and 4 and Example 11 and Example 12. Detection of degradation can be performed by detecting an initial length of the polynucleotides and then subjecting the strand to exonuclease degradation and then detecting the length of the product to compare the detected length to the length of the exonuclease resistant polynucleotide, e.g. by northern blotting or mass spectrometry, as will be understood by a skilled person (see Example 11 and Example 12 and FIGS. 10 and 11).

In some embodiments, exonuclease resistant polynucleotide herein described can be used within an exonuclease resistant duplex polynucleotide. In some of those embodiments, the duplex polynucleotide comprises a duplex RNA having a length of about 17 to about 30 bp and comprising a guide strand complementary bound to a passenger strand.

The term "complementary" as used herein indicates a property of single stranded polynucleotides in which the sequence of the constituent monomers on one strand chemically matches the sequence on another other strand to form a double stranded polynucleotide. Chemical matching indicates that the base pairs between the monomers of the single strand can be non-covalently connected via two or three hydrogen bonds with corresponding monomers in the another strand. In particular, in this application, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA:RNA duplexes as well as intramolecular base paring duplexes formed by complementary sequences of a single polynucleotide strand (e.g. hairpin loop).

The term 'complementary bind", "base pair", "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

The term "thermodynamic stability" as used herein indicates a lowest energy state of a chemical system. Thermodynamic stability can be used in connection with description of two chemical entities (e.g. two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

In embodiments herein described, in the duplex RNA each of the guide strand and passenger strand has a 5' end and a 3' end is in a configuration allowing processing of the guide strand by dicer and/or an argonaute enzyme.

The term "Dicer" as described herein refers an endoribonuclease in the RNase III family that cleaves double-stranded RNA (dsRNA) and pre-microRNA (miRNA) into short double-stranded RNA fragments about 20-25 base pairs long, with a two-base overhang on the 3' end. Dicer contains two RNase III domains and one PAZ domain; the distance between these two regions of the molecule is determined by the length and angle of the connector helix and influences the length of the siRNAs it produces. The term "PAZ domain" refers to a domain named "PAZ" after the proteins Piwi Argonaut and Zwille identifiable by a skilled person. The PAZ domain is present in both Dicer and Argonaute proteins. In Dicer, PAZ binds the characteristic OH terminated two-base 3' overhangs and flush Phosphate terminated 5' end of siRNAs. In Argonaute the Paz domain recognizes the phosphorylated 5' end of the RNA guide strand in RNA induced silencing complexes. Dicers interact with several partner proteins (TRBP in humans, R2D2, Logs in *Drosophila*). These partner proteins could play a role in dictating the substrate specificity of Dicer proteins. Dicer facilitates the formation of the RNA-induced silencing complex (RISC), whose catalytic component argonaute is an endonuclease capable of degrading messenger RNA (mRNA). The human version of this gene is DICER1. Dicer and other miRNA processing enzymes can be used in cancer prognosis. Specifically Dicer cleavage requires a 5'-terminal phosphate group a novel basic motif (5' pocket) in Dicer can recognize the 5'-phosphorylated end. In several embodiments described herein, degradation by XRN1 can lead to exposure of a 5' phosphorylated end that can be further processed in a Dicer mechanism.

The term "Argonaut" as described herein refers to proteins that are the catalytic components of the RNA-induced silencing complex (RISC), the protein complex responsible for the gene silencing phenomenon known as RNA interference (RNAi). Argonaute proteins can bind several classes of small non-coding RNAs, including microRNAs (miRNAs), small interfering RNAs (siRNAs) and Piwi-interacting RNAs (piR-NAs). Small RNAs guide Argonaute proteins to their specific targets through sequence complementarity, which typically leads to silencing of the target. Some Argonaute proteins can have endonuclease activity directed against messenger RNA (mRNA) strands that display extensive complementarity to their bound small RNA, and this is known as "Slicer activity." These proteins have been also associated to selection of the guide strand and destruction of the passenger strand of the siRNA substrate. For site recognition, the phosphorylated 5' end of the RNA strand enters a conserved basic surface pocket (the PAZ domain) and makes contacts through a divalent cation such as magnesium and by aromatic stacking between the 5' nucleotide in the siRNA and a conserved tyrosine residue. This site is thought to form a nucleation site for the binding of the siRNA to its mRNA target.

In some embodiments, duplex polynucleotides herein described can be nicked to allow the duplex to more than one configuration. The term "nicked" as used herein with reference to a polynucleotide strand of a double stranded polynucleotides, indicates a gap in the direct covalent linkage between two nucleotides of the polynucleotide chain forming the strand that are engaged in complementary binding within double stranded polynucleotide. Accordingly, an RNA duplex comprising a nicked passenger strand can be obtained by cleaving the covalent linkage between suitable nucleotides e.g. by using suitable endoribonucleases (such as an RNAase III enzyme) or by synthesis of the a double stranded polynucleotide with selected dideoxyribonucleotides used to introduce the nick as will be understood by a skilled person. Additional approaches will also be identifiable by the skilled person directed to obtain a passenger strand in which two of the nucleotides forming the polynucleotide chain engaged in the complementary binding with the guide strand are not directly covalently linked to each other.

Reference is made to the illustration of FIG. 1, which shows an exemplary schematic of a duplex RNA which has a length of 27 bp and comprises a guide strand complementary bound and a passenger strand configuration allowing processing of the guide. illustrates processing of a Dicer substrate siRNA by Dicer. The Dicer PAZ domain binds the terminal 3' UU overhang on the guide strand and the flush 5' phosphate end of passenger strand and serves as a molecular ruler and endonuclease to release a 21 to 23 nucleotide long guide strand highlighted in gray. This strand is then processed and loaded into an RNA induced silencing complex (RISC) as the guide strand, as will be understood by a skilled person.

An RNA duplex is usually Dicer processable if the duplex is at least 21 base-pairs in length, has at least one end with a flush 5' phosphate terminus with a 2 to 6 base 3' overhang. The 5' terminus can also be terminated with an OH. In this case the strand can be phosphorylated with cellular kinases. Duplexes longer than 30 base pairs are inhibitory for Dicer processing. A duplex can be loaded into Argonaute without Dicer processing if the duplex was from 17 basepairs to 19 base pairs with at least one terminus having a 2 base 3' overhang and a flush 5' terminus. Dicer processing can be checked via incubation with purified Dicer enzymes followed by denaturing PAGE gel electrophoresis. Dicer processing is expected to produce one or more clear bands of 21 to 23 nucleotide single stranded products that is shorter than the original strands in the duplex. Loading into Argonaute can be checked by incubating the duplexes in cells, followed by immunoprecipitationg of RISC complexes and extraction of the guide strands incorporated in RISC. The guides strands can then be sequenced or detected via polymerase chain reaction based methods In exonuclease resistant duplex polynucleotides herein described, the exonuclease resistant polynucleotide herein described is comprised in the passenger strand in a configuration in which the second end of non-nucleic acid polymer is presented at the 5' end of the passenger strand.

Figure 2:
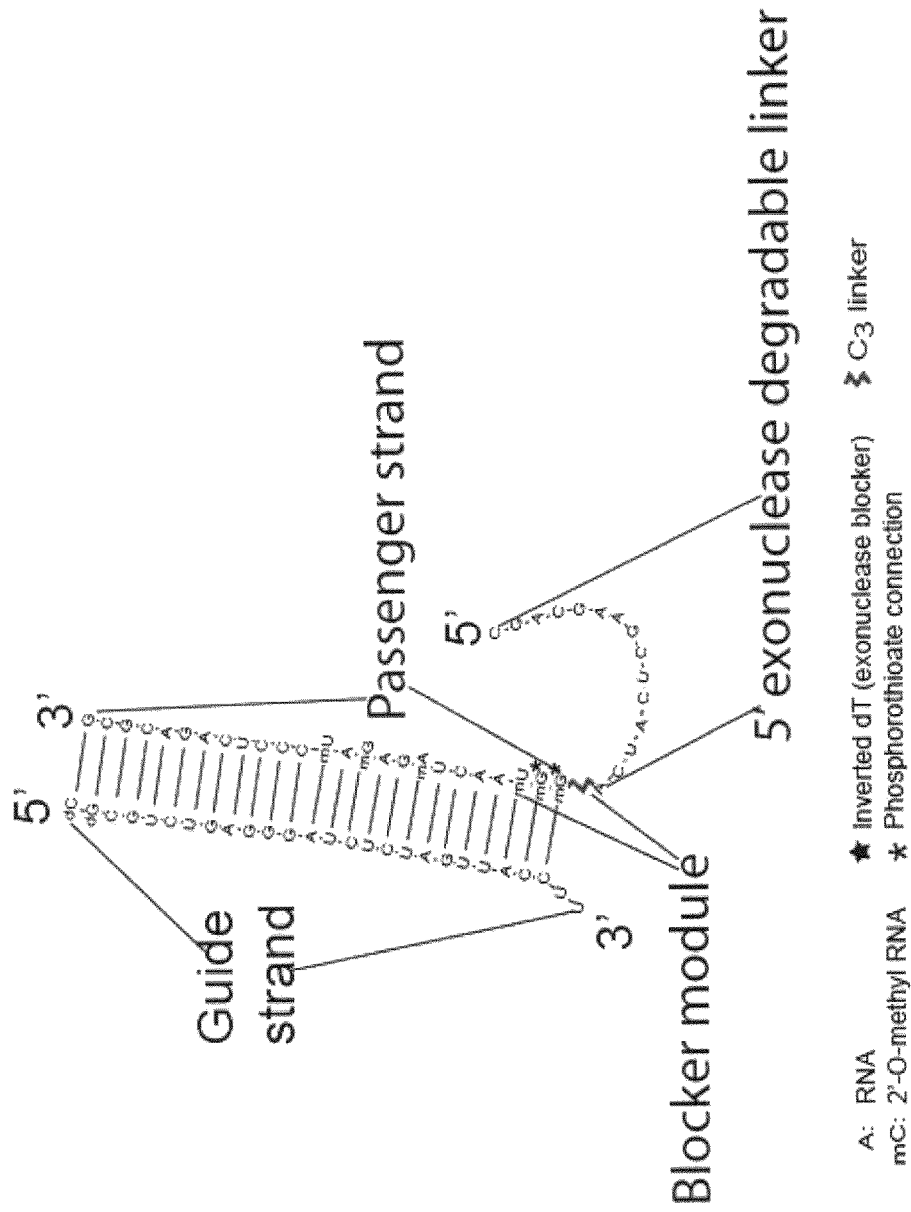
FIG. 2 shows a schematic representation of an exemplary exonuclease resistant duplex polynucleotide herein described. In particular, in the schematic illustration of FIG. 2, the blocker domain is indicated as "blocker module", the 5' overhang domain is formed by an all RNA sequence indicated with the wording "5' exonuclease degradable linker", and the guide strand and the passenger strand form a Dicer processable RNAi targeting domain.

Reference is made in this connection to the schematic illustration of FIG. 2, wherein an exemplary duplex polynucleotide comprising the exonuclease resistant polynucleotide herein described is shown. In particular in the schematic FIG. 2, the exonuclease resistant polynucleotide comprises a 5' overhang domain and is complementary bound to the guide strand as a passenger strand in a configuration wherein the non-nucleic acid polymer and the 5' overhang domain (indicated in FIG. 2 as 5' exonuclease degradable linker) is presented at the 5' end of the passenger domain. The non-nucleic acid polymer segment in the illustration of FIG. 2 is shown as a C3 linker attached to a phosphodiester sequence mUmGmG. More particularly, FIG. 2 shows an exemplary construct of a Dicer substrate siRNA where the blocker module connects an all RNA 5' extension to the 5' terminus of the passenger strand in a Dicer processable RNAi targeting domain. The exonuclease resistant polynucleotide shown in FIG. 2 has a formula (II) wherein A is 5'-CGACGAAGCU-CAUCA-3' (SEQ ID NO. 33) X is a C3 linker with flanking phosphodiester linkages, N1-N2-N3 are the 2'-O-methyl bases mG*mG*mU (SEQ ID NO. 48) where * denotes a phosphohorothioate linkage and A2 is 5'-AACU mA GA mG A mU CCCUCAGACGCG-3' (SEQ ID NO. 34).

In the illustration of FIG. 2 the attachment of a C3 linker to the sequence 5'-mG*mG*mU-3' (SEQ ID NO. 48) allows a phosphodiester linker to be present at the 5' linkage between the C3 linker and the RNA overhang and a second phosphodiester group between the C3 linker and the modified RNA. In the exonuclease resistant duplex polynucleotide of FIG. 2 the configuration of the C3 linker, the phosphorothioate linkages in the sequence attached to the C3 linker, and the 2'-O-methyl modifications, provide chemical properties that result in inhibition of proper binding of this segment with exoribonucleases, which on its turn inhibits cleavage at the C3 linker. In view of the configuration and composition herein described, the resulting degradation of the exoribonuclease resistant polynucleotide by a exoribonuclease is expected to result in a phosphate group presented on the 5' end of the exonuclease phosphate group on the C3 linker (A1 moiety removed), or at the 5' terminus of the sequence 5'P-mG*mG*mU-3' (SEQ ID NO. 48), where P indicates a 5' terminal phosphate (A1 and X moieties removed), which allows proper processing by dicer and/or an argonaute enzyme. Similarly, endonucleolytic cleavage of the linkage between the C3 linker and the A1 moiety would leave a segment 5'P-C3-mG*mG*mU-3' (SEQ ID NO. 48) and endonucleolytic cleavage of the linkage between the C3 linker and the A2 moiety, would also leave a segment 5'P-mG*mG*mU-3' (SEQ ID NO. 48). In both cases, P indicates a 5' terminal phosphate, which allows proper processing by dicer and/or an argonaute enzyme. Reference is made to the illustration of FIG. 1, the schematics show in particular Dicer's PAZ domain binding with the 3' terminus of the guide strand and the 5' terminus of the passenger strand to perform the proper processing In embodiments where the exonuclease resistant polynucleotide is nicked or otherwise modified to have at least one configuration allowing of the guide strand by dicer and/or an argonaute enzyme and at least one configuration minimizes processing of the guide strand by dicer and/or an argonaute enzyme, the processing by dicer and/or an argonaute enzyme occurs when the exonuclease resistant polynucleotide is in a configuration allowing said processing.

In some embodiments, in exonuclease resistant duplex polynucleotide, the exonuclease resistant polynucleotide comprises a 5' overhang region having modified nucleotides and/or phosphodiester linkages to control the degradation rate of the exonuclease resistant polynucleotide.

Reference is made to the schematic illustration of FIG. 3A to FIG. 3D, which show four exemplary exonuclease resistant duplex polynucleotides herein described.

In particular in the schematic illustration of FIGS. 3A to 3D, the exonuclease resistant polynucleotide B7 (SEQ ID NO. 25; SEQ ID NO. 26) (FIG. 3A), B10 (SEQ ID NO. 27; SEQ ID NO. 28) (FIG. 3B), B11 (SEQ ID NO. 29; SEQ ID NO. 30) (FIG. 3C) and B12 (SEQ ID NO. 31; SEQ ID NO. 32) (FIG. 3D) is complementary bound to the 3' end of the guide strand G3 as part of the passenger strand also comprising polynucleotide Ac4.

In particular in the illustrations of FIGS. 3A to 3D in the duplex polynucleotide the passenger strand is nicked in two passenger strand segments allowing the targeting domain duplex RNA to adopt a folded conformation and an unfolded conformation. In the unfolded conformation shown in the illustration of the FIG. 3A to FIG. 3D, (see also FIG. 1B of application U.S. Ser. No. 13/848,687 incorporated by reference in its entirety) the opposite ends of the duplex RNA are in a configuration allowing processing of the guide strand by dicer and/or an argonaute enzyme. In the folded conformation (shown for example in FIG. 1C of application U.S. Ser. No. 13/848,687 incorporated by reference in its entirety) opposite ends of the targeting domain duplex RNA are in a configuration which minimizes processing of the guide strand by dicer and/or an argonaute enzyme.

In the illustration of FIGS. 3A to 3D, the blocker domain of the exonuclease resistant polynucleotide is indicated as blocker module and attaches a 5' overhang comprised in a configuration allowing presentation of the 5' overhang at the 5' end. In the illustration of FIG. 3, the B7, B10, B11 and B12 (SEQ ID NO. 25; SEQ ID NO. 26; SEQ ID NO. 27; SEQ ID NO. 28; SEQ ID NO. 29; SEQ ID NO. 30; SEQ ID NO. 31; SEQ ID NO. 32) strands differ in the degree of phosphorothioation of the 5' extension connected to the blocker module. In particular, B7 (SEQ ID NO. 25; SEQ ID NO. 26) has an unmodified 5' extension with only RNA base and standard phosphodiester backbone connections. The B10 (SEQ ID NO. 27; SEQ ID NO. 28) differs from B7 (SEQ ID NO. 25; SEQ ID NO. 26) in that the 5' extension on B10 (SEQ ID NO. 27; SEQ ID NO. 28) has all phosphorothioate backbone connections. B10 (SEQ ID NO. 27; SEQ ID NO. 28) also has a 5' terminal hexaethyleneglycol and the connections flanking the C3 linker in the blocker module. In B11 (SEQ ID NO. 29; SEQ ID NO. 30), the phosphorothioate bonds present around the blocker module and flanking the C3 linker are changed back to phosphodiester connections. In B12 (SEQ ID NO. 31; SEQ ID NO. 32), most of the phosphorothioate backbone connections in the 5' extension have been removed, leaving only three such connections at the 5' terminus.

Example 11 and Example 12 show experimental results that indicated that a lower number of phosphorothioates in the overhang is expected decrease nuclease resistance further compared to the configuration in FIG. 3C. Thus, the configuration in FIG. 3A is shown to have an RNAi activity resulting in a 50% or greater inhibition of protein production as detected by dual luciferase assays, as is shown in Example 11 and a large amount of Dicer product as shown in Example 12. The configuration in FIG. 3B has an RNAi activity and Dicer processing lower than the ones of the exonuclease resistant duplex polynucleotide shown in FIG. 3A. The RNAi activity of the configuration in FIG. 3C is significantly higher than that of the configuration shown in FIG. 3B. The RNAi activity of the configuration in FIG. 3D is increased with respect to the RNAi activity of the example configuration in FIG. 3C.

FIG. 4 shows a schematic representation of exemplary exonuclease resistant duplex polynucleotides wherein the blocker domain attaches a 5' overhang domain. In particular, FIG. 4 illustrates exemplary constructs with a blocker module connecting a 5' oligonucleotide extension to the targeting domain. In the illustration of FIG. 4 the targeting domain is composed of the guide strand, G2 (SEQ ID NO. 20), and its base paired passenger strands. In all four examples shown in FIG. 4, the Ac4 passenger strand is used. In these examples, the guide strand G2 (SEQ ID NO. 20) differs from the guide strand G3 (SEQ ID NO. 21), in FIG. 3 because the two LNA bases in G3 (SEQ ID NO. 21) are replaced with normal RNA bases.

Also in this case similarly to what already noted for the exonuclease resistant duplex of FIG. 3, experimental results (Example 11 and Example 12) indicate that also for the exemplary exonuclease resistant duplex of FIG. 4 a lower number of phosphorothioates in the overhang is expected to decrease nuclease resistance further compared to the configuration in FIG. 3C (see examples section).

In some embodiments, the exonuclease resistant duplex polynucleotide is a targeting domain. A "targeting domain" as used herein indicates a domain of a polynucleotide associated with the function of binding or reacting with a predetermined target within a biological environment and in particular within a cell.

The term "target" as used herein indicates an analyte of interest. The term "analyte" refers to a substance, compound, moiety, or component whose presence or absence in a sample is to be detected. Analytes include but are not limited to biomolecules and in particular biomarkers. The term "biomolecule" as used herein indicates a substance, compound or component associated with a biological environment including but not limited to sugars, amino acids, peptides, proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The "biological environment" refers to any biological setting, including, for example, ecosystems, orders, families, genera, species, subspecies, organisms, tissues, cells, viruses, organelles, cellular substructures, prions, and samples of biological origin.

Exemplary targeting domains in the sense of the present disclosure comprise siRNA, saRNA, microRNA and additional polynucleotides identifiable by a skilled person.

Figure 7:
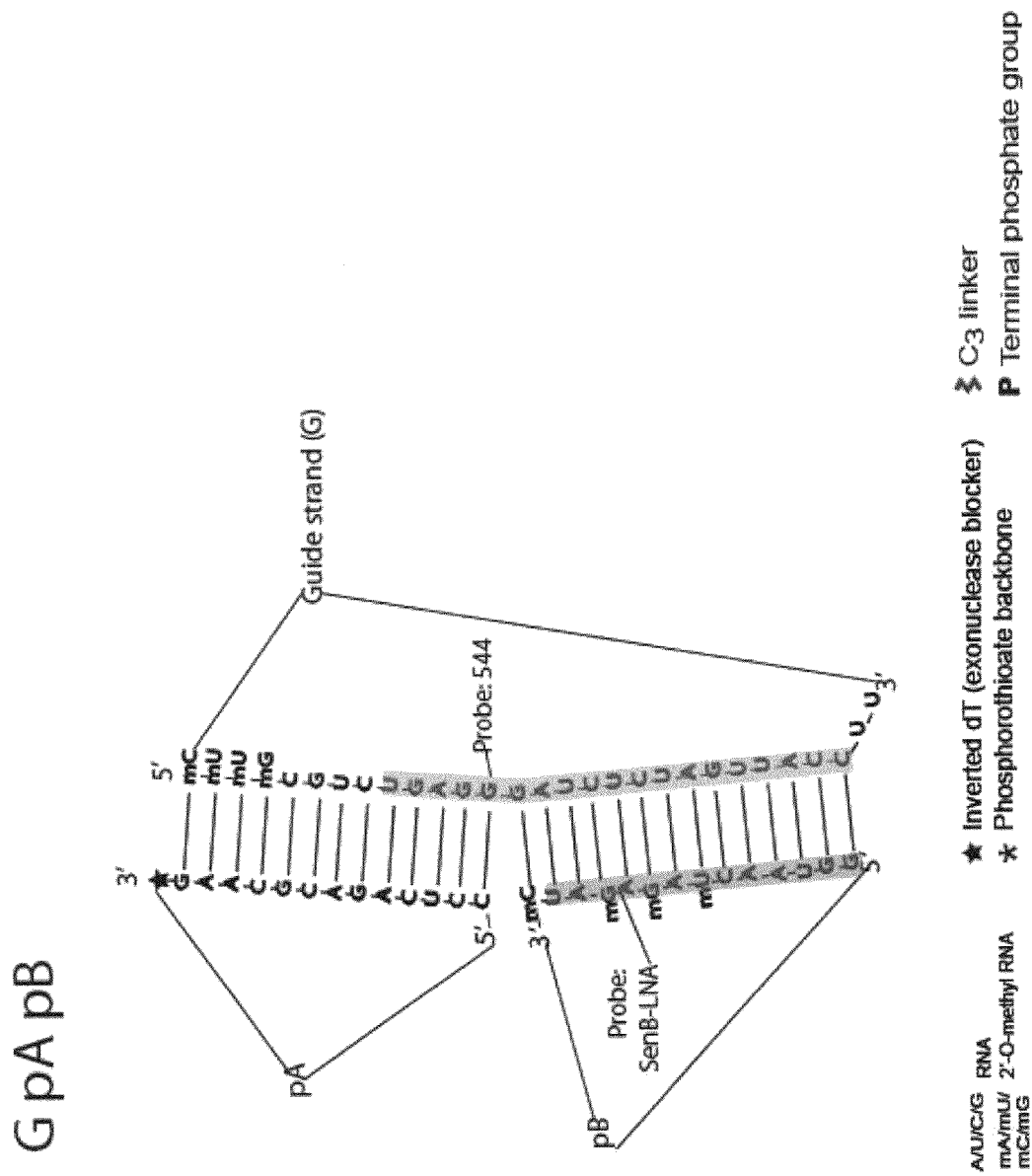
FIG. 7 shows a schematic representation of a duplex polynucleotide that does not include an exonuclease resistant polynucleotide herein described and that can used as a positive control for experiments testing functionality if the exonuclease blocker domain. The positions probed by Northern blot probes 544 and SenB-LNA are shown highlighted in gray.

Reference is made to the exemplary illustration of FIG. 7 which shows a schematic representation of a duplex used as a positive control for experiments testing the exonucleases blocker domain. In particular FIG. 7 illustrates a construct (G pA pB (SEQ ID NO. 1; SEQ ID NO. 13; SEQ ID NO. 14) used as a positive control for experiments testing the exonucleases blocker module. More particularly the construct of FIG. 7 is a Dicer substrate siRNA composed of G, a 27 nt long guide strand, pA, a 13 nt long passenger strand, and pB, a 14 nt long passenger strand. The construct of FIG. 7 does not have a blocker domain.

Figure 5:
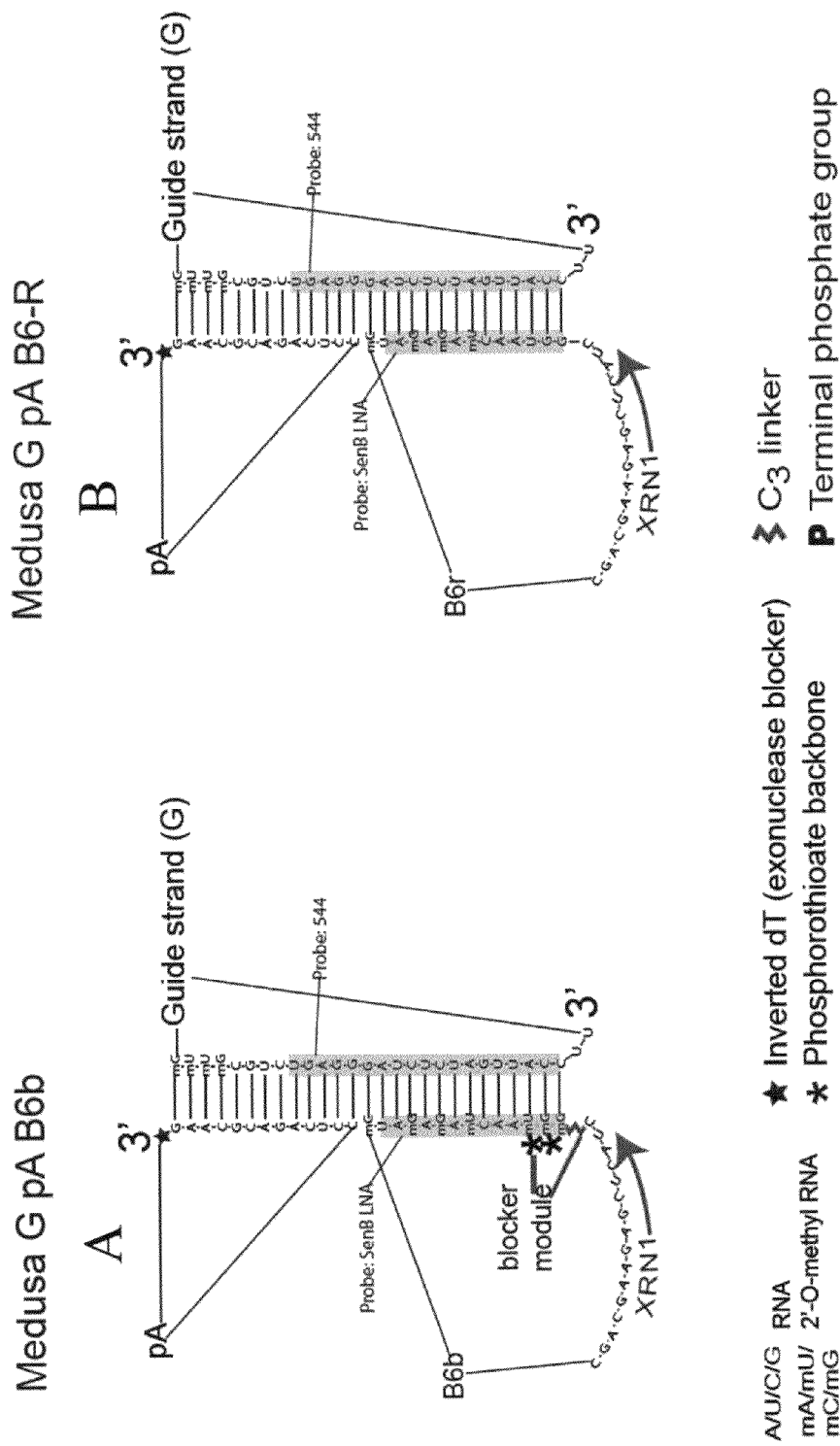
FIG. 5 shows a schematic representation of an exemplary exonuclease resistant duplex polynucleotides herein described (FIG. 5A) in comparison with a duplex polynucleotide not including a blocker domain (FIG. 5B). The positions probed by Northern blot probes 544 and SenB-LNA are shown highlighted in gray. In particular.

Reference is made to the exemplary illustration of FIG. 5 which shows a schematic representation of two variants Dicer substrate siRNA used to test the functioning of the exonucleases blocker domain. In particular, FIG. 5 illustrates two variants of the (G pA pB) Dicer substrate siRNA used to test the functioning of the exonucleases blocker module in experiments. G pA B6b (SEQ ID NO. 1; SEQ ID NO. 13; SEQ ID NO. 14) has a 16 nucleotide long 5' RNA extension attached to the 5' of the Dicer substrate siRNA's passenger side via a blocker domain. G pA B6-R (SEQ ID NO. 1; SEQ ID NO. 13; SEQ ID NO. 19) has the identical extension attached to the same position, but without the blocker domain. In other words, the extension is attached via a normal phosphodiester linkage to unmodified RNA bases.

Figure 6:
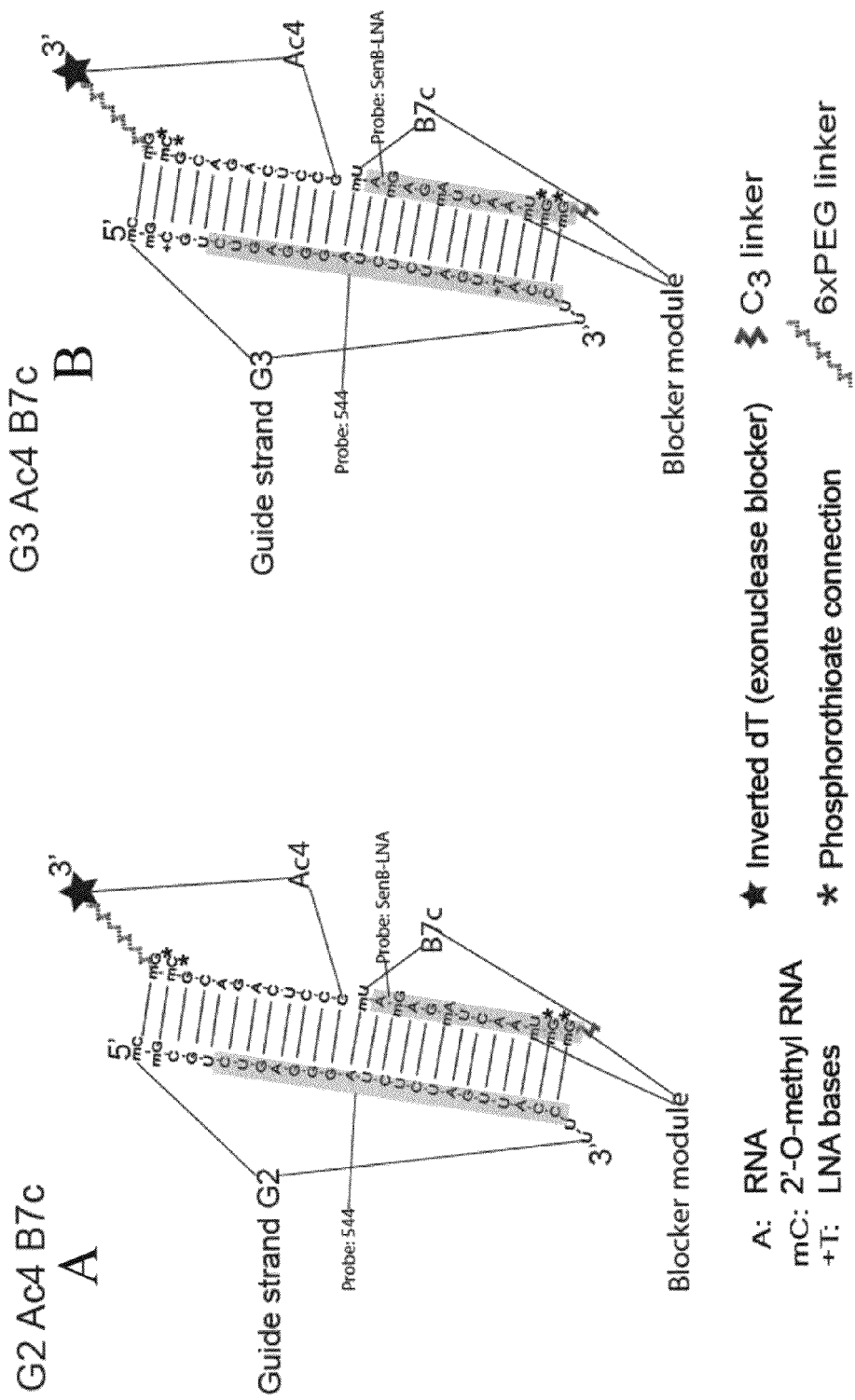
FIG. 6 shows a schematic representation of two exemplary exonuclease resistant duplex polynucleotides herein described. The positions probed by Northern blot probes 544 and SenB-LNA are shown highlighted in gray. In particular.

FIG. 6 shows a schematic representation of two exemplary variants that act as Dicer substrate siRNA. FIG. 6A contains a blocking domain at the 5' base of the passenger strand. In FIG. 6B is the same except that the G3 strand contains two LNA modified bases.

In particular, FIG. 6 illustrates two exemplary variants (G2 Ac4 B7c (SEQ ID NO. 20; SEQ ID NO. 24; SEQ ID NO. 38) and G3 Ac4 B7c (SEQ ID NO. 23; SEQ ID NO. 24; SEQ ID NO. 38) that act as Dicer substrate siRNA. An exonucleases blocking module is at the 5' base of the passenger strand B7c on both examples. As synthesized, the 5' C3 linker is terminated with an OH, but this is converted to a terminal phosphate group by cellular kinases. The only difference between the G2 and G3 strands is the presence of two LNA modified bases on the G3 strand. In G2 these two bases are normal RNA.

Results of tests performed with the exonuclease resistant duplex polynucleotide of FIG. 6 in which the non-nucleic acid linear polymer is a C3 linker, support the conclusion that the end-to-end distance for the fully extended non nucleic acid liner polymer can be about 0.5 nm (which is the end-to end distance of the tested C3 linker), and can be higher and up to about 1.00 nm or lower down to 0.10 nm, including end-to-end distances of about 0.4 nm, about 0.5 nm, about 0.65, about 0.8 nm, about 0.9 nm and about 1 nm (see Example 11 and Example 12) as long as the terminal phosphate can fit into the PAZ domain binding pocket as will be understood by a skilled person. Results of tests performed with the exonuclease resistant duplex polynucleotide of FIG. 6 also support the conclusion that the persistence length of the non-nucleic acid polymer can be 0.38 nm (persistence length of the tested C3 linker) but can be higher up to about 0.5 nm or lower down to 0.1 (see Example 11 and Example 12) as long as the terminal phosphate can fit into the PAZ domain binding pocket as will be understood by a skilled person.

In embodiments herein described, the non-nucleic acid linear polymer has a persistence length of the polymer up to about 0.5 nm. In particular in embodiments herein described the persistence length can be about 0.38 nm. (see Examples section and in particular Example 11).

In several embodiments, exonuclease resistant duplex RNA and in particular exonuclease resistant targeting domain herein described can be comprised in molecular construct together with an additional moiety. In particular, in embodiments herein described, the molecular construct comprising the exonuclease resistant duplex polynucleotide herein described has at least one configuration of the exonuclease resistant molecular construct in which the 5' passenger strand of the exonuclease resistant duplex polynucleotide is presented for binding to an exonuclease.

Figure 14:
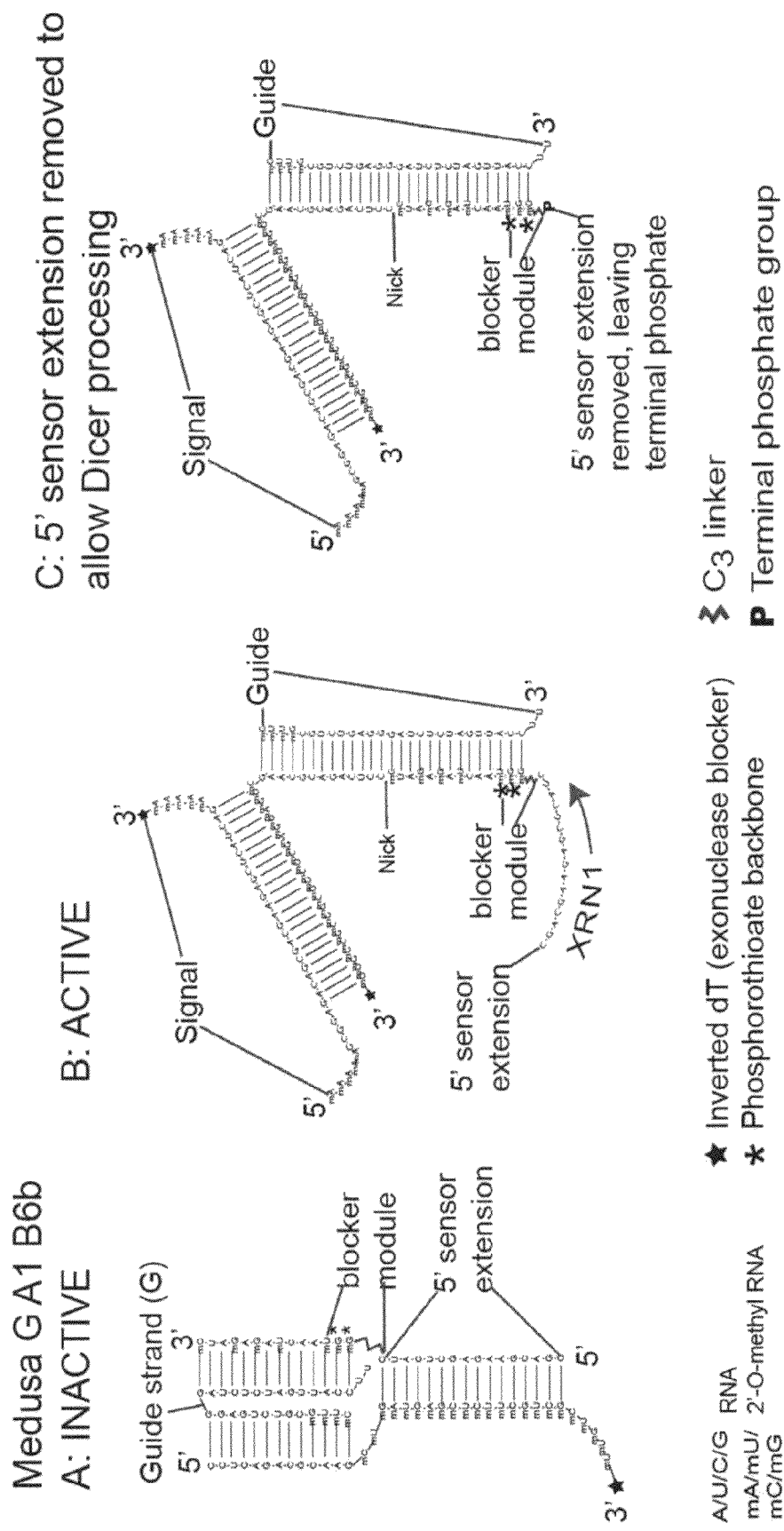
FIG. 14 shows a schematic representation of different configuration of exemplary molecular construct Medusa GA1B6b (SEQ ID NO. 1; SEQ ID NO. 3; SEQ ID NO. 17; SEQ ID NO. 18) comprising the exemplary exonuclease resistant polynucleotide B6b (SEQ ID NO. 17; SEQ ID NO. 18). In particular, in the illustration of FIG. 14, the folded conformation (FIG. 14A) and an unfolded conformation (FIG. 14B) are shown wherein the switching from one conformation to another is performed through displacement of the signal binding portion following binding of a signal polynucleotide.
Figure 18:
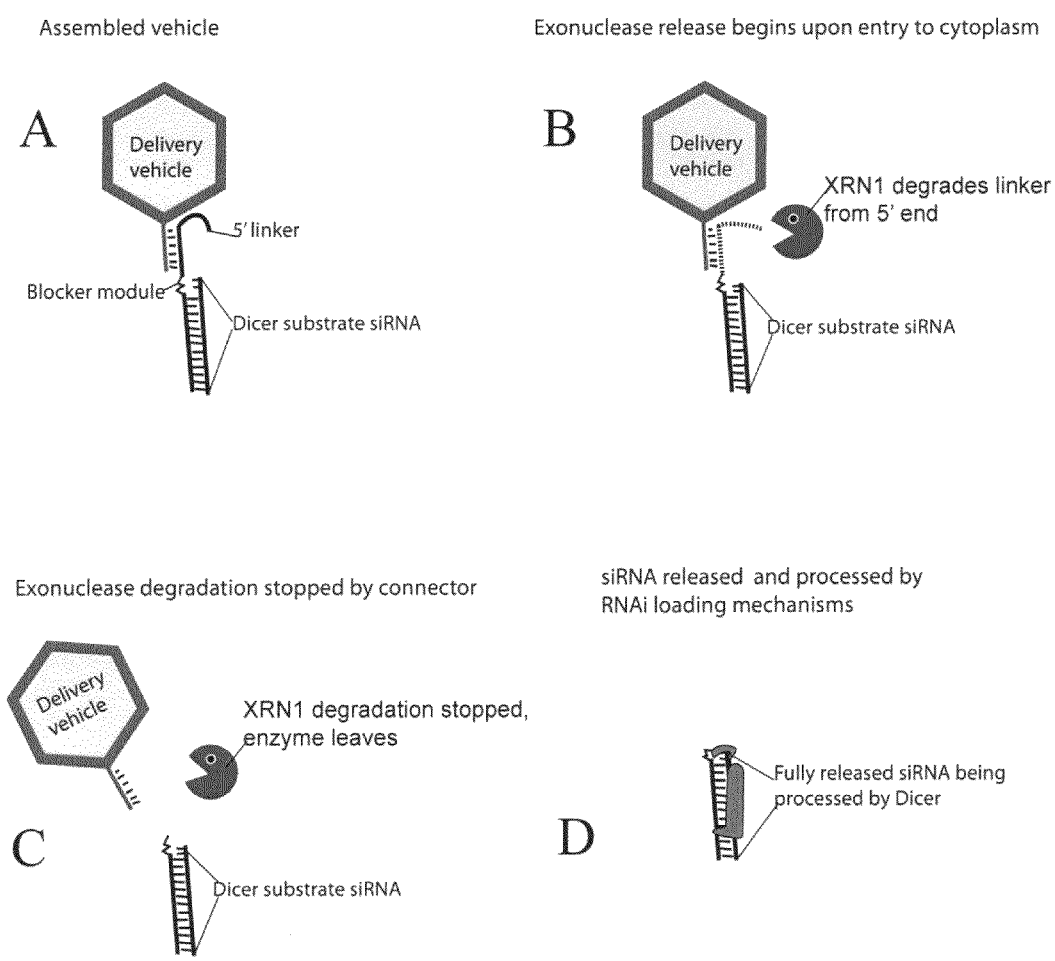
FIG. 18 shows a schematic representation of an exemplary molecular construct comprising an exonuclease resistant duplex polynucleotide herein described attached to a vehicle moiety.

Reference is made to the illustration of FIG. 14 and FIG. 18 showing different configuration in which the 5' end of the exonuclease resistant polynucleotide is presented for binding to an exonuclease (see in particular, FIG. 14B and FIG. 18A). In particular, the exemplary construct of FIG. 14B is alternative to a configuration wherein the 5' end of the exonuclease resistant polynucleotide is not presented for binding (FIG. 14A) which can be used for transporting a targeting domain within a desired exonuclease environment.

In particular, the exonuclease resistant polynucleotides herein described can be used in constructs in many embodiments for enzyme assisted molecular delivery. The term "molecular delivery" as used herein indicated any process by which controlled activation of molecular complexes regulates the release of a chemical compound for various purposes.

The term "enzyme-assisted" as used herein is defined to mean any chemical process where a protein or other chemical entity is used to catalyze or increase the rate of a chemical reaction. The protein used for this purpose can include, but is not limited to, chains of amino acids (natural or unnatural), that may or may not contain other chemical variations and can have a defined secondary structure. The chemical reaction can include, but is not limited to, reactions of RNA or portions of RNA, DNA or portions of DNA, and/or any nucleotide or derivative thereof. Typically, enzymes catalyze reactions through binding to specific target molecular portions usually indicated as binding sites.

In particular in some embodiments described herein and in U.S. application Ser. No. 13/848,687 incorporated by reference in its entirety, constructs are described that can be used for molecular delivery assisted by endonuclease or exonuclease.

The term "endonuclease" as used herein, refers to a type of enzyme that can cleave a phosphodiester bond within a polynucleotide chain. There are a small number of significant classes of endonucleases that can cleave only at the specific nucleotide sequences (such as the restriction endonucleases which are vital in biotechnology). At the extreme ends of a sequence there are restriction endonucleases, usually called restriction enzymes. These are endonucleases from eubacteria and archea that recognize a specific DNA sequence. The nucleotide sequence recognized for cleavage by a restriction enzyme is called the restriction site. A restriction site can be a palindromic sequence of about four to six nucleotides long. Restriction endonucleases can cleave the DNA strand unevenly, leaving complementary single-stranded ends. These ends can reconnect through hybridization and are termed "sticky ends." Once paired, the phosphodiester bonds of the fragments can be joined by DNA ligase. DNA fragments cleaved by the same endonuclease can be joined together regardless of DNA origin. Such DNA is called "recombinant DNA," which is DNA formed by the joining of genes into new combinations.

In some embodiments, endonuclease assisted molecular delivery can be performed by RNAase assisted molecular delivery. The term "RNAse H" as used herein refers to a non-specific endonuclease that is able to catalyze RNA cleavage via a hydrolytic mechanism. In particular RNase H's ribonuclease activity cleaves a 3'-O—P bond of RNA in a DNA:RNA duplex to produce 3' hydroxyl and 5' phosphate terminated products. RNAase H cleaves the RNA strand in DNA:RNA duplexes. The minimal substrate for RNAse H cleavage activity is usually a 5 to 7 base pair long stretch of duplex DNA:RNA. As used herein the term "RNAase H" comprises any enzymes whether naturally occurring or synthetically modified including any enzyme modified in one or more residues which substantially retain an endonucleasic activity such as the one herein described. Naturally occurring RNAase H enzyme which are members of the RNAse H family can be found in nearly all organisms, from archaea to prokaryote and eukaryote are identifiable by a skilled person. In human cells, RNAse H commonly cleaves the RNA sequence of a DNA: RNA duplex at a position that is 5 nucleotides from the 5' end of the RNA sequence forming the duplex. If the duplex is longer than 7 base pairs, RNAse H can cleave at additional positions to the 3' of the first cleavage site. The mammalian RNAse H class enzymes cleave the RNA portion of DNA:RNA duplexes. RNAse H class enzymes constitute the dominant mechanism of activity for many antisense oligonucleotide drugs. RNAse H can be typically active both in the cytoplasm and the nucleus.

In several embodiments, wherein the enzyme-assisted molecular delivery herein described is assisted by an exonuclease, the enzyme assisted molecular delivery can be an XRN1 assisted molecular delivery. In several embodiments, the enzyme-assisted molecular delivery herein described is an XRN1 assisted molecular delivery. The term "XRN1" as used herein refers to an exoribonuclease enzyme that is capable of degrading ribopolynucleotides by removing terminal nucleotides from the 5' terminus of the ribopolynucleotide. As used herein the term "XRN1" comprises any enzymes whether naturally occurring or synthetically modified including any enzyme modified in one or more residues which substantially retain an exoribonuclease activity such as the one herein described. Naturally occurring XRN1 enzymes which are members of the XRN1 family can be found in many organisms including yeast, nematode, fruit fly, and human. XRN1 is also referred as Pacman, KEM1, SEP1, DST2, RAR5 SKI1 and DST2 to one skilled in the art.

In particular, in some embodiments, constructs using the exonuclease resistant polynucleotide herein described can be signal activatable constructs.

The term "signal activatable construct" as used herein indicates a molecular complex that can have more than one conformation, and at least one of the conformations results from the binding of a signal molecule to the molecular complex. Typically, the conformation associated to the binding of a signal molecule to the molecular complex is also associated to a chemical and/or biological activity that characterizes the conformation as active with respect to the identified activity. Accordingly, signal activatable constructs herein described can have at least one active conformation and at least one inactive conformation with respect to the enzymatic activity of the enzyme assisted molecular delivery. Switching between an inactive conformation to an active conformation is triggered by binding of the signal molecule to the construct.

Signal activatable constructs and related components herein described comprise one or more polynucleotides. In several embodiments, the enzyme-assisted molecular delivery herein described is an RNAase H assisted molecular delivery.

In particular, in some embodiments, the enzyme assisted molecular delivery is directed to release a targeting domain with a biological environment and in particular within a cell, and the release of the targeting domain can be catalyzed by XRN1 or RNAase H in combination with dicer and/or an argonaute enzyme.

Reference is made to the schematic illustration of FIGS. 1 to 37 of U.S. application Ser. No. 13/848,687 incorporated by reference in its entirety, which shows an exemplary targeting domain which can be formed by an exonuclease resistant duplex polynucleotide herein described.

Reference is made in this connection to the exemplary illustration of FIGS. 13, 14, 16 and 17 schematically showing that the linkage between the two opposite ends of a targeting domain comprising an exonuclease resistant duplex polynucleotide of the disclosure provide a configuration of the opposite ends such that those ends are at an angle of about 10° between each other. Additional suitable configurations of the opposite ends suitable for a folded conformation of the targeting domain comprise angles up to about 90° as will be understood by a skilled person. Calculation of the angle between the opposite ends of the targeting domain can be performed by estimating the length of a duplex segment to be approximately 0.34 nm per base-pair, and the maximum length of an unstructured polynucleotide of less than or equal to 20 nucleotides to be approximately 0.5 nm per nucleotide, and then using trigonometry to calculate the maximum possible angle assuming the estimated duplex lengths and the maximum unstructured polynucleotide length. If the different segments are linked via a non-polynucleotide linker, such as a $C_3$ or a polyethylene glycol linker, then for a short linker the one can use the maximum possible length of the linker as calculated from the length of the constituent molecular bonds and angles to calculate the maximum angle via trigonometry. For unstructured polynucleotide linkers longer than 20 nucleotides or polymer linkers longer than 20 polymer units, the average end to end distance can also be calculated using polymer physics and an approximate range of motion can be established by considering the energetic penalty of stretching the unstructured polymer beyond its average end to end distance. In these cases the bending angle is estimated to remain below the maximum angle of 90 degrees with at least 90% probability. In a solution targeting domains herein described are expected to change in accordance with temperature, length of linkage between the opposite ends and additional parameters identifiable by a skilled person.

In signal activatable constructs herein described, the relative thermodynamic stability of the various segments of the locking sensor is configured to trigger a switch from an inactive conformation to an active conformation upon binding of a signal molecule. Accordingly, switching from a conformation to another can be controlled based on a comparison of the free energy of the related systems. The term "free energy" as used herein is defined to mean a thermodynamic quantity that can be used to determine the spontaneity of a chemical reaction of transformation. Where the chemical transformation is the conversion of one polynucleotide conformation to another polynucleotide conformation, comparing the free energies of the polynucleotide conformations can be used to indicate which conformation will predominate. For example, free energy can be used to estimate thermodynamic stability of polynucleotide double-strand duplex and/or polynucleotide secondary structure that is more thermodynamically stable, but it is not limited to this use. Free energy can be estimated by computational methods, among other means.

In several embodiments, the inactivated conformation of the signal activatable constructs, the melting temperature of double-stranded duplex formed by the activation segment and the displacement segment is at least about 25° C. so that the double-stranded duplex formed by the activation segment and the displacement segment is more thermodynamically stable formed by different portions of the activation segment, activation segment and toehold segment at room temperature. This is to ensure that in the absence of the signal molecule, the construct adopt the inactive conformation, with the activation segment complementarily binds to the displacement segment, rather than associating with the activation segment. The strand melting temperature (Tm) of the double-stranded duplex formed by the protection segment and the displacement segment can be experimentally tested or measured (see e.g. Example 8). Accordingly, the experiment to characterize the strand displacement reaction as described in Example 9 can use a construct comprising both the sensor domain and the targeting domain. In particular, the fluorophore quencher pair can be placed at multiple positions along the duplex formed by the displacement segment and the second segment or the displacement segment and the protection segment to allow assessment of strand displacement. Thermodynamic stability is affected by various parameters such as composition of the specific solution, pressure, temperatures as well as other conditions identifiable by a skilled person.

For example for signal activatable constructs such as the ones exemplified in FIG. 14, in configurations of the activation segment, toehold segment and displacement segment in an inactive conformation suitable to transform to an active conformation in presence of the complementary signal polynucleotide, are such that the binding of the of the complementary signal polynucleotide to the toehold segment and the displacement segment has a melting temperature (Tm) of at least about 25° C. In some of those embodiments, sequence length and composition of toehold segment and displacement segment is such that binding of the signal polynucleotide to the toehold segment and displacement segment is at least as stable as the binding between the activation segment and the displacement segment to minimize partial displacement of the activation segment from the displacement segment upon binding of the signal polynucleotide.

Starting with an initial duplex length, a person skilled in the art can experimentally test for thermodynamic stability, nuclease resistance and PKR activation using live cells or cell lysates via methods such as Northern blotting, immunoprecipitation, or FRET assays. If the duplex is thermodynamically unstable in the cellular environment, the duplex length can be increased. If endonuclease cleavage of the duplex occurs, the duplex length can be decreased. If PKR activation occurs, the duplex length can be decreased.

In several embodiments, modified bases can be used throughout the duplex polynucleotide and constructs herein described to increase thermodynamic stability, and nuclease resistance, decrease toxicity, and/or increase specificity. Suitable modifications comprise, for example, 2'-O-methyls, introduction of a non-nucleic acid linker and/or an unstructured RNA segment, and terminal modifications. In particular, 2'-O-methyls can be used in particular in displacement segment (6) and toehold segment (7) to increase thermodynamic stability and prevent unwinding by RNA binding proteins. In addition, non-nucleic acid linkers can be used to confer desirable properties to the construct and/or portions thereof. Exemplary non nucleic acid linkers suitable to be used herein comprise C3 linkers and tri and hexa-ethylene glycol linkers as well as any biocompatible polymeric linker group with no nonspecific association with DNA. In particular, molecular constructs herein described can comprise A linker group with a lower persistence length than nucleic acids (e.g.: C3, polyethylene glycol) to increase flexibility at the attachment point. Such a linker group can reduce interference of long overhangs against Dicer binding. Molecular constructs herein described can also comprise a non-nucleic acid linker group to interfere with degradation by exonucleases and endonucleases, including RNAi pathway enzymes. Molecular constructs herein described can further comprise an unstructured RNA segment to have non-canonical interactions with other RNA segments, leading to unpredictable tertiary conformations. Molecular constructs herein described can further comprise a terminal modification that can prevent binding of the PAZ domain of Dicer, as well as other terminal modifications useful for preventing Dicer binding, such an Inverted dT Fluorescein and other groups incompatible with the PAZ domain listed from last patent.

Various other configurations of the activatable constructs herein described can be identified by a skilled person upon reading of the present disclosure.

Figure 12:
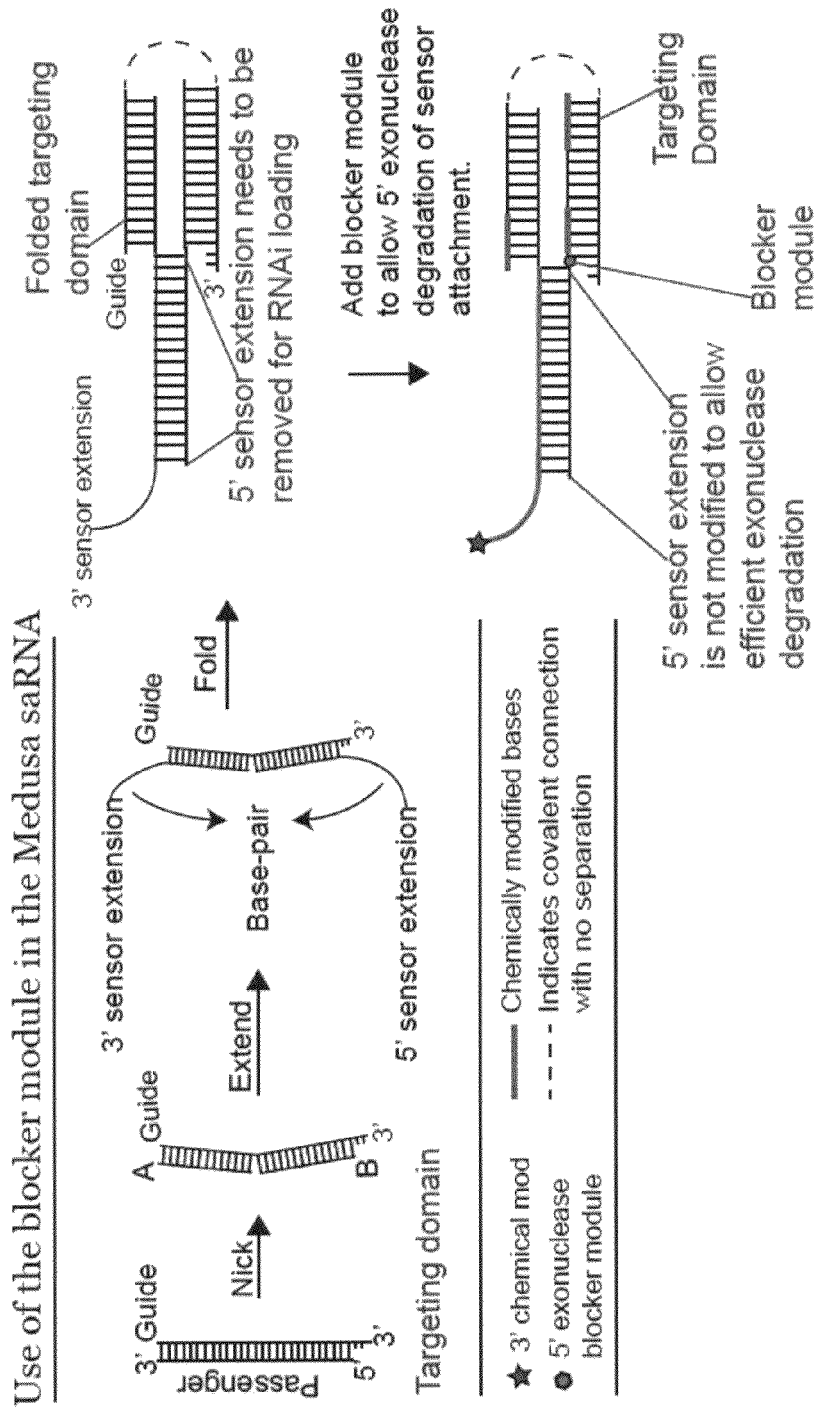
FIG. 12 shows a schematic representation of an exemplary attachment of an exemplary duplex polynucleotide (formed by targeting domain) to a vehicle moiety to provide a molecular construct.

A schematic representation of an overall method to provide a targeting domain and an activable construct herein described is illustrated in FIG. 12. In particular the exemplary construct of FIG. 12 inactivates in human cells as shown in Examples 2 and 5 of U.S. application Ser. No. 13/848,687 incorporated by reference in its entirety and has a folding with small energetic cost which results in good thermodynamic stability for the folded state as shown in Example 5 of U.S. application Ser. No. 13/848,687. In the illustration of FIG. 14, the construct of FIG. 12 is shown with an indication of possible chemical modifications directed to increase stability of the construct and activation efficiency following binding of an RNA activating signal to the toehold segment. In particular, 2'-O-methyl nucleotides in the indicated positions increase thermodynamic stability and nuclease resistance for the INACTIVE state and increase stability of toehold binding to the signal polynucleotide. The 3' terminus of the signal binding toehold has and inverted dT modification to increase exonucleases resistance and prevent spurious binding to the PAZ domain of Dicer. The C3 linker in the indicated position minimizes interference of the 5' overhang from interfering with Dicer processing in the ACTIVE state, as shown in example 4. The C3 linker, in conjunction with adjacent 2'-O-methyl and phosphorothioate modifications on the same strand, prevents 5' exonucleases degradation from proceeding beyond the overhang into the targeting domain.

In the activation: displacement duplex, it is preferred that thermodynamically stabilizing modifications are made to the side that binds the signal polynucleotide. This ensures the thermodynamic and kinetic favorability of binding to the correct signal polynucleotide.

Figure 15:
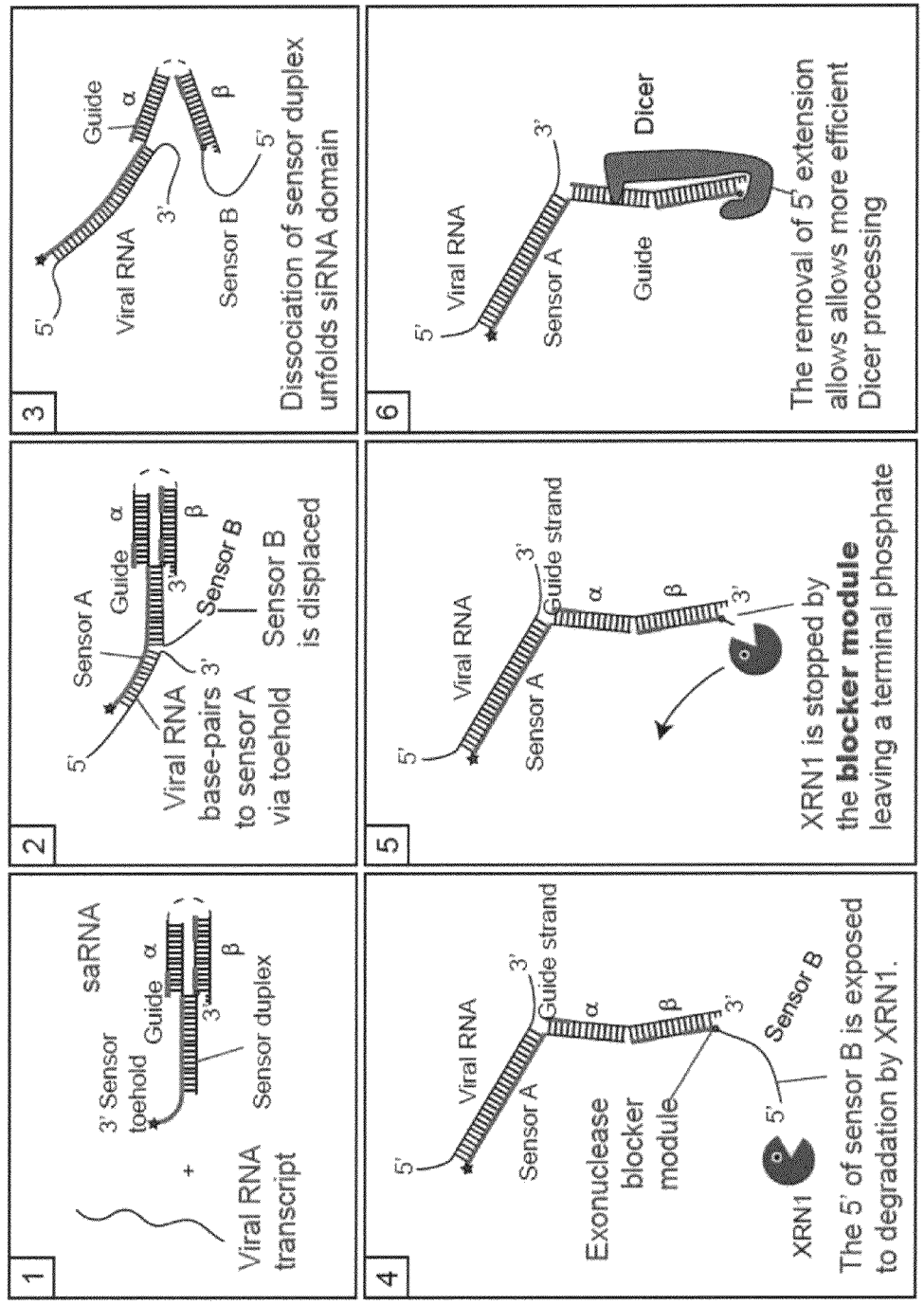
FIG. 15 shows a schematic representation of an exemplary method to release an exemplary targeting domain from the exemplary molecular construct of FIG. 12 and FIG. 14.

FIG. 15 is a schematic representation of the XRN1 release mechanism as described in several embodiments herein which can be used for the release of cargo by controlled exonuclease degradation using oligonucleotide formulations described in several embodiments.

For example, in addition to having different configuration of the constructs, modifications can be performed to increase the stability and/or the efficient processing of the activated construct through RNAai activity. In particular additional process steps to increase RNAi activity can comprise reduction of long 5' and 3' overhangs near the PAZ binding domain of the RNAi substrate (3' end of the Guide strand) inhibit Dicer processing as will be understood by a skilled person. Additional suitable approaches to improve RNAi activity on the targeting domain comprise: i) increase the flexibility of the linker between the overhang and the RNAi substrate by using a non-nucleic acid linker; ii) allowing an exonuclease to degrade the overhang and using chemical modifications to stop the exonuclease at a specific point; and/or iv) creating an endonuclease domain (e.g., a RNAse H domain) to allow clipping of the overhang by an endonuclease.

Figure 16:
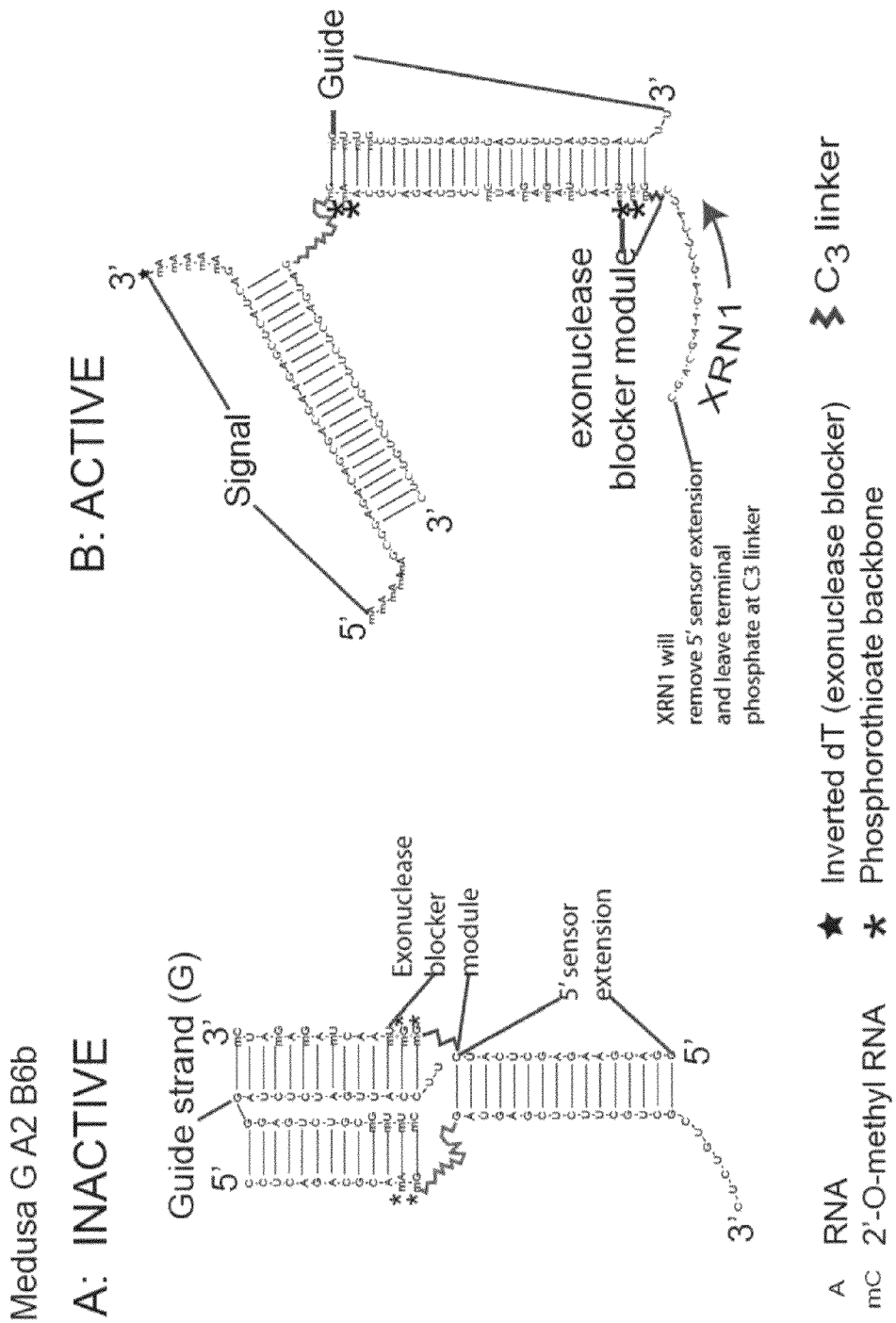
FIG. 16 shows a schematic illustration of an exemplary molecular construct, Medusa G A2 B6b (SEQ ID NO. 1; SEQ ID NO. 4; SEQ ID NO. 5; SEQ ID NO. 17; SEQ ID NO. 18) which comprises the exemplary exonuclease resistant polynucleotide B6b (SEQ ID NO. 17; SEQ ID NO. 18). In particular.
Figure 17:
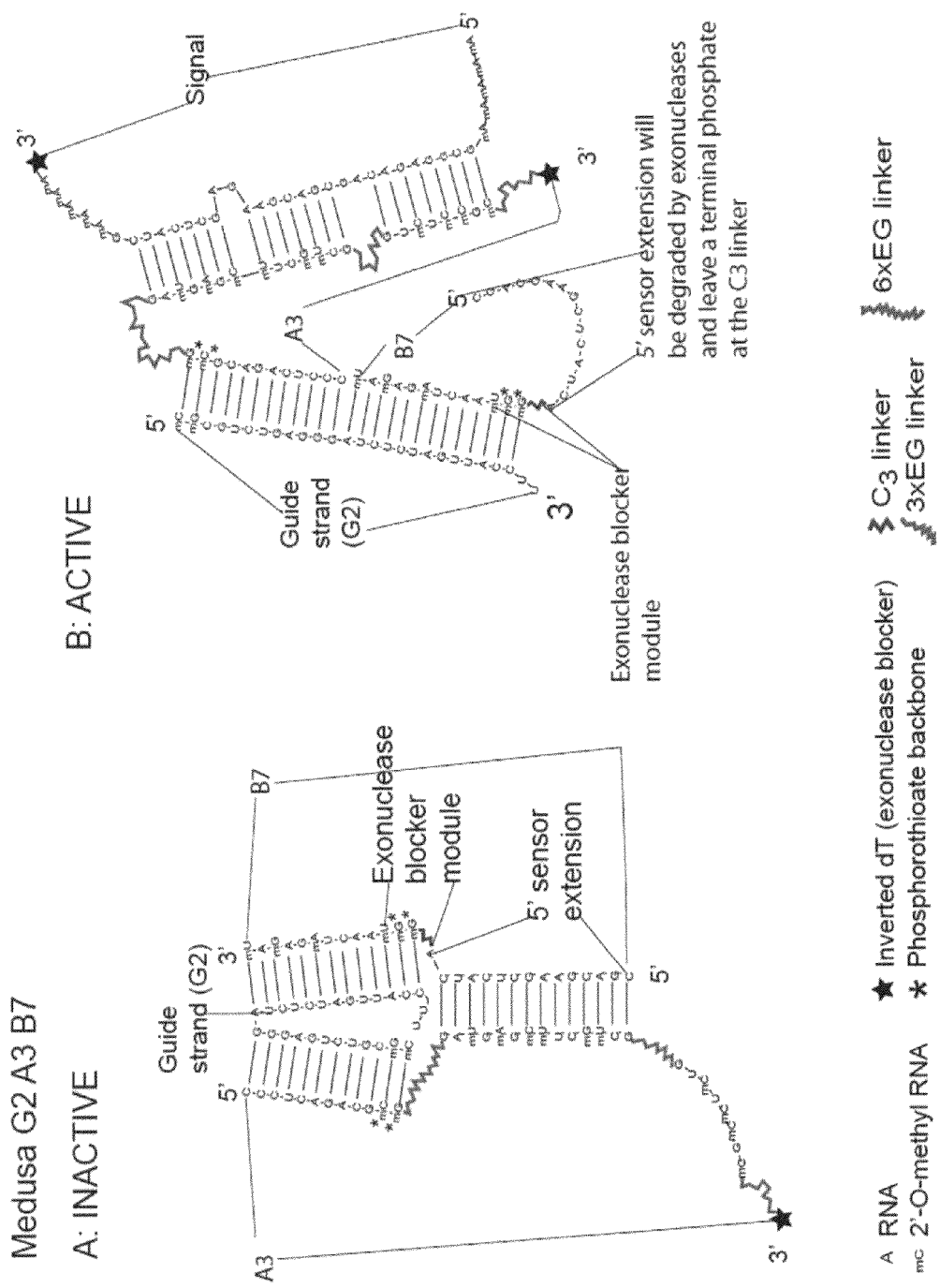
FIG. 17 shows a schematic illustration of an exemplary molecular complex, Medusa G2 A3 B7 (SEQ ID NO. 20; SEQ ID NO. 8; SEQ ID NO. 9; SEQ ID NO. 25; SEQ ID NO. 26) which comprises the exemplary exonuclease resistant polynucleotide B7 (SEQ ID NO. 25; SEQ ID NO. 26). In particular.

The illustration of FIGS. 13, 14, 16, and 17 show possible constructs modified to increase efficiency of RNAai activity following switch of an XRN1 based construct from an inactive conformation (OFF conformation) to an active conformation (ON conformation). In particular, FIG. 16 shows an XRN1 activated version with reduced turn OFF. FIG. 16 shows XRN1 degradation of the 5' overhang in the active conformation, which contains a C3 linker, a phosphorothioate backbone, and 2'O methyl bases. FIG. 17 shows an XRN1 activated version with ON/OFF activity ratio improved by adding features to reduce PKR recognition resulting in a less stable duplex RNA.

In some embodiments, in the constructs herein described the different segment can comprise a DNA portion and an RNA portion, the DNA portion of the activation segment complementary to the RNA portion of the activation segment. In those embodiments, when the displacement segment is displaced from the activation segment the DNA portion of the activation segment complementarily binds the RNA portion of the activation segment to provide an RNAase H binding site presented for binding.

In the targeting domain, the 5' of the guide strand is modified with 2'-O-methyl bases to increase thermodynamic stability and nuclease resistance. The rest of the guide strand is unmodified to avoid interference with RISC functioning. The passenger side can contain interspersed 2'-O-methyl bases to increase thermodynamic stability.

In the sensor, the side of the sensor which binds to the activation signal is entirely 2'-O-methyl to increase nuclease resistance, thermodynamic stability, and avoid destabilization by RNA chaperone proteins. The 3' terminus of the sensor toehold has an inverted dT modification to inhibit binding of Dicer to the sensor stem. The sensor stem is also kept below 19 base pairs to avoid Dicer processing. The 5' extension of the sensor stem is responsible for formation of the RNAse H binding domain. In addition to the DNA bases, the RNA bases in the 5' extension are 2'-O-methyl modified to increase nuclease resistance.

For example, the thermodynamic stability of toehold binding to the activation signal can be increased via incorporation of 2'-O-methyl bases or locked nucleic acid (LNA) bases.

Figure 13:
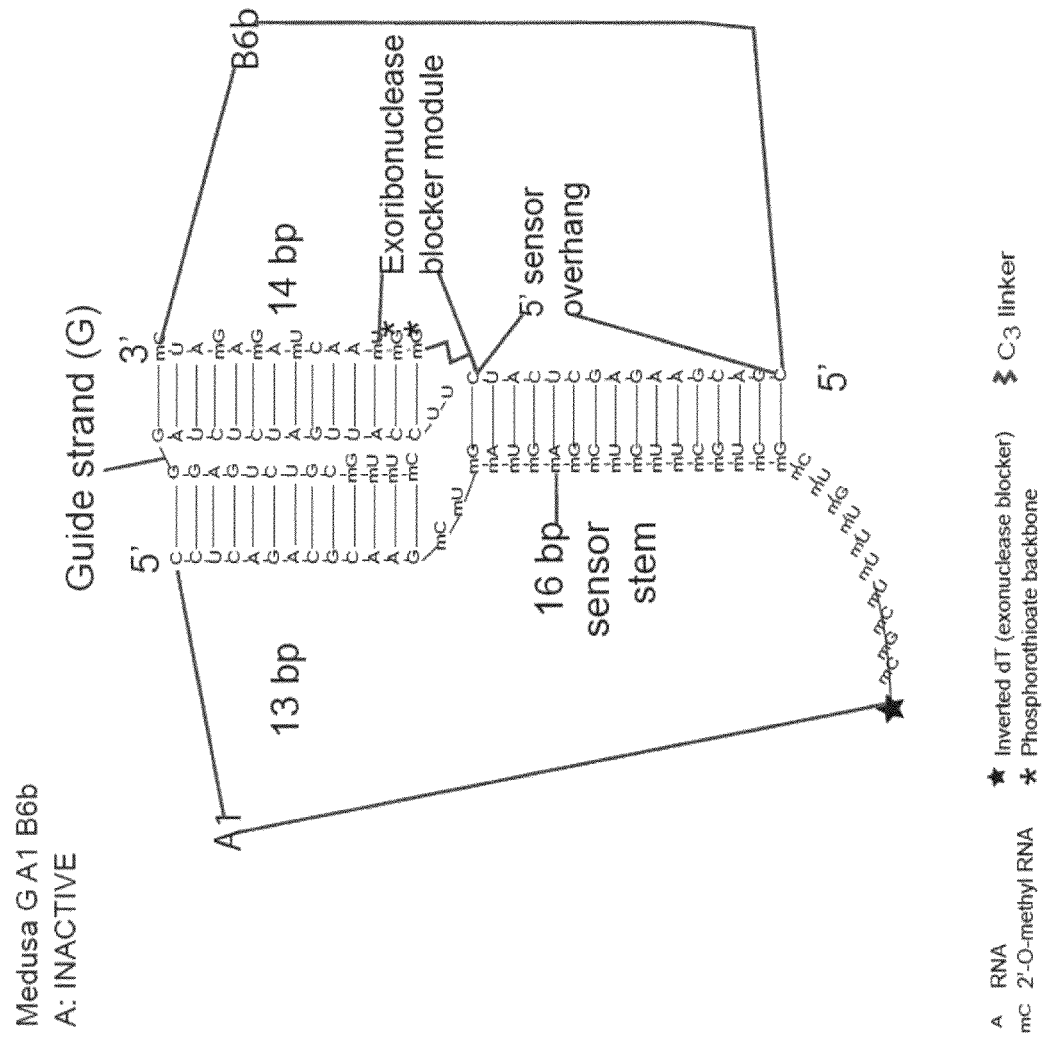
FIG. 13 shows a schematic illustration of an exemplary molecular construct, Medusa GA1B6b (SEQ ID NO. 1; SEQ ID NO. 3; SEQ ID NO. 17; SEQ ID NO. 18) which comprises the exemplary exonuclease resistant polynucleotide B6b (SEQ ID NO. 17; SEQ ID NO. 18). In particular.

The exemplary illustrations of FIGS. 13 and 14 show possible constructs modified to increase efficiency of RNAai activity following switch of an RNAaseH based construct from an inactive conformation to an active conformation. FIG. 13 shows an additional construct where portions of the displacement segments and the targeting domain comprise 2-O-methyl modified ribonucleotides and an inverted dT can be incorporated at the 3'-end of an oligo, leading to a 3'-3' linkage which inhibits both degradation by 3' exonucleases and extension by DNA polymerase. A further modification of the residues of the duplex is introduction of phosphorothioate linkage to protect the oligo from nuclease degradation as will be understood by a skilled person. In the illustration of FIG. 13 a C3 linker is also included in the target binding portion of the locking sensor to introduce unstructured linker to minimize activation of PKR degradation.

In the construct of FIG. 13 the 5' extension of the passenger strand can be degraded by XRN1 or another 5' exoribonuclease, or Dicer can interact with the targeting domain to process the guide strand without degradation of the 5' overhang (see also construct of FIG. 14). To allow this interaction, a C3 linker is placed at the position joining the 5' overhang to the passenger strand. In the ACTIVE state, the C3 linker serves two purposes. First, in case of exoribonucleolytic degradation of the 5' overhang, the C3 linker, in conjunction with adjacent 2'-O-methyl modifications and phosphorothioate backbone modifications, stops exoribonucleolytic processing. Second, the C3 linker gives extra flexibility prevent the 5' overhang from interfering with the processing of the targeting domain by Dicer. In the INACTIVE state, the C3 linker, along with the 2 un-paired bases on the opposite side of the sensor stem, connect the sensor stem to the targeting domain with sufficient slack to allow the structure to form correctly.

Although only polynucleotide targeting domains are shown in the illustration of figures of the present disclosure, in various embodiments of signal activatable construct herein described, a targeting domain can comprise a molecule other than RNA or a polynucleotide configured to be delivered to a target with the cells in the presence of the signal polynucleotide. Exemplary types of cargo molecule that can be comprised in all or in part as a targeting domain according to the current disclosure include but are not limited to peptides, small molecules aptamers, antibodies, and other chemical compound identifiable by a person skilled in the art.

The term "cargo" or "therapeutic cargo" as described herein refer to drugs, genes, and immunotoxins. Cargo for delivery for therapeutic use can be known to those skilled in the art and can be a substance for therapy. The cargo molecule can comprise various molecules such as aptamers, small molecules, peptides and/or polynucleotides.

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e.g. inhibition or activation of a target) or exogenous (e.g. cell signaling), which are used as a tool in molecular biology, or which are suitable as drugs in medicine. Small molecules can also have no relationship to natural biological molecules. Typically, small molecules have a molar mass lower than 1 kg·mol$^{-1}$. Exemplary small molecules include secondary metabolites (such as actinomicyn-D), certain antiviral drugs (such as amantadine and rimantadine), teratogens and carcinogens (such as phorbol 12-myristate 13-acetate), natural products (such as penicillin, morphine and paclitaxel) and additional molecules identifiable by a skilled person upon reading of the present disclosure.

The terms "peptide" and "oligopeptide" usually indicate a polypeptide with less than 50 amino acid monomers, wherein the term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived.

In these embodiments, the construct can also comprise a double-stranded polynucleotide duplex as part of the cargo.

In some embodiments, the exonuclease resistant polynucleotide can be used as an attachment domain for an assembly of a complex to an RNAi construct or for controlling the shape of an RNAi construct. The complex assembly is then released by exonucleases through degradation of the unmodified domain. The degradation is stopped by the incorporated blocking domain, the linkers, and the complex assembly is released without damage. In some embodiments this oligonucleotide construct can be used for the release of cargo, such as therapeutic cargo by controlled exonuclease degradation using the mechanism of XRN1.

For RNAi applications, it is desirable to have the linker domain connect the 5' or 3' terminus of the passenger or guide strand to a degradable linker segment. This allows the release of the RNAi domain from the linker by exonucleases without unacceptable degradation of the RNAi efficiency.

In those embodiments, the targeting domain formed by the cargo molecule or attaching the cargo molecule, can be carried and delivered by constructs herein described wherein the segments of the sensor domain are arranged in various configurations which allow switching of the construct from an inactive conformation to an active conformation with respect to the enzyme assisted release of the targeting domain as will be understood by a skilled person upon reading of the present disclosure. For example in embodiments, wherein the targeting segment is configured for delivery of a cargo molecule, the cargo molecule can be covalently linked to the 3' terminus of the passenger strand or to the 5' of the guide strand for targeting domain of 25 bp or longer. In those embodiments wherein the cargo molecule comprises a cargo such as a polynucleotide aptamer, the cargo molecule can be non-covalently attached to the construct for example through complementarily binding to the 5' terminus of the guide strand segment of the targeting domain or other base pairing segment linked to the displacement segment in a configuration that does not interfere with the binding of the signal molecule and allows release of the cargo with the displacement segment following RNAai processing of the guide strand. In particular, in some of the embodiments wherein a duplex formed between the cargo molecule and the passenger strand segment of the targeting domain or other base pairing segment, the duplex can have a melting temperature of at least 15° C.

The constructs and related components herein described can be designed and manufactured based on techniques described herein and/or identifiable by the skilled person upon reading of the present disclosure. In particular the configuration of the segments of the constructs can be identified and designed based on calculation of the thermodynamic stability of the various conformation of the segments and constructs as a whole. For example, thermodynamic stability of polynucleotide conformation dependents on several factors identifiable by a skilled person, including its i) chemical composition (for example, DNA:RNA duplex is less than RNA:RNA duplex); ii) base composition (for example, G/C base paring is more stable than A/T base paring, which is approximately as stable as G/T, G/U wobble base pairing, and the formation of a stable RNA hairpin requires at least 3 G/C base pairs or at least 5 A/U, G/U base pairs); iii) nearest neighbors such as presence of mismatches, open ends, and junctions near a base-pair can substantially influence its energy contribution according to the second-nearest neighbor model (for example, the stacking of successive base-pairs is primarily responsible for the stability of DNA helices); iv) non-canonical base pairing (for example, RNA and DNA can form triple helix and quadraplex structures via Hoogsteen base-pairing, which is less stable base pairings than canonical base pairing); v) Geometry (e.g. polynucleotide sequences can only adopt secondary structures that are geometrically consistent or similar with the known tertiary structural characteristics of RNA and DNA helices); vi) Environmental factors, such as pH value, counter-ion concentration and temperature and additional factors identifiable by a skilled person.

Accordingly, designing the polynucleotide sequences comprised in the signal activatable construct can be performed identifying the combination of length, sequence, complementarity and substitutions that is associated with a desired relative thermodynamic stability resulting in the configuration herein described and the environment wherein the enzyme assisted molecular delivery is desired. For example, in several embodiments of a signal activated polynucleotide construct, in absence of a signal polynucleotide, an inactive conformation of the signal activatable construct typically has approximately 3 extra G/C base pairs or 5 extra A/U or G/U base pairs as compared to the activated conformation formed in presence of the signal polynucleotide. Specific sequences of desired signal polynucleotides can be identified by a skilled person based on environment (and in particular, specific cells and tissues) where delivery is desired. Also, the number of complementary base pairs between the protection segment and displacement segment is typically more than that between the protection segment and the activation segment. For applications where molecular delivery in cells is desired, polynucleotide sequences can be designed according to the corresponding physiological conditions, such as approximately, pH 7.3-7.4, about 150 millimolar potassium or sodium chloride or equivalent salt, and about 37° C.

For base pairing between unmodified DNA segments or between unmodified RNA segments, the base-pairing energies and the most stable secondary structure conformations can be estimated by computational methods known to and well established in the art. Several packages are available and published in documents also discussing in detail factors affecting the energy and stability of nucleic acid secondary structures. Exemplary publications describing the packages and factors comprise for i) *NUPACK web server*: J. N. Zadeh, et al., (2011); ii) *NUPACK analysis algorithms*: R. M. Dirks et al., (2007); R. M. Dirks et al., (2003); R. M. Dirks et al., (2004); iii) *NUPACK design algorithms*: J. N. Zadeh et al., (2011); iv) mfold *web server*: M. Zuker, (2003); A. Waugh et al., (2002); M. Zuker et al., (1998); v) *UNAFold* & mfold: N. R. Markham et al., (2008); M. Zuker, et al., (1999); M. Zuker, (1994); J. A. Jaeger et al., (1990); M. Zuker, (1989); vi) *Free energies for RNA*: D. H. Mathews et al., (1999); A. E. Walter et al., (1994); vii) *Methods and theory of RNA secondary structure prediction*: D. H. Mathews et al., (2007); D. H. Mathews et al., (2006); D. H. Mathews et al. $3^{rd}$ edition, John Wiley & Sons, New York, Chapter 7, (2005); D. H. Mathews et al., (2004); M. Zuker, (1984); M. Zuker et al., (1981) D. H Mathews et al (2010); viii) *Exemplary* mfold & *UNAFold applications*: J.-M. Rouillard et al., (2003); J.-M. Rouillard, et al., (2002). In addition, since some polynucleotide structures typically fluctuate between an ensemble of secondary structure conformations, the composition of the relevant ensemble can be determined using computational methods known in the art (see for example, see Ye Ding et al., (2005), herein incorporated by reference in its entirety).

Accordingly, in several embodiments, design of a exonuclease resistant polynucleotide, exonuclease resistance duplex polynucleotide, and related constructs, can be performed for sequences or portions of sequences consisting of unmodified DNA and/or RNA base pairs, by computational methods and/or software packages to calculate the free energy of the sequence and the secondary structure conformation. In embodiments, wherein polynucleotide sequences comprise derivatives of nucleotides, such as chemically modified bases and analogues, and/or chimeric polynucleotide sequences composed of a mixture of deoxyribonucleotides and ribonucleotides, design can be performed by computationally designing unmodified RNA structures with the desired secondary structure conformations and thermodynamic stability, and then introducing one or more chemical modifications to achieve the desired thermodynamic stability. Exemplary chemical modifications comprise replacement of nucleotides that are needed to be base-paired to form a desired secondary structure with modified nucleotides that are known to increase thermodynamic stability (e.g. 2'-O-methyl modified nucleotides, LNA, PNA and Morpholino). Additional exemplary modifications comprise replacement of nucleotides that are not desired according to a certain thermodynamic stability with modified nucleotides to ensure that the resulting modified structures are likely to retain the desired secondary structure conformations and thermodynamic stability (e.g. replace a ribonucleotide base with a deoxyribonucleic base). A person skilled in the art will be able to identify other suitable modifications upon reading of the current disclosure.

The exonuclease resistant polynucleotide, the exonuclease resistant duplex polynucleotides and related construct can be designed according the present disclosure can be synthesized using standard methods for oligonucleotide synthesis well establish in the art, for example, see Piet Herdewijn, (2005), herein incorporated by reference in its entirety.

The synthesized oligonucleotide can be allowed to form its secondary structure under a desirable physiological condition, (e.g. 1× phosphate buffered saline at pH 7.5 with 1 mmolar concentration $MgCl_2$ at 37° C.). The formed secondary structure can be tested using standard methods known in the art such as chemical mapping or NMR. For example, see Stephen Neidle, (2008), herein incorporate by reference in its entirety. The designed construct can be further modified, according to the test result, by introducing or removing chemical modifications, mismatches, wobble pairings, as necessary, until the desired structure is obtained.

In some embodiments of signal activated polynucleotide constructs, in presence of a signal polynucleotide, the free energy of the construct in an activated conformation is at least about 5 kcal/mol lower than that of the construct in an inactive conformation.

In some embodiment of signal activated polynucleotide constructs, the free energy of complementary base-paring between the protection segment and the displacement segment is at least about 10 kcal/mol lower that the free energy of complementary base-paring between the DNA activation sequence and the RNA activation substrate.

In some embodiment of signal activated polynucleotide constructs, the targeting domain comprises a first segment and a second segment, wherein the first segment and the second segment form a polynucleotide duplex through complementarily binding with each other; and the 3' terminus of the second segment is adjacently connected with the protection segment of the sensor domain both segments.

In some embodiments of the exonuclease resistant polynucleotide, the exonuclease resistant duplex polynucleotides and related construct the guide strand, passenger strand, activation segment, displacement segment and toehold segment of the signal activatable construct are mainly composed of RNA and/or RNA derivatives.

The term "derivative" as used herein with reference to a first compound (e.g. RNA or ribonucleotide) indicates a second compound that is structurally related to the first compound and is derivable from the first compound by a modification that introduces a feature that is not present in the first compound while retaining functional properties of the first compound. Accordingly, a derivative of a molecule of RNA, usually differs from the original molecule by modification of the chemical formula that might or might not be associated with an additional function not present in the original molecule. A derivative molecule of RNA retains however one or more functional activities that are herein described in connection with complementary base paring with other nucleotides. Typically, ribonucleotides and deoxyribonucleotides can be modified at the 2', 5', or 3' positions or the phosphate backbone chemistry is replaced. Exemplary chemical modifications of a ribonucleotide according to the current disclosure include 2'-o-methyl RNA, 2'-Fluoro RNA, locked nucleic acid (LNA), peptide nucleic acid (PNA), morpholino, phosphorothioate oligonucleotides, and the like that are identifiable by a skilled person (see e.g. "Modified Nucleosides: in Biochemistry, Biotechnology and Medicine. Piet herdewijn (Editor), Wiley-VCH, 2008, herein incorporated by reference in its entirety). Also applicable are nucleosides which are not normally comprised in DNA and RNA polynucleotides, such as inosine. In some embodiments, a single oligonucleotide can be composed of more than one type of the above derivatives.

In particular, according to several embodiments herein described, the guide strand and passenger strand of the exonuclease resistant duplex polynucleotide comprise unmodified ribonucleotides. In other embodiments, the guide strand and passenger strand of the targeting domain can comprise modified ribonucleotides, such as 2'-O-methyl modification, 2'-fluoro modification, 2'-amino modification or LNA; the exposed 5' terminus of the passenger strand can have modifications configured to minimize processing by the XRN1. For example, 5' terminus of the passenger strand can have at least 1, and in particular 2 2-O-methyl ribonucleotide. Similarly the 3' terminus of the guide strand can have modifications configured to block processing by the endonucleases enzyme Dicer. For example, 3' terminus of the first segment can have at least 1, and in particular 2 deoxyribonucleotides. In some embodiments, the protection segment can comprises unmodified ribonucleotides and/or some modified ribonucleotides, such as 2'-O-methyl modification, 2'-fluoro modification, 2'-amino modification or LNA. In particular, in some embodiments, the two nucleotides immediately flanking the desired RNAse H cleavage site within the RNA activation sequence can be formed by unmodified ribonucleotides.

In some embodiments, the activation segment comprises a DNA activation sequence formed by unmodified deoxyribonucleotides. In particular in some of these embodiments the construct is an RNAaseH based construct.

In several embodiments, the toehold segment can comprise a polynucleotide sequence (herein also toehold sequence) that is at least 3 nucleotides in length and is fully complementary to at least a portion of the signal polynucleotide. This configuration of the toehold segment is expected to allow binding of a signal polynucleotide to bind to the signal activatable construct and initiate the branch migration process. A smaller toehold sequence is expected to result in better sequence specificity for signal discrimination, while a longer toehold sequence is expected to result in an increased ability to bind to the signal polynucleotides to form a desired secondary structure with respect to the ability of a shorter toehold segment. In some embodiments, the toehold segment can be arranged in single-stranded form and free of secondary structure. In particular, in some of those embodiments, the toehold sequence can be 4 to 12 nucleotides in length. In some embodiments, the toehold segment is composed of unmodified ribonucleotide. In particular, in other embodiments, the toehold segment comprises modified nucleotide configured for improved nuclease resistance. Exemplary modifications include but are not limited to 2'-O-methyl modification, 2'-Fluoro modifications, inclusions of LNA and PNA, and the like that are identifiable by a skilled person.

In some embodiments, the signal can be a single signal polynucleotide of a length shorter than 30 nucleotides, the toehold segment and the displacement segment is fully complementary to the signal polynucleotide. In other embodiments, the signal can be formed by multiple homologous signal polynucleotides. In these embodiments, the signal polynucleotides can be tested with a sensor design. Mismatches and wobble pairings or permissive bases such as inosine can be placed at positions in the 3:5 duplex corresponding to the variable sequences. In particular, in several embodiments, the Tm for the duplex formed by the signal polynucleotides with the toehold segment and the displacement segment is typically at least 25° C. and is typically at least equal to the operating temperature under which the construct will be used. In some embodiments, the 3' terminus of the sensor domain can have Dicer blocking groups which are identifiable by a skilled person.

Single stranded regions in the hairpin loop and in other areas can be protected by chemical modifications if not conflicting with other design objectives. 2'-O-methyl, 2'-fluoro, LNA, 2'-amino and other modified RNA nucleosides can replace RNA. Phosphorothioate deoxyribonucleotides can replace unmodified deoxyribonucleotides for RNAseH segment.

In some embodiment, wherein the locking sensor comprises more than one polynucleotide the melting temperature of the duplex formed by the displacement segment and the activation segment is at least 5° C. above the expected operating temperature under which the construct is used, (e.g. 37° C. for the use in human cells) in order to prevent spurious activation.

In some embodiments, in absence of a signal polynucleotide, the displacement segment and the protection segment form a double-stranded duplex. In particular, the double-stranded duplex formed by the displacement segment and the protection segment can have up to 30 consecutive base pairs, if the duplex comprises only unmodified ribonucleotides. In other embodiments, the double-stranded duplex formed by the displacement segment and the protection segment can be longer than 30 base pairs, if the duplex comprises mismatches and/or modified ribonucleotides. In particular, mismatches and/or modifications are expected to contribute to preventing activation of innate immune system and/or increase stability. Exemplary modifications to the first and the second segments include but are not limited to 2'-O-methylation, 2'-Fluoro modifications, 2'-amino modifications, and inclusion of LNA or PNA nucleotides. In particular 2'-O-methylation can be used to passivate against innate immune activation. In some embodiments, the displacement segment is at least 12 nucleotides in length. In some embodiments, the displacement segment can be at least 14 nucleotides in length.

In some embodiments, the construct is configured to minimize immune responses. In these embodiments, each consecutive 30 base pairs duplex can have at least 5% 2'-O-methyl modifications (Molecular Therapy (2006) 13, 494-505, herein incorporated by reference in its entirety) or one or two mismatches. In other embodiments, the construct is configured to stimulate immune responses. In these embodiments, the construct can comprises at least one consecutive 30 base-pair duplex with no 2'-O-methyl modifications when the construct is in the activated conformation. For example, the total length of the toehold segment and the displacement segment can be at least 30 nucleotides without 2'-O-methyl modifications, and will be perfectly base paired with the signal polynucleotide sequence.

In some embodiments, the guide strand is configured to interfere with a target intracellular process of the cells through RNAi in presence of the signal polynucleotide. Accordingly suitable targeting domain include siRNA, microRNA and additional duplex structure suitable to be used in connection with RNA interfering.

The term "RNA interfering" or "RNAi" as used herein refers to a mechanism or pathway of living cells that controls level of gene expression that has been found in many eukaryotes, including animals. The RNAi pathway has many important roles, including but not limited to defending cells against parasitic genes such as viral and transposon genes, directing development and regulating gene expression in general. The enzyme Dicer, which is an endoribonuclease in the RNAse III family, initiates the RNAi pathway by cleaving double-stranded RNA (dsRNA) molecules into short fragments of dsRNAs about 20-25 nucleotides in length. Dicer contains two RNase III domains and one PAZ domain; the distance between these two regions of the molecule is determined by the length and angle of the connector helix and determines the length of the siRNAs it produces. Dicer cleaves with the highest efficiency dsRNA substrates 21 bp and longer with a two-base overhang at the 3' end.

The small fragments of dsRNAs produced by Dicer are known as small interfering RNA (siRNA). The term "small interfering RNA" or "siRNA", sometimes also known as short interfering RNA or silencing RNA, refers to a class of dsRNA molecules which is typically 20-25 nucleotides in length and plays a variety of roles in biology. The most notable role of siRNA is its involvement in the RNAi pathway. In addition to its role in the RNAi pathway, siRNA also acts in RNAi-related pathways, including but not limited to several antiviral pathways and shaping chromatin structure of a genome.

Each siRNA is unwound into two single-stranded (ss) ssRNAs, namely the passenger strand and the guide strand. The passenger strand is degraded, while the guide strand is incorporated into a multiprotein complex, known as the RNA-Induced Silencing Complex (RISC). RISC uses the incorporated ssRNA as a template for recognizing a target messenger RNA (mRNA) molecule that has complementary sequence to the ssRNA. Upon binding to the target mRNA, the catalytic component of RISC, Argonaute, is activated, which is an endonuclease that degrades the bound mRNA molecule.

Similar to siRNAs, microRNAs (miRNAs) also mediate the RNAi pathway. The term "microRNA" or "miRNA" as used herein indicates a class of short RNA molecules of about 22 nucleotides in length, which are found in most eukaryotic cells. miRNAs are generally known as post-transcriptional regulators that bind to complementary sequences on target mRNA transcripts, usually resulting in translational repression and gene silencing.

miRNAs are encoded by miRNA genes and are initially transcribed into primary miRNAs (pri-miRNA), which can be hundreds or thousands of nucleotides in length and contain from one to six miRNA precursors in hairpin loop structures. These hairpin loop structures are composed of about 70 nucleotides each, and can be further processed to become precursor-miRNAs (pre-miRNA) having a hairpin-loop structure and a two-base overhang at its 3' end.

In the cytoplasm, the pre-miRNA hairpin is cleaved by the RNase III enzyme Dicer. Dicer interacts with the 3' end of the hairpin and cuts away the loop joining the 3' and 5' arms, yielding an imperfect miRNA:miRNA duplex about 22 nucleotides in length. Overall hairpin length and loop size influence the efficiency of Dicer processing, and the imperfect nature of the miRNA:miRNA base pairing also affects cleavage. Although either strand of the duplex can potentially act as a functional miRNA, only one strand is usually incorporated into RISC where the miRNA and its mRNA target interact.

In those embodiments, wherein the guide strand is configured for interfering a target intracellular process through RNAi, the double-stranded duplex typically formed by the guide strand and passenger strands can have a melting temperature (Tm) of at least about 25° C. In particular, the 5' terminal nucleotide of the guide strand can be base paired to one of the passenger strands. In some embodiments, nicked double-stranded duplex formed by the guide strand and passenger strands are stable under conditions of the environment where delivery will be performed. In embodiments where RNAi is performed in mammals the nicked double-stranded duplex typically formed by the guide strand and passenger strand can have a melting temperature (Tm) of at least about 37° C.

In particular, in some embodiments, the double-stranded duplex formed by the first segment and the second segment are no longer than 30 consecutive base pairs, if the duplex comprises only unmodified ribonucleotides. In other embodiments, the double-stranded duplex formed by the first segment and the second segment can be longer than 30 base pairs, if the duplex comprises mismatches and/or modified ribonucleotides. The mismatches and/or modifications are likely to prevent activation of innate immune system. Exemplary modifications to the first and the second segments include but are not limited to 2'-O-methylation, 2'-Fluoro modifications, 2'-amino modifications, and inclusion of LNA or PNA nucleotides. In particular, 2'-O-methyl, 2'Fluoro, 2' amino, LNA and PNA are expected to improve stability of the structure.

In other embodiments, the 3' terminal region of segments other than the guide strand comprises modifications to inhibit RNAi loading pathway enzyme processing from the 3' terminus of the first segment. In particular, in some embodiments, the last at least 1 base at the 3' terminal region of the first segment is a DNA modified DNA base. In particular, the last 2 nucleotides at the 3' terminal region of the first segment is a DNA modified DNA base. In other embodiments, the 3' terminal region of segment 1 is chemically modified. Exemplary modifications includes but are not limited to 3'-O-propanediol modifications, 3'-O-fluorescin modifications, 3'-puromycin modifications, 3'-inverted dT modifications, inverted Dideoxy-T modifications and the like that are identifiable by a skilled person in the art.

The term "homologous" or "homology" used herein with respect to biomolecule sequences as indicates sequence similarity between at least two sequences. In particular, according to the current disclosure, a homologous sequence of a mammalian miRNA can have the same sequence located at base position 2-7 from the 5' terminus of the guide strand of the miRNA.

In an embodiment, a targeting domain can be attached to a locking sensor herein described with methods and approaches identifiable by a skilled person. In particular, attachment can be performed at a portion of the protection domain configured for binding the targeting domain (e.g. presenting a suitable functional group) and presented for binding in the sensor domain. Exemplary target binding portion herein described comprise a monomer presented in the 5' terminus of the protection domain. A skilled person will be able to identify additional suitable portions, including intermediate compound or functional groups used to covalently attach the targeting domain with the protection domain at any suitable portion. In particular the target binding portion of the protection segment and the activation domain are typically attached of the RNA portion of the protection segment.

In some embodiments, a system for intracellular information processing and controlling of cells is described. The system comprising two or more of the constructs herein described, in which the targeting domain of at least one construct of the two or more constructs is configured to release a second signal in the presence of the signal polynucleotide, and the second signal is configured to activate one or more construct of the two or more constructs.

In some embodiments, one or more signal activatable constructs and/or component thereof including sensor domains can be used in a method for XRN1 or RNAse H assisted signal activated molecular delivery in cells. The method comprises delivering to the cells an effective amount of one or more of the signal activatable construct described herein possibly preceded by contacting the sensor domain with a suitable targeting domain to provide the construct.

In some embodiments, RNA and DNA nanostructures herein described can allow specific biomolecules to trigger specific changes in their secondary, tertiary and quaternary structure. These characteristics are comprised in several embodiments of activatable constructs herein described as will be understood by the skilled person to develop novel switching mechanisms that work with endogenous nucleases to activate or release therapeutic cargo.

In one embodiment, illustrated in FIGS. 12, 13, 14, 15, 16 and 17 a sensor gated siRNA can be provided with selectively activated RNAi activity in cells expressing a specific RNA sequence. The activating sequence switches ON the siRNA by binding to its sensor domain and triggering internal conformational changes that induce processing by endogenous RNAse H or XRN1. The result is an active Dicer substrate that can direct targeted RNAi.

As disclosed herein, constructs and related components herein described can be provided as a part of systems for enzyme assisted molecule delivery, including any of the deliveries described herein. The systems can be provided in the form of kits of parts. In a kit of parts, the signal activated constructs and related components and other reagents to perform enzyme-assisted delivery can be comprised in the kit independently. The signal activated constructs and related components can be included in one or more compositions, and each construct or component can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of molecule delivery can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, one or more signal activated constructs and/or related components, (e.g. sensor domain,) herein described are comprised in a composition together with a suitable vehicle. The term "vehicle" as used herein indicates any of various media acting usually as solvents, carriers, binders or diluents for signal activated constructs and related components that are comprised in the composition as an active ingredient. In particular, the composition including the signal activated constructs and related components can be used in one of the methods or systems herein described.

In some embodiments, a composition for XRN1 and/or RNAse H assisted signal activated molecular delivery can comprise one or more of the signal activatable construct as described together with a suitable vehicle. In some embodiments, the vehicle is suitable for delivering the signal activatable construct to cells. Exemplary suitable vehicles according to the current disclosure include but are not limited to nanoparticle, such as cyclodextrin, gold nanoparticle and dendrimer; liposome and liposome analogues; conjugated aptamer; conjugated antibody; conjugated cell penetrating peptide or peptide analogue; carbon nanotubes; conjugated fatty acids and quantum dots. In particular, the XRN1 enzyme can degrade the RNA segment presented in targeting domain allowing binding and processing of the targeting domain by Dicer or other enzyme of the RNAai inactivation pathway.

In some embodiments, the signal activated constructs and related components herein described are comprised in pharmaceutical compositions together with an excipient or diluent.

The term "excipient" as used herein indicates an inactive substance used as a carrier for the active ingredients of a medication. Suitable excipients for the pharmaceutical compositions herein described include any substance that enhances the ability of the body of an individual to absorb the signal activated constructs and related components herein described or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, disclosed are pharmaceutical compositions which contain at least one signal activated constructs and related components as herein described, in combination with one or more compatible and pharmaceutically acceptable vehicles, and in particular with pharmaceutically acceptable diluents or excipients. In those pharmaceutical compositions the signal activated constructs and related components can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individual" as used herein in the context of treatment includes a single biological organism, including but not limited to, animals and in particular higher animals and in particular vertebrates such as mammals and in particular human beings.

For example in some embodiments, a multi-stage therapeutic nanoparticles can be provided that utilize XRN1 and/or RNAaseH activated release of a cargo in a cell to achieve controlled step-wise disassembly and cargo release in target environment such as solid tumor microenvironments.

A skilled person will be able to identify further application and in particular therapeutic applications as well as cargo molecules to be used as active agents in the treatment and design a corresponding signal activatable construct to be administered according to the features of the construct and the desired effect. In particular, in applications wherein signal activatable construct is desired system administration of the agent can be performed. In embodiments, where an activated construct is instead used, topical administration to the specific target cell and tissue can be performed.

Further advantages and characteristics of the present disclosure will become more apparent hereinafter from the following detailed disclosure by way or illustration only with reference to an experimental section.

EXAMPLES

The synthesized signal activatable constructs and duplexes herein disclosed are further illustrated in the following examples, which are provided by way of illustration and are not intended to be limiting.

The following material and methods were used in the experiments illustrated in the following examples.

Northern Blot Analysis:

HCT116 cells were transfected with the indicated exemplary constructs, duplexes or controls at a final concentration of 1 nMolar with pBluescript (pBS) as carrier, using Lipofectamine-2000 according to the manufacturer's (Invitrogen) protocol. The cell medium (American Type Culture Collection, recommended formulation) was replaced at 18 hours post-transfection. Total cell RNA was harvested at 24 hours post-transfection using RNASTAT60 (amsbio) according to the manufacturer's instructions, except for the addition of a second 1:1 phenol:chloroform pH 6.7 extraction prior to precipitation. For Northern analyses, 15 ug of total RNA from cells transfected with exemplary constructs, duplexes or pBS carrier only as a mock transfected control (Mtf) in 1× formamide loading buffer were run on a 12% urea/PAGE gel, along with $^{32}$P-end-labeled Ambion Decade size markers (M). The RNA was transferred to Hybond XL (Amersham) using the BioRad TransBlot SD (semi-dry) cell. Transferred RNA was cross-linked to the membrane using the UV Stratalinker 2400 (Stratagene) preset conditions. Membranes were prehybridized 6-10 hours at 37 degrees Celsius with Perfecthyb Plus (Sigma) and hybridized in the same buffer overnight at 37 degrees Celsius with 5-10 pmoles of $^{32}$P-end-labeled oligo probes as shown. After 2×SSC/1% SDS washes at 37° C., the membranes were exposed using Kodak BioMax film and intensifying screens at –80° C. and developed according to the manufacturer's instructions.

Transfections for Luciferase Analyses:

Briefly, HCT116 cells were transfected with the indicated exemplary constructs, duplexes, or controls at the indicated final concentrations (ranging from 0.04 to 5 nMolar) with pBluescript (pBS) as carrier, using Lipofectamine2000 according to the manufacturer's (Invitrogen) protocol. The cell medium was replaced at 18 hours post-transfection and lysates collected at 24 hours post-transfection for analysis. Specifically, one day before transfection, cells were seeded in growth medium in 48-well cluster plates without antibiotics so that cells would reach 90-95% confluency at the time of transfection (as recommended by Invitrogen protocols). Each well was transfected with a final DNA mix consisting of: 40 nanograms (ng) psiCHECK (Promega) plasmid bearing a Firefly luciferase (Fluc) control reporter and a *Renilla* luciferase (Fluc) reporter with the target in the 3' UTR (untranslated region); 120 ng pBluescript carrier DNA; and the experimental constructs or duplex diluted in 10 mM Tris/1 mM EDTA pH 6.7 (TE). The final DNA mix therefore consisted of 16 ul of target mix in OptiMEM and 4 ul of experimental DNA at 50× the final desired concentration in TE. To reduce sample to sample variability, the psiCHECK target mix was made in batch in OptiMEM and aliquoted to allow 3 technical replicates (wells) for each condition prior to addition of the experimental DNA. An equal volume of a ⅙₀ dilution of Lipofectamine2000 in OptiMEM was added (bringing the volume to ⅕th the final) and incubated according to the manufacturer's instructions. The liposome/DNA constructs or duplexes were added, along with fresh complete medium to the cells to give a final volume of 200 ul. Medium was replaced at 18 hours post-transfection. At 24 hours, samples were collected for luciferase analysis using the Promega Dual-Luciferase Reporter Assay System kit according to the manufacturer's protocol. For each replicate, the *Renilla* luciferase (target) value was normalized to the Firefly luciferase (internal control) value. Triplicates were averaged, and the experimental values as a fraction of carrier alone (no experimental construct), whose value is set at 1. Therefore, the greater the RNAi activity, the lower the relative luciferase units.

Example 1

Exemplary Exonuclease Resistant Polynucleotides

Exemplary molecular constructs and duplexes were provided having the physical and chemical B strands used in the exemplars and are summarized in Table 1 below. The table indicates for each exemplary exonuclease resistant molecular constructs and duplexes the specific sequences of the strands that are complementary bound to provide the duplexes and constructs herein described.

TABLE 1

| | B strand characteristics | | | | | | | |
|---|---|---|---|---|---|---|---|---|
| | nt in duplex* | | | 5' extension description | | Total B | Total | |
| B strand ID | # paired* | # of 2' O—CH₃ | Blocker module | nt | modifications | strand length, nt | duplex length* | SEQ ID NO. |
| pB | 14 | 4 | No | none | NA | 14 | 27 | 14 |
| B6-R | 14 | 4 | No | 16 | all RNA | 30 | 27 | 19 |
| B6b | 14 | 4 | Yes | 16 | all RNA | 30 | 27 | 17, 18 |
| B7c | 13 | 3 | Yes | none | NA | | | 38 |
| B7 | 13 | 3 | Yes | 15 | none | 28 | 25 | 25, 26 |
| B10 | 13 | 3 | Yes | 15 | all PS linkages, including the | 28 | 25 | 27, 28 |

TABLE 1-continued

| | B strand characteristics | | | | | Total B | Total | |
|---|---|---|---|---|---|---|---|---|
| | nt in duplex* | | | 5' extension description | | strand | duplex | SEQ |
| B strand ID | # paired* | # of 2' O—CH₃ | Blocker module | nt | modifications | length, nt | length* | ID NO. |
| B11 | 13 | 3 | Yes | 15 | 3' side of the C3 linker: 5' terminal HEG** 3 PDE linkages proximal to C3 linker; remaining are PS linkages: 5' terminal HEG** | 28 | 25 | 29, 30 |
| B12 | 13 | 3 | Yes | 15 | 12 PDE linkages proximal to C3 linker; remaining are PS linkages: 5' terminal HEG** | 28 | 25 | 31, 32 |

PDE—standard phosphodiester linkages
PS—phophorothioate linkages
*when complexed with A and G strands
**hexaethyleneglycol
Note:
the only differences between B7, B10, B11, and B12 reside in the composition of the 5' extension Example 2

Exemplary Components for the Exonuclease Resistant Polynucleotide and Related Constructs Component strand features for constructing the constructs and duplexes with the exonuclease resistant polynucleotides are indicated below in Table 2. The table below gives strand sequences and pertinent characteristics for strands that are schematically shown in the corresponding configurations containing the sequences that are shown in FIGS. 13, 14, 16, and 17 for the constructs, and in FIGS. 3, 4, 5, 6, and 7 for the duplexes.

Features of the exemplary constructs or duplexes are detailed below in Table 2.

TABLE 2

Strand sequences for strands used in construct and duplex design

| Name | Abbreviation | # nt | Description | Sequence 5' → 3' | Notes | SEQ ID NO. |
|---|---|---|---|---|---|---|
| Guide strand 1 | G1 | 29 | U5K2 targeting guide strand for the medusa | mC mU mU mG C G U C U G A G G G A U C U C U A G U U A C C U U | Homology to probe 544 (to U5 guide) UCUGAGGGAUC UCUAGUUACC (SEQ ID NO. 2) | 1 |
| Medusa A1 | A1 | 37 | Sensor A version 1 for medusa | C C U C A G A C G C A A G mC mU mG mA mU mG mA mG mC mU mC mU mU mC mG mU mC mG mC mU mG mU mU idT | | 3 |
| Medusa A2 | A2 | 36 | | C C U C A G A C G C A *mA *mG 18S G A U G A G C U C U U C G U C G C U G U C U C | | 4, 5 |
| Medusa A3 | A3 | 35 | | C C C U C A G A C G mC mG * 18S G A mU G mA G mC mU U C mG mU C G 9S G U mC U mC mC G mC 9S idT | CUGAUGAGCUCU UCGUCGCUGUCU CCGC -- GAUGAG-- CUUCGUCG-- GUCUCCGC (SEQ ID NO. 9) Bubbled to interrupt continuous helix | 7, 8 |
| Medusa A4 | A4 | | | cccucagacg mc*mg* /9s/ mG mA mU mG mA mG mCmU mU mC mGmU mC mG 9s mG mU mC mU mC mC mG mC 9s idT | 9s is triethyleneglycol linker, idT is inverted dT base | 10, 11, 12 |

TABLE 2-continued

Strand sequences for strands used in construct and duplex design

| Name | Abbreviation | # nt | Description | Sequence 5' → 3' | Notes | SEQ ID NO. |
|---|---|---|---|---|---|---|
| Medusa passenger A control | pA | 14 | Truncated sensor A strand for medusa control, 3' end of passenger (together with Bc, homologous to guide) | C C U C A G A C G C A A G idT | | 13 |
| Medusa passenger B control | pB | 14 | Truncated sensor B strand for medusa control, homologous to 3' end of guide; with Ac homologous to entireity of guide | G G U A A C U A G A G A U C | | 14 |
| Tat 28 base act strand | S1 | 39 | Tat/Rev signal activator, 28 nt to fit extended toehold | mA mA mA mA mA G C G G A G A C A G C G A C G A A G A G C U A U C A G mA mA mA mA mA idT | overlapping 179,585 homologies | 15 |
| Signal strand 2 | S2 | | Alternative signal strand for Medusa constructs | mA.mA.mA.mA.mA.G.C. G.G.A.G.A.C.A.A.C.G.A.C. G.A.A.G.C.U.C.A.U.C.mA. mA.mA.mA.mA.idT | | 16 |
| Medusa B v6b 16 bp sensor | B6b | 30 | Passenger strand with blocker module | C G A C G A A G A G C U C A U C C3 mG * mG * mU A A C mU AmG A mG A U mC | overlapping 585 and senB LNA homologies | 17, 18 |
| Medusa B6b-R | B6b-R | 30 | Passenger strand without blocker module | C G A C G A A G A G C U C A U C G G U A A C mU A mG A mG A U mC | | 19 |
| Guide strand 2 | G2 | 27 | non-methylated sequence same as G; G had 5' mC mU mU mG | mC mG C G U C U G A G G G A U C U C U A G U U A C C U U | Homology to probe S44 (to US guide) UCUGAGGGAUC UCUAGUUACC (SEQ ID NO. 21) | 20 |
| Guide strand3 | G3 | 27 | G2 with LNA | mC mG +C G U C U G A G G G A U C U C U A G U | Homology to probe 544 (to U5 guide) UCUGAGGGA UCUCUAGUU ACC (SEQ ID NO. 23); +C and +T LNA bases | 22 |
| Passenger A control strand 4 | Ac4 | 12 | Works with G2 and G3 | cccucagacg mc*mg | mg attached to triethylene glycol idT | 24 |
| B7 | B7 | 28 | | C G A C G A A G C U C A U C A C3 mG * mG * mU A A C U mA G A mG A mU | overlapping 586, 585 and senB LNA homologies | 25, 26 |
| Passenger B10 | B10 | 27 | | 18s *C*G*A*C*G*A*A*G*C *U*C*A*U*C*c3*mG* mG*mUAAC U mA G A mG A mU | overlapping 586, 585 and senB LNA homologies | 27, 28 |

TABLE 2-continued

Strand sequences for strands used in construct and duplex design

| Name | Abbreviation | # nt | Description | Sequence 5' → 3' | Notes | SEQ ID NO. |
|---|---|---|---|---|---|---|
| Passenger B11 | B11 | 27 | 18s | *C*G*A*C*G*A*A*G*C *U*C*AUCc3mG*mG*m UAAC U mA G A mG A mU | overlapping 586, 585 and senB LNA homologies | 29, 30 |
| Passenger B12 | B12 | 27 | 18s | *C*G*A*CGAAGCUCAU Cc3mG*mG*mUAAC U mA G A mG A mU | overlapping 586, 585 and senB LNA homologies | 31, 32 |

*asterisk refers to phosphothiester linkages

With particular reference to exemplary related constructs, illustrated in the Figures, in, FIG. 3A, the 5' overhang (labeled as the 5' extension), comprises an unmodified RNA sequence 5'-CGACGAAGCUCAUCA-3' (SEQ ID NO. 25). This sequence is connected to the C3 linker via a phosphodiester linkage. This overhang is not exonucleases resistant. This example is expected to be an efficient RNAi substrate. In FIG. 3B, the overhang and blocker domain comprise of the sequence RNA sequence 5'-PEG*C*G*A*C*G*A*A*G*C*U*C*A*U*C*C3*m G*mG*mU-3' (SEQ ID NO. 35; SEQ ID NO. 48). where * indicates a phosphorothioate linkage. This overhang is exonucleases resistant due to the presence of a 5' PEG (hexaethyleneglycol) and the phosphorothioate linkages. However, the blocker domain is incorrectly formulated due to the presence of phosphorothioates connecting the C3 linker to the overhang and the mG. Thus, this example is expected to cause low RNAi activity. In FIG. 3C, the overhang and blocker are comprised of the sequence: 5'-PEG*C*G*A*C*G*A*A*G*C*U*C*A U C C3 mG*mG*mU-3'(SEQ ID NO. 36; SEQ ID NO. 48). Thus, in FIG. 3C, the C3 linker group is connected to the overhang and the rest of the blocker domain via phosphodiester linkages. This configuration, and the reduction in the number of phosphorothioates in the 5' overhang is expected to lead to increased RNAi activity with respect to a corresponding sequence where the C3 linker is connected via phosphorothioate linkages. In FIG. 3D, the overhang and blocker domain is comprised of the sequence 5'-PEG*C*G*A C G A A G C U C A U C C3 mG*mG*mU-3' (SEQ ID NO. 36; SEQ ID NO. 48).

In the illustration of FIGS. 4A to 4D, the blocker domain of the exonuclease resistant polynucleotide is indicated as blocker module and attaches a 5' overhang comprised in a configuration allowing presentation of the 5' overhang at the 5' end. In FIG. 4A, the 5' overhang (labeled as the 5' extension), comprises an unmodified RNA sequence 5'-CGAC-GAAGCUCAUCA-3' (SEQ ID NO. 25). This sequence is connected to the C3 linker via a phosphodiester linkage. This overhang is not exonucleases resistant. This example is expected to be an efficient RNAi substrate. In FIG. 4B, the overhang and blocker domain comprise of the sequence RNA sequence 5'-PEG*C*G*A*C*G*A*A*G*C*U*C*A*U*C*C3*m G*mG*mU-3' (SEQ ID NO. 35; SEQ ID NO. 48). where * indicates a phosphorothioate linkage. This overhang is exonucleases resistant due to the presence of a 5' PEG (hexaethyleneglycol) and the phosphorothioate linkages. However, the blocker domain is incorrectly formulated due to the presence of phosphorothioates connecting the C3 linker to the overhang and the mG. Thus, this example is expected to cause low RNAi activity. In FIG. 4C, the overhang and blocker are comprised of the sequence: 5'-PEG*C*G*A*C*G*A*A*G*C*U*C*A U C C3 mG*mG*mU-3' (SEQ ID NO. 36; SEQ ID NO. 48). Thus, in FIG. 4C, the C3 linker group is connected to the overhang and the rest of the blocker domain via phosphodiester linkages. This configuration, and the reduction in the number of phosphorothioates in the overhang is expected to lead to an increased RNAi activity with respect to a corresponding sequence wherein C3 linker is connected to the 5' and 3' oligonucleotides with phosphorothioate. In FIG. 4D, the overhang and blocker domain is comprised of the sequence 5'-PEG*C*G*A C G A A G C U C A U C C3 mG*mG*mU-3' (SEQ ID NO. 36; SEQ ID NO. 48). Thus, a lower number of phosphorothioates compared to the overhang shown in FIG. 4C, is expected decrease nuclease resistance further compared to the exonuclease resistance of the configuration in FIG. 4C. Example 11 and Example 12 show experimental results matching the expectations created by the structure of overhangs in FIG. 4A to FIG. 4D. Thus, the configuration in FIG. 4A is shown to have the highest RNAi activity in Example 11 and a larger amount of Dicer product in Example 12 compared to the other exonuclease resistant duplex polynucleotides shown in FIG. 4. The configuration in FIG. 4B has the lowest RNAi activity and Dicer processing compared to the other exonuclease resistant duplex polynucleotides shown in FIG. 4. The RNAi activity of the configuration in FIG. 4C is significantly higher than that of the configuration shown in FIG. 4B. The RNAi activity of the configuration in FIG. 4D is higher than the RNAi activity of the example configuration in FIG. 4C.

In FIG. 4 the B7, B10, B11 and B12 (SEQ ID NO. 25; SEQ ID NO. 26; SEQ ID NO. 27; SEQ ID NO. 28; SEQ ID NO. 29; SEQ ID NO. 30; SEQ ID NO. 31; SEQ ID NO. 32;) strands differ in that the degree of phosphorothioation of the 5' extension connected to the blocker module. B7 has an unmodified 5' extension with only RNA base and standard phosphodiester backbone connections. The B10 differs from B7 in that the 5' extension on B10 has all phosphorothioate backbone connections. B10 also has a 5' terminal hexaethyleneglycol and the connections flanking the C3 linker in the blocker module. In B11, the phosphorothioate bonds present around the blocker module and flanking the C3 linker are changed back to phosphodiester connections. In B12, most of the phosphorothioate backbone connections in the 5' extension have been removed, leaving only three such connections at the 5' terminus. Additionally in B7 the 5' extension has an extra adenine immediately to the 5' of the blocker module.

As shown in the example section for the constructs of FIG. 4, the 5' extension, in B7 is more easily processed by 5' exoribonucleases with respect to B10, B11 and B12 while the extension in B10 is expect to be more exonuclease resistant than B7, B11 and B12 (the positions probed by Northern blot probes 544 and SenB-LNA are shown highlighted in gray). A difference between B10 and all other exemplary exonuclease resistant polynucleotides of FIG. 4 is that cleavage of the backbone linking the C3 in the blocker module to the 5' extension leaves a phosphorothioate 5' terminus.

In the duplex shown in FIG. 7, the guide strand G is 29 nucleotides long and forms a 27 base pair duplex with two passenger strand segments pA and pB. At the 3' end of G, there is a 2 base UU overhang terminated by an OH. The 5' terminus of pB, which sits opposite the UU overhang, is flush and terminated with a phosphate. Dicer's PAZ domain binds to the UU 3' overhang and the 5' phosphate. The 3' end of pA terminates with an inverted dT base which discourages binding of Dicer's PAZ domain from that end. Thus, this configuration favors cleavage of the G strand at its 21$^{st}$ base from the 3' terminus. Thus, when processed by Dicer, the guide strand used in RISC is 5'-UGAGGGAUCUCUAGUUACCUU-3' (SEQ ID NO. 37). pB has a number of 2'-O-methyl modified bases to increase thermodynamic stability while the G strand has 4 2'-O-methyl modified bases at the 5' terminus to increase energetic stability. To ensure proper Dicer processing, there are no 2'-O-methyl modifications near the Dicer cleavage site on either strand. Furthermore, the segmented passenger strands are too short for loading into RISC as the guide strand. This ensures that only the Dicer cleavage product of the G strand can be loaded into RISC. This feature increases the target specificity of RNAi knockdown FIG. 5A illustrates a Dicer substrate with a 5' overhang on the passenger strand B6b. This overhang is connected to the passenger strand segment via a blocker domain 5' C3-mG*mG*mU-3' (SEQ ID NO. 48). The overhang is comprised of unmodified RNA bases and is not exonucleases resistant. Thus, a 5' cytoplasmic exonucleases such as exoribonuclease 1 (XRN1) can degrade the overhang while leaving a 5' terminal phosphate on the blocker module. This then allows binding of the PAZ domain to the 5' phosphate connected to the C3 linker and the 3' UU over hang on the G strand. Dicer cleavage takes place 21 nucleotides up from the 3' terminus on the G strand, causing a guide strand segment 5'-UGAGGGAUCUCUAGUUACCUU-3' (SEQ ID NO. 37) to be loaded into RISC. Thus, the construct G pA B6b is expected to have an RNAi activity resulting in a 50% or greater inhibition of protein production as detected by dual luciferase assays, as is shown in Example 11 and Example 12. FIG. 5B illustrates an example of a targeting domain, G pA B6-R (SEQ ID NO. 1; SEQ ID NO. 13; SEQ ID NO. 19) having an RNAai activity lower than G pA B6b (SEQ ID NO. 1; SEQ ID NO. 13; SEQ ID NO. 17; SEQ ID NO. 18). In G pA B6-R (SEQ ID NO. 1; SEQ ID NO. 13; SEQ ID NO. 19), the 5' overhang on B6-R is connected to the passenger segment of B6-R via a simple phosphodiester linkage. The modifications associated with the blocker domain are not present. Thus, when the overhang is not degraded, Dicer's PAZ domain cannot bind correctly to the 3' end of the G strand. When exonucleases degrade the overhang on B6-R, the exonucleases are expected to continue degrading the rest of the B6-R strand, including the passenger segment. This destroys the RNAi targeting domain. Thus, as shown in Example 11 and Example 12, G pA B6-R has a lower detectable RNAi activity as compared to G pA B6b (SEQ ID NO. 1; SEQ ID NO. 13; SEQ ID NO. 19) and few detectable Dicer products.

Reference is made to the exemplary illustration of FIG. 6 which shows two Dicer substrates G2 Ac4 B7c (SEQ ID NO. 20; SEQ ID NO. 24; SEQ ID NO. 38) and G3 Ac4 B7c (SEQ ID NO. 22; SEQ ID NO. 24; SEQ ID NO. 38). These Dicer substrates are identical except for two LNA modifications on G3, which does not significantly affect the present discussion. The guide strand are G2 and G3, two 27 nucleotide long modified RNA strands. The passenger strands Ac4 and B7c are base-paired to the guide strands. B7c terminates at the 5' end in a blocker domain 5'OH—C3-mG*mG*mU-3' (SEQ ID NO. 48). Thus, as synthesized, the 5' terminus of C3 is terminated with a OH group. However, cellular kinases can rapidly phosphorylate this 5'-OH to create a terminal phosphate. This results in a proper binding target for Dicer's PAZ domain at the 3' terminus of the G2 and G3 strands. Dicer processing of both G2 Ac4 B7c (SEQ ID NO. 20; SEQ ID NO. 24; SEQ ID NO. 38) and G3 Ac4 B7c (SEQ ID NO. 22; SEQ ID NO. 24; SEQ ID NO. 38) are expected to be highly efficient. As shown in Example 11 and Example 12, both G2 Ac4 B7c (SEQ ID NO. 20; SEQ ID NO. 24; SEQ ID NO. 38) and G3 Ac4 B7c (SEQ ID NO. 22; SEQ ID NO. 24; SEQ ID NO. 38) have an RNAi activity resulting in a 50% or greater inhibition of protein production as detected by dual luciferase assays, as is shown in Example 11 and Example 12 and detectable Dicer products.

Example 3

Designing Polynucleotides for a Duplex

To design polynucleotides for the duplexes as shown in FIGS. 5A and 6A, the following protocols can be followed. As exemplified in FIGS. 5A and 6A which have the sequences B6b (C G A C G A A G A G C U C A U C C3 mG*mG*mU A A C mU A mG A mG A U mC) (SEQ ID NO. 17; SEQ ID NO. 18) and B7c (C3 mG*mG*mU A A C U mA G A mG A mU) (SEQ ID NO. 38), respectively, the design of the polyoligonucleotide is to be base paired to a complementary strand in which the GC content is optimally 30% to 55%. As known to those skilled in the art, a higher GC content can be selected to increase the melting temperature, however, if increasing the GC content is not possible, increasing the length of the polynucleotide, thereby increasing base pairing can also be used to increase the melting temperature. Additionally, the use of a Tm calculator as described to obtain the optimal melting temperature in the specific buffer used for dissolving the oligonucleotide, such as TE buffer (10 mM Tris, bring to pH 6.7 with HCl, 1 mM EDTA). OligoAnalyzer 2.0 (www.idtdna.com/analyzer/applications/oligoanalyzer/) can be used as the Tm calculator to obtain the desired melting temperature and can be adjusted with NaCl concentration if buffer stability is an issue for a particular oligonucleotide based on the formulation. Nupack (www.nupack.org) can be used to calculate the percent of base-paired complexes and base-pairing configurations given hypothetical oligonucleotide strands with specified sequences. For Nupack calculations, we optimize sequences and sequence lengths so that greater than 90% of strands form the desired duplex at 37 C at 100 nM strand concentrations. To further increase thermodynamic stability, 2'-O-methyl modification can be added to bases flanking the nick that are at least two nucleotides away from the Dicer cleavage site. Ideally, more than two consecutive 2'-O-methyl modifications can be used. For the polyoligonucleotides shown in FIG. 5A, the region to be selected for base pairing in sequence B6b (5'C G A C G A A G A G C U C A U C C3 <u>mG*mG*mUAACmUAmGAmGAUmC3'</u>) (SEQ ID NO. 17; SEQ ID NO. 18) are the underlined regions after the C3 linker, in order to create the 5' overhang with the sequence "5'C G A C G A A G A G C U C A U C.-3'" (SEQ ID NO. 46) To make the duplex structure exemplified in FIG. 6A with the sequence B7c (5' C3 mG*mG*mUAACUmAGAmGAmU3') (SEQ ID NO. 38), the region underlined from the 3' end of the C3 linker is selected for base-pairing to a complimentary strand and used for calculating the Tm range. The modified RNA can be order through companies that can specifically modify the oligonucleotides with phosphothioates and non-nucleic acid linkers (C3) such as Genelink (web page Genelink.com) and IdtDNA (see www page idtDNA at the date of filing of the application) which also have sites for calculating the Tm's for their specific oligonucleotide products. The complimentary sequence to the above regions described above for sequences shown in FIGS. 5A and 6A is also ordered for synthesizing the duplex (B6b and B7c). The oligonucleotides can also be further purified by reverse phase HPLC to ensure increased purity.

Example 4

Forming Assembly of Duplex and Testing of the Duplex

To form and test the formation of the duplexes shown in FIGS. 5A and 6A, the duplexes are formed by dissolving the three oligonucleotides as shown in Table 2 of the components G, pA, B6b, to form the G pA B6b (SEQ ID NO. 1; SEQ ID NO. 13; SEQ ID NO. 17; SEQ ID NO. 18) duplex with the 5' overhang (FIG. 5A) and dissolving the three oligonucleotides as shown in Table 2 of the components G2, Ac4, B7c (SEQ ID NO. 20; SEQ ID NO. 24; SEQ ID NO. 38), to form the G2 Ac4 B7c (SEQ ID NO. 20; SEQ ID NO. 24; SEQ ID NO. 38) duplex without the 5' overhang (FIG. 6A). The oligonucleotides to make the specific duplexes of FIGS. 5A and 6A are dissolved in TE buffer (pH 6.7), then added together to obtain a 1:1:1 ratio of the oligonucleotides (FIG. 5A, sequences G, pA, B6b to form the duplex G pA B6b (SEQ ID NO. 1; SEQ ID NO. 24; SEQ ID NO. 17; SEQ ID NO. 18); duplex of FIG. 6A, sequences G2, Ac4, and B7c to form the duplex G2 Ac4 B7c (SEQ ID NO. 20; SEQ ID NO. 24; SEQ ID NO. 38) to be mixed at a single strand concentrations of 50-200 microMolar, incubated at 95° C. for 2-5 minutes and subsequently cooled to 37° C. over a 45 to 60 minute period. The duplexes can also be stored for later use at −80° C.

Testing for the annealed assemblies as shown in FIGS. 5A and 6A can be performed by native polyacrylamide gel analysis in TE buffer, pH 6.7, due to the relatively small size of the duplex. The percent polyacrylamide can be adjusted to see the approximate size of the assembly as shown in Table 3 below:

TABLE 3

| % acrylamide | Size range for optimal resolution of duplex (bp) |
| --- | --- |
| 8 | 60-400 |
| 15 | 25-150 |
| 20 | 6-100 |

To test for the particular assemblies shown in FIGS. 5A and 6A by native polyacrylamide gel, the duplexes can be run along with each separate component and optionally, a low range DNA or RNA ladder with markers spanning the desired range as a relative reference in a buffer with standard reference dyes (e.g. xylene cyanol and bromophenol blue) to monitor the electrophoresis progress. For good resolution of duplex products, the polyacrylamide gel is run at 4 Celsius at a low voltage that maintains the temperature. After electrophoresis, the products can be visualized by staining in TE buffer containing a dye such as SybrGold capable of staining single stranded nucleic acids. Higher molecular products that are seen with the duplex can be further purified from expected duplex band through gel filtration or HPLC to ensure a purified duplex.

Example 5

Testing Stability of the Duplex (Tm)

To test the stability of the duplexes shown in FIGS. 5A and 6A, and to obtain accurate measure of the duplex Tm, melting curves for the duplexes can be performed using a UV spectrometer with a temperature controlled cell holder to measure the change of absorbance of the duplex at 260 nm (Specord Instruments). The analysis of a 100 µL polynucleotide solution can be performed in an ultra-micro cell sample holder that is temperature controlled against TE buffer or other buffer used to dissolve the oligonucleotides and is used as a blank solution. The final melting point measurement can be carried out in 'simultaneous' mode between the temperature range of 25° C. to 70° C. and at 260 nm, where the spectrum of DNA has a maximum at this wavelength. Measurements are taken in between the increments of 25° C. to 70° C., and for an accurate Tm measurement, data can be measured per 1° C. increase. The half-way point of the melting curve is indicative of the melting point of the duplex. As melting temperature is also dependent on the buffer, pH and salt concentrations, the melting temperature can vary depending on the buffer and is known to those skilled in the art.

Example 6

Structure Assembly of an Exemplary Molecular Construct that Comprises the Exonuclease Resistant Duplex An exemplary molecular construct was assembled and tested for processing as illustrated below.

To assemble an exemplary molecular construct comprising the exonuclease resistant duplex as shown in FIG. 14, first designing the duplex, testing the duplex for assembly, and testing the stability by Tm measurements is performed as described in Examples 3, 4, and 5 as shown above. As shown in FIG. 14, the construct comprises an annealed duplex where the B6b comprises the exonuclease resistant polynucleotide and is in a locked RNAi targeting domain (FIG. 14B). The duplex containing the sequence B6b, is directly linked to the 5' of the guide strand G. This linkage locks the RNAi targeting domain into a folded conformation that minimizes proper Dicer processing.

The individual strands composing G A1 B6b (SEQ ID NO. 1; SEQ ID NO. 3; SEQ ID NO. 17; SEQ ID NO. 18) (Table 2) were ordered from a commercial company, Thermo Scientific. For assembly, the strands composing G A1 B6b (SEQ ID NO. 1; SEQ ID NO. 3; SEQ ID NO. 17; SEQ ID NO. 18) were combined at 1 micromolar concentration in 1×PBS buffer (approximately 150 mM KCl with other components), heated to ~90 degrees Celsius, and allowed to cool to room temperature. During this process the strands self-assemble into either G A1 B6b (SEQ ID NO. 1; SEQ ID NO. 3; SEQ ID NO. 17; SEQ ID NO. 18). The resulting products are assessed by running the product through 8% non-denaturing polyacrylamide gel in 1×TBE buffer following standard practices in the art. Products are run alongside molecular weight markers, a DNA ladder to find specific bands that correspond to the Guide, A1, B6b, and the construct containing the duplex. In the conformation in which the construct comprising the duplex is formed, Dicer processing is minimized. If higher molecular weight products are seen, these higher molecular weight products can have spurious Dicer processing and RNAi activity. If desired, these products can be removed by filtering using HPLC, or filtration membranes with the appropriate molecular weight cutoff, or by extracting them using native polyacrylamide gel electrophoresis.

Example 7

Testing and Measuring of the Melting Temperature (Tm) of the Three Way Junction of an Activated RNAseH Based Construct Containing the Duplex Exemplary experimental procedures for testing/measuring the melting temperature of the three-way activation formed between the portions of the activation segment in constructs herein described having an RNAaseH based design.

Applicants first synthesized oligonucleotides, based on designing and testing polynucleotides for duplexes such as the duplexes schematically shown in FIGS. 5A and 6A as described above in the methods shown in Examples 3 to 5, above. The sequences for the guide strand passenger strand, displacement segment and activation segment respectively, were designed using standard methods for oligonucleotide synthesis well establish in the art. Then the synthesized oligonucleotides were then purified based on their expected lengths. The purified oligonucleotides were mixed together in an RNAase free buffer containing PBS. To allow proper annealing of the oligonucleotides, the mixture was heated to about 90° C. for 1 minutes and then cooled to a desired melting temperature of about 15° C. at the rate of 1° C. every 10 seconds. After annealing, RNAse H was added to the buffer and incubated according to manufacturer's instructions to allow cleavage of the construct by RNAse H. The cleavage products were then loaded onto a denaturing polyacrylamide gel (SDS-PAGE) following by electrophoresis to examine whether a proper DNA: RNA duplex of at least 5 consecutive base pairs have formed during annealing and whether the construct was cleaved at the expected RNAse H cleavage site.

To examine whether an activation junction formed among the segments (e.g. a three-way activation junction) is formed properly, Applicants attached pairs of fluorophore/quencher to nucleotides that are expected to form base pairs between opposing strands when the activation junction is properly formed, and examined whether significant quenching of the fluorescence signal can be observed at the minimum melting temperature using fluorescent microcopy. Additionally, the fluorophore/quencher pairs can be attached to pairs of neighboring nucleotides near the junction. Alternatively, in the above experiments, the fluorophore/quencher pairs can be replaced by pairs FRET acceptor/donor fluorophores, and examine significant FRET can be observed at the minimum melting temperature.

As a complimentary approach, Applicants used a standard set of procedures known to the art to establish the secondary structure of the construct.

First, Applicants used single stranded RNA endonucleases to digest the construct, and examined whether RNA portions of the segments that are expected to form double strands were protected from the cleavage by the endonuclease by formation of proper secondary structures.

Second, Applicants used single stranded DNA endonucleases to digest the construct, and examine whether the construct is protected from the cleavage by formation of the secondary structure of the duplex.

Third, Applicants tested whether the expected duplex regions of the junction is protected from RNA modifying and RNA cleaving chemical probes using 5' or 3' radionucleotide labeling or primer extension analysis.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

The above described experiments can also be performed according to commonly used experimental protocols and procedures, such as the one described in Keril J. Blight et al., Journal Of Virology, October 1997, vol 71, p. 7345-7352 herein incorporated by reference in its entirety.

Example 8

Testing and Measuring of the Melting Temperature (Tm) of the Construct-Locking Sensor Duplex Stem Containing the Duplex Domain Exemplary experimental procedures for testing/measuring the melting temperature (Tm) of the double-stranded duplex formed by the activation segment and the displacement segment are described below:

Applicants first synthesized oligonucleotides comprising sequences of designed for the guide strand, the passenger strand containing the sequences as shown in FIGS. 5A and 6A for the exonuclease resistant polynucleotide, activation segment, displacement segment and toehold segment respectively using standard methods for oligonucleotide synthesis well establish in the art. Design and testing of the exonuclease resistant polynucleotide for the duplex formation is performed as described in Examples 3 to 5, shown above. Then an internal fluorophore was attached to the 3' end of the displacement segment, and a quencher was attached to the 5' end of the protection segment opposing the base carrying the fluorophore. Alternative, the quencher can be attached to the 3' end of the displacement segment, while the internal fluorophore was attached to the 5' end of the protection segment opposing the base carrying the fluorophore. Also, a FRET donor/acceptor fluorophore pairs can be used instead of the fluorophore/quencher pair.

Then the oligonucleotides were purified based on their expected lengths and are mixed together in an RNAse free buffer containing PBS. To allow proper annealing of the oligonucleotides, the mixture was heated to about 90° C. for 1 minutes and then cooled to a desired melting temperature of about 25° C. at the rate of 1° C. every 10 seconds. During the annealing, the fluorescence signal was observed using a spectrofluorometer to examine whether a proper double-stranded duplex is formed between the protection segment and the displacement segment. At the melting temperature of 25° C., the fluorescence signal was quenched (if a FRET pair was used instead of the fluorophore/quencher pair, significant FRET signal between the FRET pairs is expected to be observed), which indicated that a double-stranded duplex has been formed properly between the protection segment and the displacement segment.

In addition, Applicants used the standard panel of enzymatic digest and chemical probe tests to further examine the melting temperature of the construct. Applicants used single strand endonuclease to digest the construct at or below the expected melting temperature (e.g. 25° C.) to examine whether the double-stranded portion of the displacement segment and the protection segment was protected from the endonuclease cleavage.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

Example 9

Testing and Measuring of the Strand Displacement of the Construct Comprising the Duplex Domain Exemplary experimental procedures for testing and measuring the strand displacement of the construct are described below:

Applicants first synthesized oligonucleotides comprising sequences of designed for activation segment, displacement segment and toehold segment (locking sensor), and a sequence for the exonuclease resistant polynucleotide for the duplex using standard methods for oligonucleotide synthesis well establish in the art. Passenger strands for exonuclease resistance are described and contain the sequences B6b (C G A C G A A G A G C U C A U C C3 mG*mG*mU A A C mU A mG A mG A U mC) (SEQ ID NO. 17; SEQ ID NO. 18) and B7c (C3 mG*mG*mU A A C U mA G A mG A mU) (SEQ ID NO. 38) for base pairing and are described in Example 2, Table 2, above. In order to obtain a functional and stable duplex as shown in the schematics of the duplexes shown in FIGS. 5A and 6A, the oligonucleotides designed for exonuclease resistance were designed, tested for assembly and stability as described in Examples 3 to 5 above. Then an internal fluorophore was attached to the terminus of the displacement segment that is further away from the toehold segment. A quencher was attached to the terminus of the activation segment that is further away from the toehold segment. Alternative, the internal fluorophore can be attached to the terminus of the protection segment that is further away from the toehold segment, while a quencher was attached to the terminus of the displacement segment that is further away from the toehold segment. Also, a FRET donor/acceptor fluorophore pairs can be used instead of the fluorophore/quencher pair. Also synthesized was a corresponding signal polynucleotide designed for the sensor domain described above.

Then the synthesized oligonucleotides were purified based on their expected lengths and were incubated with an equal amount of the signal polynucleotide under the operating condition (e.g. 1×PBS buffer) at the expected operating temperature (e.g. 37° C.).

The change in the fluorescent signal during the process of strand displacement was monitored and recorded using a spectrofluorometer. The recorded signal was then plotted as a function of time and the kinetic rate of the displacement reaction was determined from the plot.

To examine whether the attachment of the fluorophore/quencher introduces artifacts to the displacement kinetics and whether the entire protection segment is displaced during the process, the fluorophore/quencher pair was then attached to a different pair of nucleotides selected respectively from the protection segment and the displacement segment at positions closer to the toehold segment, and the above procedures were repeated.

Example 10

Process of Designing, Synthesis and Testing the Activity of a Signal Activated Construct Exemplary processes are described below for the designing, synthesis and testing the activity of a signal activated construct, which comprise a targeting domain configured for interfering a target intracellular process through RNAi.

To design a construct that comprises a duplex as exemplified in FIGS. 5A and 6A, Applicants started with the analysis of a RNA sequence that was to be targeted by RNA interference (RNAi), such as a target mRNA or a set of target mRNAs, and designed the duplex domain accordingly to the methods in Examples 3 TO 5, to contain the oligonucleotide for the duplex domain containing the blocker module and the 5' sensor extension. According to the RNA sequence to be targeted, applicants selected the sequences for the targeting domain of the construct that were known in the art.

For example, in the GA1 B6b (SEQ ID NO. 1; SEQ ID NO. 3; SEQ ID NO. 17; SEQ ID NO. 18) construct shown in FIG. 14A, applicants started with the Dicer substrate 27/29 mers duplex with the 29 nucleotide guide strand sequence 5'-mC mU mU G C G U C U G A G G G A U C U C U A G U U A C C U U-3' (SEQ ID NO. 47) (m, methylation).

Applicants introduce a nick in the passenger 27 nucleotide passenger strand complementary to this guide strand, so that the passenger strand is divided into a 13 nucleotide and a 14 nucleotide piece.

The signal sequence selected was long enough so that there are very few spurious matches to possible RNA transcripts from the organism's genome. For using in human cells, the signal polynucleotide can have a minimum length of about 14 nucleotides, but in this case a longer signal was used. Further, the signal polynucleotide was designed to have at least 4 nucleotides that complementarily bind to the toehold segment. In total, the signal nucleotide selected for the use in human cells can be at least 18 nucleotides in length.

In the construct shown in FIG. 14A, the applicants chose to have a 16 bp sensor extension. Thus, corresponding signal polynucleotide base pairs at a site that is 22 nucleotides.

The 5' of this signal polynucleotide was complementary to the 3' sensor toehold illustrated in FIG. 14B and the rest was complementary to the signal binding side of the 16 bp 5' sensor extension stem.

At this point, the sensor domain was fully specified. The applicants then connected the signal binding strand (left side of the 16 bp sensor stem) to the 3' passenger strand and the displaced segment to the 5' piece of the passenger strand. This allows the sensor domain to lock the targeting domain into the folded, inactive conformation.

In order to ensure sufficient geometric slack to allow formation of the construct, a 2 nucleotide spacer was introduced on the signal binding side and a C3 linker was introduced between the displaced strand and the passenger strand (B6b) (Table 2).

The C3 linker also serves to prevent the 5' sensor overhang from interfering with Dicer processing of the ACTIVE RNAi targeting domain.

To further prevent the possible processive exonucleolytic degradation of the 5' passenger strand by XRN1, two 2'-O-methyl base modifications and 2 phosphorothioate backbone modifications were placed immediately to the 3' side of the C3 linker (shown in strand B6b of (FIG. 14)

At this stage all segments in the sensor domain (i.e. the protection segment, displacement segment, activation segment and the toehold segment) have been specified. Using the above algorithm, Applicants designed the sensor domains for the every possible 21-nucleotides sequence of the chosen signal polynucleotide. Then Applicants examined each candidate design by running the sequences through an RNA secondary structure calculation code to examine the predictions for secondary structure conformation and stability. Based on the result, applicants chose one or more candidate designs with the best stability among the ones tested, and the least complicated secondary structure in the toehold, and added chemical modifications to regulate base pair stability.

In particular, for increased stability, Applicants applied added 2'-O-methyl modifications to the entire signal binding side of the sensor duplex. Applicants also changed the 4 bases at the 5' terminus of the guide strand to 2'-O-methyl, and applicants changed some bases in the 3' piece of the passenger strand (the one with 14 base-pairs to the guide strand) to 2'-O-methyl. In addition, an inverted dT base was added to the 3' terminus of the toehold to prevent Dicer binding.

Example 11

Confirmation of RNAai Processing of the Guide Strand in Exemplary Duplexes by Luciferase Analysis In order to test processing of the guide strand from a duplex comprising variations of a exonuclease resistant polynucleotides, the duplexes G pA pB (SEQ ID NO. 1; SEQ ID NO. 13; SEQ ID NO. 14), G pA B6b (SEQ ID NO. 1; SEQ ID NO. 13; SEQ ID NO. 17; SEQ ID NO. 18), 4 G pA B6-R (SEQ ID NO. 1; SEQ ID NO. 13; SEQ ID NO. 19), G2 Ac4 B7c (SEQ ID NO. 20; SEQ ID NO. 24; SEQ ID NO. 25; SEQ ID NO. 26), G2 Ac4 B7 (SEQ ID NO. 20; SEQ ID NO. 24; SEQ ID NO. 38), G2 Ac4, B10 (SEQ ID NO. 20; SEQ ID NO. 24; SEQ ID NO. 27; SEQ ID NO. 28), G2 Ac4 B11 (SEQ ID NO. 20; SEQ ID NO. 24; SEQ ID NO. 29; SEQ ID NO. 30), G2 Ac4 B12 (SEQ ID NO. 20; SEQ ID NO. 24; SEQ ID NO. 31; SEQ ID NO. 32), were tested in which Applicants performed dual Luciferase assays whose results are illustrated in FIGS. 8A and 8B, using the luciferase protocol described above. As described above, designing of the duplexes for assembly, and stability are described in the methods of Examples 3 to 5 and the components of the duplexes are shown in Table 2 in Example 2.

In particular FIGS. 8A and 8B shows functioning of the different implementations of the duplexes in dual luciferase assays, whose methods are described above in "Transfections for Luciferase analyses." In these dual Luciferase assays the ratio of *Renilla* Luciferase to Firefly Luciferase luminosity is compared to a negative control. A value of 1.0 signifies undetectable RNAi activity. A value of 0.0 constitutes perfect RNAi activity, meaning there is zero activity from the *Renilla* luciferase target of RNAi knockdown.

To test the design of the exemplary duplexes for exonuclease resistance, controls were run alongside of the exemplary duplexes. As shown in FIG. 8A, Exemplar G pA pB (SEQ ID NO. 1; SEQ ID NO. 13; SEQ ID NO. 14) (duplex diagramed in FIG. 7) whose sequences are described above in Tables 1 and 2, represents a typical 27-mer siRNA Dicer substrate siRNA where binding of Dicer's PAZ domain (Dicer entry) is blocked at the 5' end of the guide strand (the top of the duplex shown in FIG. 7 marked by the asterisks) by the presence of an inverted dT base at the 3' end of pA strand. Dicer therefore enters from the 2-nucleotide, 3' overhang of the guide strand.

As shown in FIG. 8A, the G pA pB (SEQ ID NO. 1; SEQ ID NO. 13; SEQ ID NO. 14) control duplex, featuring sequences of the passenger controls strands pA and pB mediates an RNAi activity resulting in a 50% or greater inhibition of protein production as detected by dual luciferase assays To test knockdown abilities of a polynucleotide with a 5' overhang that does not comprise a blocker module, a Guide strand with an additional 16-mer RNA extension was synthesized to was generate B6-R (shown in FIG. 5B, and sequence described in Table 1), and used to create the duplex G pA B6-R (SEQ ID NO. 1; SEQ ID NO. 13; SEQ ID NO. 19), which was shown to reduce RNAi activity. For example the signal of luciferase increases more than two fold at the 1.0 and 0.2 nM concentrations. The 5' extension inhibits Dicer entry; however, it was postulated that exonucleases such as XRN1 can remove the overhang over time, producing a better Dicer substrate. However, XRN1 is known to be processive and have duplex unwinding capabilities. Therefore, once XRN1 loads onto the 5' extension of B6-R, it could continue to degrade the B6-R (SEQ ID NO. 19) strand past the first paired base of the duplex on a subset of G pA B6-R (SEQ ID NO. 1; SEQ ID NO. 13; SEQ ID NO. 19) molecules, reducing the amount of optimal Dicer substrate configuration available as represented by G pA pB (SEQ ID NO. 1; SEQ ID NO. 13; SEQ ID NO. 14). To circumvent this particular effect, addition of the blocking module to the B6-R strand, described in Table 2, was postulated to improve RNAi-mediated knockdown, which uses the blocker module (FIG. 12), and is exactly what is observed in FIG. 8A for the construct G pA B6b (SEQ ID NO. 1; SEQ ID NO. 13; SEQ ID NO. 17; SEQ ID NO. 18), which comprises the duplex with the oligonucleotide sequence B6b, shown in Table 2 above).

It was further theorized by Applicants that if nuclease degradation is responsible for the removal of the 5' overhang, then using nuclease-resistant bases would inhibit its removal thereby reducing Dicer processing and concomitant dual luciferase activity. FIGS. 8B and 9A shows dual luciferase assays of exemplars testing this hypothesis that are part of the same data set shown in FIG. 8A, using a different version of the guide strand (G2) and A strand (A4c) (sequences described in (Table 2) that forms a 25 base pair duplex, rather than the 27 base pair duplex formed in exemplars containing the original G strand (FIG. 8B). All of the B strands tested contain the blocker module in the series (Blocker sequences shown in Table 2). G2 Ac4 B7c (SEQ ID NO. 20; SEQ ID NO. 24; SEQ ID NO. 38) is the baseline construct analogous G pA pB (SEQ ID NO. 1; SEQ ID NO. 13; SEQ ID NO. 14), which lacks the 5' extension while G2 Ac4 B7 (SEQ ID NO. 20; SEQ ID NO. 24; SEQ ID NO. 25; SEQ ID NO. 26) (FIG. 4A) is analogous to G pA pB6 (SEQ ID NO. 1; SEQ ID NO. 13; SEQ ID NO. 14) (FIG. 5A) where the B strand 5' extensions are made entirely of standard RNA bases. Both G2 Ac4 B7c (SEQ ID NO. 20; SEQ ID NO. 24; SEQ ID NO. 38) (FIG. 6A) and G2 Ac4 B7 (SEQ ID NO. 20; SEQ ID NO. 24; SEQ ID NO. 25; SEQ ID NO. 26) (FIG. 4A) show similar RNAi-mediated activity to their counterparts in FIG. 8A. However, use of a B strand where the entire 5' extension of the B strand is phosphorothioated including both sides of the C3 linker (B10), reduces the dual luciferase knockdown in G2 Ac4 B10 (SEQ ID NO. 20; SEQ ID NO. 24; SEQ ID NO. 27; SEQ ID NO. 28) (FIGS. 4B and 8B). Removal of phosphorthiorates flanking the C3 and between the next three bases of the extension partially restores RNAi activity (G2 Ac4 B11 (SEQ ID NO. 20; SEQ ID NO. 24; SEQ ID NO. 29; SEQ ID NO. 30) (FIGS. 4C and 8B). Further removal of the phosphorothioate linkages between the next 9 bases of the extension of the B strand (B12) restores even more of the dual luciferase activity in G2 Ac4 B12 (SEQ ID NO. 20; SEQ ID NO. 24; SEQ ID NO. 31; SEQ ID NO. 32) (FIGS. 4D and 8B). This data shows that the greater the number of nuclease resistant bases in the 5' extension of the B strand, the greater the reduction of dual luciferase activity. This correlates with a reduction in the amount of Dicer product, as seen in the Northern analysis of FIG. 10; compare lanes 6-8 with lanes 4 and 5. The B10, B11 and B12 strands show a ladder of products between the starting 28 nt size (filled arrow) and the 'stopped' product (open arrow) consistent with nuclease degradation products of varying lengths) (FIG. 11 lanes 6-8) which are not seen with the B7 strand (lane 5). The B7, B10, B11 and B12 strands differ in that the degree of phosphorothioation of the 5' extension connected to the blocker module. An increase in RNAi activity is seen in a linear effect from concentrations of 5.00 and 1.00 nM as shown in FIG. 8B using the B10, B11, and B12 polynucleotides.

B7 has an unmodified 5' extension with only RNA base and standard phosphodiester backbone connections. The B10 diftogether, these results support that the blocker module can effectively stop exonuclease degradation of the 5' polynucleotide extension.

Example 12

Confirmation of Accessibility and Processing of the Duplex Domain in HCT116 Cells To confirm the accessibility of the individual segments of the exemplary molecular constructs, Applicants transfected the constructs tested in Example 11 into HCT116 cells, extracted RNA, and performed a Northern blot with probes specific to the different segments of the duplex to observe presence as well as processing as described above in the methods for Northern blot analysis.

The probes used for the Northern Blot are described in Table 4

TABLE 4

| | | | | | |
|---|---|---|---|---|---|
| Probes for Northern Blotting | | | | | |
| Name | Abbreviation | No. of nt | Description | Sequence | Notes |
| senB LNA probe | senB LNA | 14 | A DNA probe for detection of B6b, B6-R, B7, B7c, B10, B11, B12 strands on Northern blots | G A +T C +T C T A G T +T A C C (SEQ ID NO. 40) | Before use, the 5' end of this oligonucleootide is phosphorylated to add a phosphate incorporating a radioactive P32. |
| 544 probe | 544 | 21 | A DNA probe for detection of G, G2, G3 strands on Northern blots | G G T A A C T A G A G A T C C C T C A G A (SEQ ID NO. 41) | Before use, the 5' end of this oligonucleootide is phosphorylated to add a phosphate incorporating a radioactive P32. |

+ indicates LNA base fers from B7 in that the 5' extension on B10 has all phosphorothioate backbone connections. B10 also has a 5' terminal hexaethyleneglycol and the connections flanking the C3 linker in the blocker module. In B11, the phosphorothioate bonds present around the blocker module and flanking the C3 linker are changed back to phosphodiester connections. In B12, most of the phosphorothioate backbone connections in the 5' extension have been removed, leaving only three such connections at the 5' terminus. An incidental difference between B7, B10, B11, and B12 is that the 5' extension in B7 has an extra adenine immediately to the 5' of the blocker module. For these duplexes (FIG. 3), the 5' extension in B7 is most easily processed by 5' exoribonucleases among the tested duplexes, while the extension in B10 is expected to be more exonuclease resistant. A difference between B10 and all others is that cleavage of the backbone linking the C3 in the blocker module to the 5' extension would leave a phosphorothioate 5' terminus.

Figure 11:
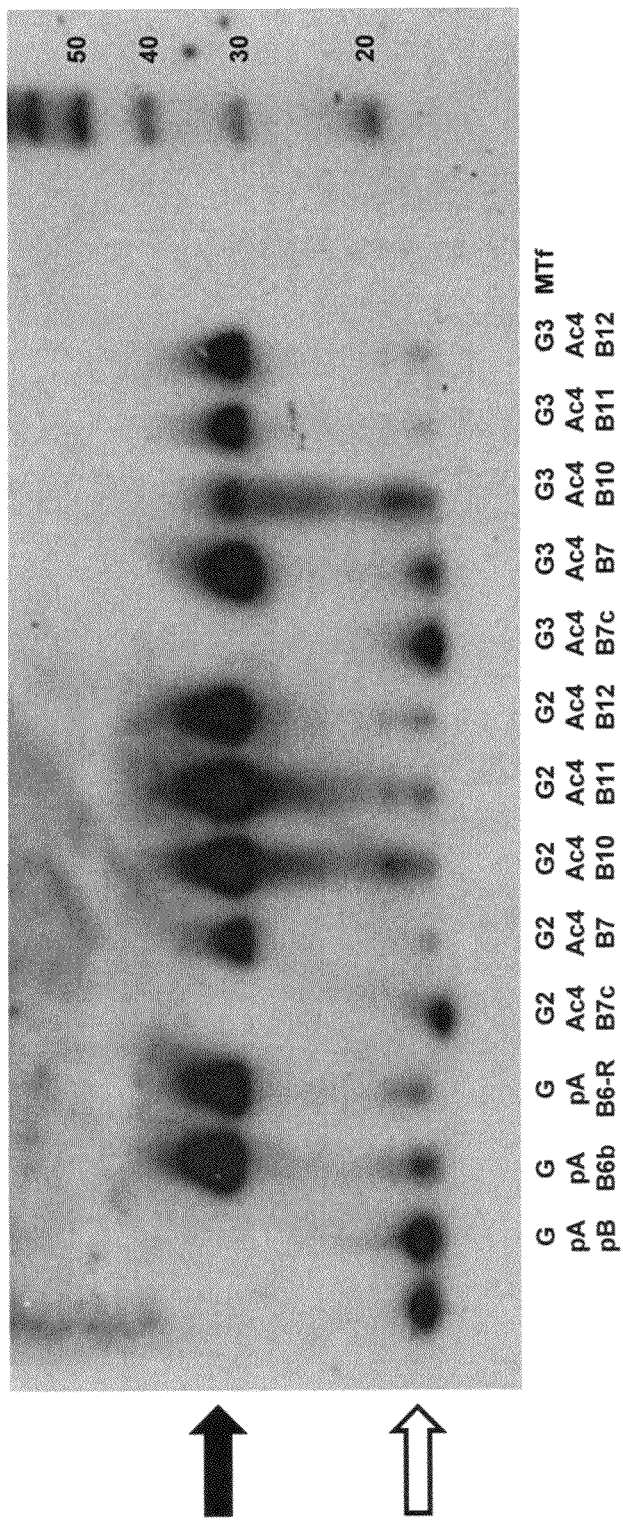
FIG. 11 shows a representation of a Northern blot performed with a probe for the 3' end of the B strands (the portion of the B strand which is duplexed with the 5' end of the guide strand) of the exemplary constructs comprising an exonuclease resistant duplex polynucleotide also tested in FIG. 10. In particular, in the illustration of FIG. 11, Lane 1, contains an irrelevant construct; lane 2, G pA pB (SEQ ID NO. 1; SEQ ID NO. 13; SEQ ID NO. 14); lane 3, G pA B6b (SEQ ID NO. 1; SEQ ID NO. 13; SEQ ID NO. 17; SEQ ID NO. 18); lane 4 G pA B6-R (SEQ ID NO. 1; SEQ ID NO. 13; SEQ ID NO. 19); lane 5, G2 Ac4 B7c (SEQ ID NO. 20; SEQ ID NO. 24; SEQ ID NO. 38); lane 6, G2 Ac4 B7 SEQ ID NO. 20; SEQ ID NO. 24; SEQ ID NO. 25; SEQ ID NO. 26); lane 7, G2 Ac4 B10 (SEQ ID NO. 20; SEQ ID NO. 24; SEQ ID NO. 28; SEQ ID NO. 29); lane 8, G2 Ac4 B11 (SEQ ID NO. 20; SEQ ID NO. 24; SEQ ID NO. 29; SEQ ID NO. 30); lane 9, G2 Ac4 B12 (SEQ ID NO. 20; SEQ ID NO. 24; SEQ ID NO. 31; SEQ ID NO. 32); lane 10, G3 Ac4 B7c (SEQ ID NO. 22; SEQ ID NO. 24; SEQ ID NO. 38); lane 11, G3 Ac4 B7 (SEQ ID NO. 22; SEQ ID NO. 24; SEQ ID NO. 25; SEQ ID NO. 26); lane 12, G3 Ac4 B10 (SEQ ID NO. 22; SEQ ID NO. 24; SEQ ID NO. 27; SEQ ID NO. 28); lane 13, G3 Ac4 B11 (SEQ ID NO. 22; SEQ ID NO. 24; SEQ ID NO. 29; SEQ ID NO. 30); lane 14, G2 Ac4 B12 (SEQ ID NO. 22; SEQ ID NO. 24; SEQ ID NO. 31; SEQ ID NO. 32); lane Mtf, Mock transfected (carrier only); Lane M, RNA size markers, number of nucleotides is indicated.

FIG. 9 compares the dual luciferase activity of the G2 series (FIG. 9A) with the same series using the guide strand, G3, containing LNA bases (FIG. 9B) with very similar results. The Northern results for the G3 series (FIGS. 10 and 11, lanes 9-13) also parallel those of the G2 series. Taken As shown in FIGS. 10 and 11, the specific duplexes used in the luciferase assays of FIGS. 8 and 9 are tested on a Northern blot. In particular, in the Northern blot of FIG. 10, Probe (oligo 544) hybridizes to intact guide strand G (29 nucleotides) seen in lanes 1-14 and the approximately 21 nucleotide Dicer product, indicated by the open arrow, is visible in lanes 2, 3, 5, 6, 9, 10 and 11.

As shown, Lanes 2-4 of the Northern analysis of the guide strand in FIG. 10, show that the degree of dual luciferase knockdown of these duplexes is correlated with the amount of conversion of the guide strand from 27 nucleotides to the approximately 21 nucleotides products expected by Dicer processing (clear arrow). Moreover, if the blocking module stops exonuclease degradation of the 5' extension more effectively, then it is possible to observe the remaining fragment by Northern analysis, which would be approximately the same size as pB if exonuclease degradation stops at the base of duplex stem. FIG. 11 shows the same Northern as in FIG. 10 in which the duplex strand is instead hybridized with the Sen B probe that is complementary to the 3' end of all the B strands. Hybridization to intact B strands is indicated by the filled arrow. While G pA B6-R (SEQ ID NO. 1; SEQ ID NO. 13; SEQ ID NO. 19) (lane 4) does show a fragment corresponding exonuclease stopping at the base of the duplex (compared with G pA pB (SEQ ID NO. 1; SEQ ID NO. 13; SEQ ID NO. 14) in lane 2), there is considerably more of the 'stopped' B strand product (open arrow) in lane 3 with G pA B6b (SEQ ID NO. 1; SEQ ID NO. 13; SEQ ID NO. 17; SEQ ID NO. 18) exemplar that contains the blocking module.

Lanes 2 to 4 of the Northern blots of FIGS. 10 and 11 correlates to the results of the luciferase assay showing knockdown of these duplexes (FIG. 8A). The reduction in the amount of Dicer product, can be seen in the Northern analysis of FIG. 10. Comparison of lanes 6-8 with lanes 4 and 5 correlates with the knock down of RNAi activity as seen in the luciferase activity assays whose results are shown in FIG. 8B. The B10, B11 and B12 strands show a ladder of products between the starting 28 nt size (filled arrow) and the 'stopped' product (open arrow) consistent with nuclease degradation products of varying lengths) (FIG. 11 lanes 6-8) which are not seen with the B7 strand (lane 5). The Northern results for the G3 series (FIGS. 10 and 11, lanes 9-13) also parallel those of the G2 series. Taken together, these results support that the blocker module can effectively stop exonuclease degradation of the 5' polynucleotide extension.

Example 13

Exemplary Constructs Comprising Exonuclease Resistant Polynucleotide

In order to create a construct for the delivery of molecular cargo, an exemplary construct comprising an exonuclease resistant polynucleotide is described.

The development of therapeutic proteins that has presented a valuable method to treat diseases is limited by low efficiency of traditional delivery methods. Recently, several methods using a cell penetrating peptide (CPP) as vehicles to deliver biologically active, full-length proteins into living cells can be useful for delivering peptides for therapeutic treatment.

As previously described, a construct is designed, assembled and tested for stability for the duplex domain comprising the exonuclease resistant polynucleotide as described in Examples 3 to 5 and in Examples 6-10. The construct is tested for assembly and stability for the intention of delivering cargo in vitro in which the construct is not degradable by exonucleases in order to properly deliver cargo for the cell.

To deliver a molecular cargo as shown in the schematic of FIG. 18, a construct that comprises a duplex that further comprises an exonuclease resistant polynucleotide as described in Examples 3 to 5 is designed, assembled, and tested for thermostability is performed as described in Examples 3 to 5. For the guide strand that is bound by complementarity to the passenger strand that comprises the exonuclease resistant polynucleotide, the 3' end of the passenger strand can be covalently attached to CPP which are short peptides to facilitate cellular uptake of various molecular cargo (from nanosize particles to small chemical molecules and large fragments of DNA). For example, a CPP can be attached to the 3' end of the pA strand as shown in FIG. 5A, in which the passenger strand is bound by complementary Watson-crick base pairing to the Guide strand. The functions of the CPPs are to deliver the cargo into cells, a process that commonly occurs through endocytosis with the cargo delivered to the endosomes of living mammalian cells. The CPP can be attached to the 3' end of the corresponding Guide strand by chemical modification such as crosslinking, and denaturation of proteins before crosslinking to the 3' region of the guide strand. Synthetic peptides containing a nuclear localization signal (NLS) can be used as CPP and bound to the oligonucleotide so that the resulting oligonucleotide-NLS complex can be recognized as a nuclear import substrate by specific intracellular receptor proteins Once the CPP is attached to the passenger strand, similar tests for stability and assembly with the modified guide strand is performed according to the methods in Examples 3 to 5, to ensure that the CPP does not affect the assembly of the complex. Furthermore, polyacrylamide gel analysis can be done to test that the delivery cargo is still intact with the construct.

CPPs mediate entry into cells by endocytosis with the cargo. Once the complex with the attached CPP is within the cytoplasm, the assembled vehicle as shown in FIG. 18A can be recognized by the XRN1 exonuclease which cleaves the 5' end of the passenger strand that is adjacent to the attached CPP FIG. 18B. Once the XRN1 cleaves to the 5' end of the linker, degradation is stopped and the CPP is delivered (FIG. 18C). The Dicer substrate is then released for processing by Dicer (FIG. 18D).

Testing for efficient CPP-mediated cellular delivery can be performed in the case of an siRNA cargo intended for post-transcriptional gene silencing of mRNA targets using the dual luciferase assays already described. In the case of a cargo that regulates transcriptional gene activation or silencing a specific nuclear localization signal can be attached to the CPP to localize the cargo to the target cellular compartment, to affect transcription. Quantitative RT-PCR can be used to assess the effect on transcription levels and Western blotting the effect on protein levels of the target entity.

The examples set forth above are provided to give those of ordinary skill in the art a complete disclosure and description of how to make and use the embodiments of the constructs, complexes, sensors, arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the paper copy of the sequence listing submitted herewith and the corresponding computer readable form are both incorporated herein by reference in their entireties.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

Wu, H. et al., "*Properties of cloned and expressed human RNase H1*", The Journal of Biological Chemistry, Vol. 274, pp. 28270 (1999).

Zamaratski, E. et al., "*A critical survey of the structure function of the antisense oligo/RNA heteroduplex as substrate for RNase H*", Journal of Biochemical and Biophysical Methods, Vol. 48, pp. 189 (2001).

Cazenave, C. et al., "*Characterization and subcellular localization of ribonuclease H activities from Xenopus laevis oocytes*", The Journal of biological chemistry, Vol. 269, pp. 25185 (1994).

Nowotny, M. et al., "*Crystal structures of RNase H bound to an RNA/DNA hybrid: substrate specificity and metal-dependent catalysis*", Cell, Vol. 121, pp. 1005 (2005).

Song, J. J. et al., "*The crystal structure of the Argonaute2 PAZ domain reveals an RNA binding motif in RNAi effector complexes*", Nature Structural Biology, Vol. 10, pp. 1026 (2003).

Ma, J. B. et al., "*Structural basis for overhang-specific small interfering RNA recognition by the PAZ domain*", Nature, Vol. 429, pp. 318 (2004).

Yan, K. S. et al., "*Structure and conserved RNA binding of the PAZ domain*", Nature, Vol. 426, pp. 468 (2003).

Lingel, A. et al., "*Structure and nucleic-acid binding of the Drosophila Argonaute 2 PAZ domain*", Nature, Vol. 426, pp. 465 (2003).

Behlke, M. A. et al., "*Chemical modification of siRNAs for in vivo use*", Oligonucleotides, Vol. 18, pp. 305 (2008).

Rose, S. D. et al., "*Functional polarity is introduced by Dicer processing of short substrate RNAs*", Nucleic Acids Research, Vol. 33, pp. 4140 (2005).

Tomari, Y., et al., "*A Protein Sensor for siRNA Asymmetry*", Science, Vol. 306, pp. 1377, (2004).

Susan M. Freier and Karl-Heinz Altman, The ups and downs of nucleic acid duplex stability: structure-stability studies on chemically-modified DNA:RNA duplexes, Nucleic Acids Research, 1997, Vol. 25, No. 22 4429-4443

Nucleic Acids Research, 1998, Vol. 26, No. 9, 2224-2229

Nucleic Acids Research, 2005, Vol. 33, No. 16, 5082-5093

564-574 Nucleic Acids Research, 2006, Vol. 34, No. 2

Sequence-specific recognition of double helical RNA and RNA. DNA by triple helix formation, PNAS May 1, 1993 vol. 90 no. 9 3806-3810

Burge S, Parkinson G N, Hazel P, Todd A K, Neidle S (2006). "Quadruplex DNA: sequence, topology and structure". NAR 34 (19): 5402-5415. doi:10.1093/nar/gkl655

J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. J Comput Chem, 32, 170-173, 2011.

R. M. Dirks, J. S. Bois, J. M. Schaeffer, E. Winfree, and N. A. Pierce. (2007) Thermodynamic analysis of interacting nucleic acid strands. SIAM Rev, 49, 65-88.

R. M. Dirks and N. A. Pierce. (2003) A partition function algorithm for nucleic acid secondary structure including pseudoknots. J Comput Chem, 24, 1664-1677.

R. M. Dirks and N. A. Pierce. (2004) An algorithm for computing nucleic acid base-pairing probabilities including pseudoknots. J Comput Chem, 25, 1295-1304.

J. N. Zadeh, B. R. Wolfe, N. A. Pierce. Nucleic acid sequence design via efficient ensemble defect optimization. J Comput Chem, 32, 439-452, 2011.

M. Zuker. Mfold web server for nucleic acid folding and hybridization prediction. Nucleic Acids Res. 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major. RNAML: A standard syntax for exchanging RNA information. RNA 8 (6), 707-717, 2002.

M. Zuker & A. B. Jacobson. Using Reliability Information to Annotate RNA Secondary Structures. RNA 4, 669-679, 1998. [Abstract][Preprint] Note: Explains color annotation of secondary structure.

N. R. Markham & M. Zuker. UNAFold: Software for Nucleic Acid Folding and Hybridization. In Data, Sequence Analysis, and Evolution, J. Keith, ed., Bioinformatics: Volume 2, Chapter 1, pp 3-31, Humana Press Inc., 2008.

M. Zuker, D. H. Mathews & D. H. Turner. Algorithms and Thermodynamics for RNA Secondary Structure Prediction: A Practical Guide In RNA Biochemistry and Biotechnology, 11-43, J. Barciszewski and B. F. C. Clark, eds., NATO ASI Series, Kluwer Academic Publishers, Dordrecht, NL, 1999.

M. Zuker. Prediction of RNA Secondary Structure by Energy Minimization. In Computer Analysis of Sequence Data A. M. Griffin and H. G. Griffin eds. Methods in Molecular Biology, Humana Press Inc., 267-294, 1994.

J. A. Jaeger, D. H. Turner & M. Zuker. Predicting Optimal and Suboptimal Secondary Structure for RNA. In Molecular Evolution: Computer Analysis of Protein and Nucleic Acid Sequences, R. F. Doolittle ed. Methods in Enzymology 183, 281-306, 1990.

M. Zuker. On Finding All Suboptimal Foldings of an RNA Molecule. Science 244, 48-52, 1989.

D. H. Mathews, J. Sabina, M. Zuker & D. H. Turner. Expanded Sequence Dependence of Thermodynamic Parameters Improves Prediction of RNA Secondary Structure J. Mol. Biol. 288, 911-940, 1999.

E. Walter, D. H. Turner, J. Kim, M. H. Lyttle, P. Müller, D. H. Mathews & M. Zuker. Coaxial stacking of helixes enhances binding of oligoribonucleotides and improves predictions of RNA folding. Proc. Natl. Acad. Sci. USA 91, 9218-9222, 1994.

D. H. Mathews, W. N. Moss and D. H. Turner Folding and Finding RNA Secondary Structure in Cold Spring Harb Perspect Biol. 2010.

D. H. Mathews, D. H. Turner & M. Zuker. RNA Secondary Structure Prediction. In Current Protocols in Nucleic Acid Chemistry S. Beaucage, D. E. Bergstrom, G. D. Glick, and R. A. Jones eds., John Wiley & Sons, New York, 11.2.1-11.2.10, 2007.

D. H. Mathews, S. J. Schroeder, D. H. Turner & M. Zuker. Predicting RNA Secondary Structure. In The RNA World, R. F. Gesteland, T. R. Cech and J. F. Atkins eds., 3rd edition, Cold Spring Harbor Laboratory Press, Cold Spring Harbor, N.Y., Chapter 22, 2006.

D. H. Mathews & M. Zuker. Predictive Methods Using RNA Sequences. In Bioinformatics: A Practical Guide to the Analysis of Genes and Proteins, A. Baxevanis and F. Ouellette eds., 3rd edition, John Wiley & Sons, New York, Chapter 7, 2005.

D. H. Mathews, M. D. Disney, J. L. Childs, S. J. Schroeder, M. Zuker & D. H. Turner. Incorporating chemical modification constraints into a dynamic programming algorithm for prediction of RNA secondary structure. Proc. Natl. Acad. Sci. USA 101 (19), 7287-7292, 2004.

M. Zuker & D. Sankoff. RNA Secondary Structures and their Prediction. Bull. Mathematical Biology 46, 591-621, 1984.

M. Zuker & P. Stiegler. Optimal computer folding of large RNA sequences using thermodynamics and auxiliary information. Nucleic Acids Res. 9, 133-148, 1981.

J.-M. Rouillard, M. Zuker & E. Gulari. OligoArray 2.0: design of oligonucleotide probes for DNA microarrays using a thermodynamic approach. Nucleic Acids Res. 31 (12), 3057-3062, 2003.

J.-M. Rouillard, C. J. Herbert & M. Zuker. OligoArray: Genome-scale oligonucleotide design for microarrays. Bioinformatics 18 (3), 486-487, 2002.

RNA secondary structure prediction by centroids in a Boltzmann weighted ensemble, Ye Ding, Chi Yu Chan, and Charles E. Lawrence, RNA 2005. 11: 1157-1166

Oligonucleotide synthesis: methods and applications, Volume 288 of Methods in molecular biology, Piet Herdewijn, Humana Press, 2005

Principles of Nucleic Acid Structure, Stephen Neidle, 2008 Elsevier Inc, ISBN: 978-0-12-369507-9

RNA Interference in Mammalian Cells by Chemically-Modified RNA, Biochemistry 2003, 42, 7967-7975

Modified Nucleosides: in Biochemistry, Biotechnology and Medicine, Piet Herdewijn (Editor), Wiley-VCH, 2008 in-Biao Ma, Keqiong Ye & Dinshaw J. Patel Structural basis for overhang specific small interfering RNA recognition by the PAZ domain, Nature, 429, 318 (2004)

Nature Reviews Drug Discovery 8, 129-138 (February 2009) |doi:10.1038/nrd2742, Knocking down barriers: advances in siRNA delivery Simeoni, F. "Insight into the mechanism of the peptide based gene delivery system MPG: implications for delivery of siRNA into mammalian cells." Nucleic acids research 31.11 (2003):2717.

Liu, Z., Winters, M., Holodniy, M. and Dai, H. (2007), siRNA Delivery into Human T Cells and Primary Cells with Carbon-Nanotube Transporters. Angewandte Chemie, 119: 2069-2073. doi: 10.1002/ange.200604295

Aptamer mediated siRNA delivery Nucl. Acids Res. 34(10): e73 doi:10.1093/nar/gk1388

Dynamic PolyConjugates for targeted in vivo delivery of siRNA to hepatocytes PNAS 2007 104 (32) 12982-12987

Bioconjugate Chem., 2007, 18 (5), pp 1391-1396, DOI: 10.1021/bc060367e

T Cell-Specific siRNA Delivery Suppresses HIV-1 Infection in Humanized Mice, Cell, Volume 134, Issue 4, 22 Aug. 2008, Pages 577-586

A universal RNAi-based logic evaluator that operates in mammalian cells, Nature Biotechnology 25, 795-801 (2007)

Molecular Therapy (2010) 18 4, 796-802. doi:10.1038/mt.2009.321, RNA (2010), 16:1275-1284

Molecular Therapy (2006) 13, 494-505

Hong-Wei Wang, Cameron Noland, Bunpote Siridechadilok, David W Taylor, Enbo Ma, Karin Felderer, Jennifer A Doudna & Eva Nogales Structural insights into RNA processing by the human RISC-loading complex Nature Structural & Molecular Biology 16, 1148-1153 (2009)

Matsukura, M., Shinozuka, K., Zon, G., Mitsuya, H., Reitz, M., Cohen, J. S. & Broder, S. Phosphorothioate analogs of oligodeoxynucleotides: inhibitors of replication and cytopathic effects of human immunodeficiency virus. *Proceedings of the National Academy of Sciences* 84, 7706-7710 (1987).

Collingwood, M., Collingwood, S., Rose, L., Huang, C., Hillier, M., Amarzguioui, M., Wiiger, H., Soifer, J., Rossi, M. & Behlke. Chemical Modification Patterns Compatible with High Potency Dicer-Substrate Small Interfering RNAs. *Oligonucleotides* 18, 187-200 (2008).

Lennox, K. A., Owczarzy, R., Thomas, D. M., Walder, J. A. & Behlke, M. A. Improved Performance of Anti-miRNA Oligonucleotides Using a Novel Non-Nucleotide Modifier. *Mol Ther Nucleic Acids* 2, e117, doi:10.1038/mtna.2013.46 (2013).

Bramsen, J. B., Laursen, M. B., Nielsen, A. F., Hansen, T. B., Bus, C., Langkjær, N., Babu, B. R., Højland, T., Abramov, M., Van Aerschot, A., Odadzic, D., Smicius, R., Haas, J., Andree, C., Barman, J., Wenska, M., Srivastava, P., Zhou, C., Honcharenko, D., Hess, S., Müller, E., Bobkov, G. V., Mikhailov, S, N., Fava, E., Meyer, T. F., Chattopadhyaya, J., Zerial, M., Engels, J. W., Herdewijn, P., Wengel, J. & Kjems, J. A large-scale chemical modification screen identifies design rules to generate siRNAs with high activity, high stability and low toxicity. *Nucleic Acids Research* 37, 2867-2881, doi:10.1093/nar/gkp106 (2009).

Mathy, N., Bénard, L., Pellegrini, O., Daou, R., Wen, T. & Condon, C. 52-to-32 Exoribonuclease Activity in Bacteria: Role of RNase J1 in rRNA Maturation and 52 Stability of mRNA. *Cell* 129, 681-692 (2007).

Yang, X.-c., Sullivan, K. D., Marzluff, W. F. & Dominski, Z. Studies of the 5' Exonuclease and Endonuclease Activities of CPSF-73 in Histone Pre-mRNA Processing. *Molecular and Cellular Biology* 29, 31-42, doi:10.1128/mcb.00776-08 (2009).

Efthymiou, T. C., Peel, B., Huynh, V. & Desaulniers, J.-P. Evaluation of siRNAs that contain internal variable-length spacer linkages. *Bioorganic & Medicinal Chemistry Letters* 22, 5590-5594, doi:http://dx.doi.org/10.1016/j.bmcl.2012.07.006 (2012).

Zhou, J., Swiderski, P., Li, H., Zhang, J., Neff, C. P., Akkina, R. & Rossi, J. J. Selection, characterization and application of new RNA HIV gp 120 aptamers for facile delivery of Dicer substrate siRNAs into HIV infected cells. *Nucleic Acids Research* 37, 3094-3109, doi:10.1093/nar/gkp185 (2009).

---

SEQUENCE LISTING

```
<160> NUMBER OF SEQ ID NOS: 51

<210> SEQ ID NO 1
<211> LENGTH: 29
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: gm

<400> SEQUENCE: 1
cuugcgucug agggaucucu aguuaccuu                                       29

<210> SEQ ID NO 2
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 2
ucugagggau cucuaguuac c                                               21

<210> SEQ ID NO 3
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(36)
<223> OTHER INFORMATION: ribonucleotides
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: misc_feature
<222> LOCATION: (17)..(17)
<223> OTHER INFORMATION: 2'-O-methyl adenosine
```

```
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (20)..(20)
<223> OTHER INFORMATION: 2'-O-methyl adenosine
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (24)..(24)
<223> OTHER INFORMATION: cm
<220> FEATURE:
<221> NAME/KEY: modified_base
<222> LOCATION: (25)..(26)
<223> OTHER INFORMATION: um
<220> FEATURE:
<221> NAME/KEY: modified_base
<222> LOCATION: (27)..(27)
<223> OTHER INFORMATION: cm
<220> FEATURE:
<221> NAME/KEY: modified_base
<222> LOCATION: (28)..(28)
<223> OTHER INFORMATION: gm
<220> FEATURE:
<221> NAME/KEY: modified_base
<222> LOCATION: (29)..(29)
<223> OTHER INFORMATION: um
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: gm
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (33)..(33)
<223> OTHER INFORMATION: um
<220> FEATURE:
<221> NAME/KEY: modified_base
<222> LOCATION: (34)..(34)
<223> OTHER INFORMATION: gm
<220> FEATURE:
<221> NAME/KEY: modified_base
<222> LOCATION: (35)..(36)
<223> OTHER INFORMATION: um
<220> FEATURE:
<221> NAME/KEY: misc_feature
<222> LOCATION: (37)..(37)
<223> OTHER INFORMATION: inverted deoxyribonucleotide

<400> SEQUENCE: 3
ccucagacgc aagcugauga gcucuucguc gcuguut                              37

<210> SEQ ID NO 4
```

```
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (12)..(13)
<223> OTHER INFORMATION: phosphorothioate backbone
<220> FEATURE:
<221> NAME/KEY: misc_feature
<222> LOCATION: (12)..(12)
<223> OTHER INFORMATION: 2'-O-methyl adenosine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (13)..(13)
<223> OTHER INFORMATION: 18S linker to 5' end of SEQ ID NO: 5

<400> SEQUENCE: 4
ccucagacgc aag                                                      13

<210> SEQ ID NO 5
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..()
<223> OTHER INFORMATION: 18S linker to 3' end of SEQ ID NO: 4

<400> SEQUENCE: 5
gaugagcucu ucgucgcugu cuc                                           23

<210> SEQ ID NO 6
<211> LENGTH: 12
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: 18S linker to 5' end of SEQ ID NO: 7
<220> FEATURE:
<221> NAME/KEY: modified_base
<222> LOCATION: (12)..(12)
<223> OTHER INFORMATION: gm

<400> SEQUENCE: 6
cccucagacg cg                                                       12

<210> SEQ ID NO 7
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
```

```
<222> LOCATION: (1)..(1)
<223> OTHER INFORMATION: 18S linker to 3' end of SEQ ID NO: 6
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: um
<220> FEATURE:
<221> NAME/KEY: misc_feature
<222> LOCATION: (14)..(14)
<223> OTHER INFORMATION: 9S linker to 5' end of SEQ ID NO: 8

<400> SEQUENCE: 7
gaugagcuuc gucg                                                    14

<210> SEQ ID NO 8
<211> LENGTH: 8
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 9S linker to 3' end of SEQ ID NO: 7
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(6)
<223> OTHER INFORMATION: cm
<220> FEATURE:
<221> NAME/KEY: misc_feature
<222> LOCATION: (8)..(8)
<223> OTHER INFORMATION: 9S linker attached to inverted deoxynucleotide
      T
<220> FEATURE:
<221> NAME/KEY: modified_base
<222> LOCATION: (8)..(8)
<223> OTHER INFORMATION: cm

<400> SEQUENCE: 8 gucuccgc                                                            8

<210> SEQ ID NO 9
<211> LENGTH: 56
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (29)..(30)
<223> OTHER INFORMATION: n = any nucleotide
```

```
<220> FEATURE:
<221> NAME/KEY: misc_feature
<222> LOCATION: (37)..(38)
<223> OTHER INFORMATION: n = any nucleotide
<220> FEATURE:
<221> NAME/KEY: misc_feature
<222> LOCATION: (47)..(48)
<223> OTHER INFORMATION: n = any nucleotide

<400> SEQUENCE: 9
cugaugagcu cuucgucgcu gucuccgcnn gaugagnncu ucgucgnngu cuccgc      56

<210> SEQ ID NO 10
<211> LENGTH: 12
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: gm
<220> FEATURE:
<221> NAME/KEY: misc_feature
<222> LOCATION: (12)..(12)
<223> OTHER INFORMATION: 9S linker to 5' end of SEQ ID NO: 11

<400> SEQUENCE: 10
cccucagacg cg                                                      12

<210> SEQ ID NO 11
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 9S linker to 3' end of SEQ ID NO: 10
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
```

```
<223> OTHER INFORMATION: cm
<220> FEATURE:
<221> NAME/KEY: modified_base
<222> LOCATION: (8)..(9)
<223> OTHER INFORMATION: um
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: 9S linker to 5' end of SEQ ID NO: 12
<220> FEATURE:
<221> NAME/KEY: modified_base
<222> LOCATION: (14)..(14)
<223> OTHER INFORMATION: gm

<400> SEQUENCE: 11
gaugagcuuc gucg                                                        14

<210> SEQ ID NO 12
<211> LENGTH: 8
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 9S linker to 3' end of SEQ ID NO: 11
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: misc_feature
<222> LOCATION: (8)..(8)
<223> OTHER INFORMATION: 9S linker attached to inverted deoxynucleotide
      T
<220> FEATURE:
<221> NAME/KEY: modified_base
<222> LOCATION: (8)..(8)
<223> OTHER INFORMATION: cm
```

```
<400> SEQUENCE: 12 gucuccgc                                                                    8

<210> SEQ ID NO 13
<211> LENGTH: 14
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(13)
<223> OTHER INFORMATION: ribonucleotides
<220> FEATURE:
<221> NAME/KEY: misc_feature
<222> LOCATION: (14)..(14)
<223> OTHER INFORMATION: inverted deoxyribonucleotide

<400> SEQUENCE: 13
ccucagacgc aagt                                                            14

<210> SEQ ID NO 14
<211> LENGTH: 14
<212> TYPE: RNA
<213> ORGANISM: Artificial sequence
<220> FEATURE:
<223> OTHER INFORMATION: Synthetic polynucleotide

<400> SEQUENCE: 14
gguaacuaga gauc                                                            14

<210> SEQ ID NO 15
<211> LENGTH: 39
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(38)
<223> OTHER INFORMATION: ribonucleotides
<220> FEATURE:
<221> NAME/KEY: misc_feature
<222> LOCATION: (1)..(5)
<223> OTHER INFORMATION: 2'-O-methyl adenosine
<220> FEATURE:
<221> NAME/KEY: misc_feature
<222> LOCATION: (34)..(38)
<223> OTHER INFORMATION: 2'-O-methyl adenosine
<220> FEATURE:
<221> NAME/KEY: misc_feature
<222> LOCATION: (39)..(39)
<223> OTHER INFORMATION: inverted deoxyribonucleotide

<400> SEQUENCE: 15
aaaaagcgga gacagcgacg aagagcucau cagaaaaat                                 39

<210> SEQ ID NO 16
<211> LENGTH: 35
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(34)
<223> OTHER INFORMATION: ribonucleotides
<220> FEATURE:
<221> NAME/KEY: misc_feature
<222> LOCATION: (1)..(5)
<223> OTHER INFORMATION: 2'-O-methyl adenosine
```

```
<220> FEATURE:
<221> NAME/KEY: misc_feature
<222> LOCATION: (34)..(38)
<223> OTHER INFORMATION: 2'-O-methyl adenosine
<220> FEATURE:
<221> NAME/KEY: misc_feature
<222> LOCATION: (35)..(35)
<223> OTHER INFORMATION: inverted deoxyribonucleotide

<400> SEQUENCE: 16
aaaaagcgga gacaacgacg aagcucauca aaaat                                    35

<210> SEQ ID NO 17
<211> LENGTH: 16
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (16)..(16)
<223> OTHER INFORMATION: C3 linker attached to 5' end of SEQ ID NO: 18

<400> SEQUENCE: 17
cgacgaagag cucauc                                                         16

<210> SEQ ID NO 18
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker attached to 3' end of SEQ ID NO: 17
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (14)..(14)
<223> OTHER INFORMATION: cm

<400> SEQUENCE: 18
gguaacuaga gauc                                                           14

<210> SEQ ID NO 19
```

```
<211> LENGTH: 30
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (27)..(27)
<223> OTHER INFORMATION: gm
<220> FEATURE:
<221> NAME/KEY: modified_base
<222> LOCATION: (30)..(30)
<223> OTHER INFORMATION: cm

<400> SEQUENCE: 19
cgacgaagag cucaucggua acuagagauc                                          30

<210> SEQ ID NO 20
<211> LENGTH: 27
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm

<400> SEQUENCE: 20
cgcgucugag ggaucucuag uuaccuu                                             27

<210> SEQ ID NO 21
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 21
ucugagggau cucuaguuac c                                                   21

<210> SEQ ID NO 22
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (22)..(22)
<223> OTHER INFORMATION: locked nucleic acid

<400> SEQUENCE: 22
cgcgucugag ggaucucuag utaccuu                                             27
```

```
<210> SEQ ID NO 23
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 23
ucugagggau cucuaguuac c                                              21

<210> SEQ ID NO 24
<211> LENGTH: 12
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: gm

<400> SEQUENCE: 24
cccucagacg cg                                                        12

<210> SEQ ID NO 25
<211> LENGTH: 15
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: C3 linker attached to 5' end of SEQ ID NO: 26

<400> SEQUENCE: 25
cgacgaagcu cauca                                                     15

<210> SEQ ID NO 26
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (1)..(1)
<223> OTHER INFORMATION: C3 linker attached to 3' end of SEQ ID NO: 25
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: 2'-O-methyl adenosine
<220> FEATURE:
```

```
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 26
gguaacuaga gau                                                          13

<210> SEQ ID NO 27
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(14)
<223> OTHER INFORMATION: phosphorothioate backbone
<220> FEATURE:
<221> NAME/KEY: misc_feature
<222> LOCATION: (14)..(14)
<223> OTHER INFORMATION: C3 linker attached to 5' end of SEQ ID NO: 28

<400> SEQUENCE: 27
cgacgaagcu cauc                                                         14

<210> SEQ ID NO 28
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker attached to 3' end of SEQ ID NO: 27
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 28
gguaacuaga gau                                                          13

<210> SEQ ID NO 29
<211> LENGTH: 14
<212> TYPE: RNA
<213> ORGANISM: Artificial sequence
<220> FEATURE:
<223> OTHER INFORMATION: Synthetic polynucleotide
```

```
<220> FEATURE:
<221> NAME/KEY: misc_feature
<222> LOCATION: (1)..(1)
<223> OTHER INFORMATION: C3 linker attached to 3' end of SEQ ID NO: 28
<220> FEATURE:
<221> NAME/KEY: misc_feature
<222> LOCATION: (1)..(12)
<223> OTHER INFORMATION: phosphorothioate backbone

<400> SEQUENCE: 29
cgacgaagcu cauc                                                        14

<210> SEQ ID NO 30
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker attached to 3' end of SEQ ID NO: 29
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 30
gguaacuaga gau                                                         13

<210> SEQ ID NO 31
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (14)..(14)
<223> OTHER INFORMATION: C3 linker attached to 5' end of SEQ ID NO: 32

<400> SEQUENCE: 31
cgacgaagcu cauc                                                        14

<210> SEQ ID NO 32
<211> LENGTH: 13
<212> TYPE: RNA
<213> ORGANISM: Artificial sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker attached to 3' end of SEQ ID NO: 31
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: misc_feature
<222> LOCATION: (4)..(4)
<223> OTHER INFORMATION: 2'-O-methyl adenosine
<220> FEATURE:
<221> NAME/KEY: misc_feature
<222> LOCATION: (8)..(8)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 32
gguaacuaga gau                                                        13

<210> SEQ ID NO 33
<211> LENGTH: 15
<212> TYPE: RNA
<213> ORGANISM: Artificial sequence
<220> FEATURE:
<223> OTHER INFORMATION: Synthetic polynucleotide

<400> SEQUENCE: 33
cgacgaagcu cauca                                                      15

<210> SEQ ID NO 34
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (10)..(10)
<223> OTHER INFORMATION: um

<400> SEQUENCE: 34
aacuagagau cccucagacg cg                                              22

<210> SEQ ID NO 35
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
```

```
<222> LOCATION: (1)..(14)
<223> OTHER INFORMATION: phosphorothioate backbone
<220> FEATURE:
<221> NAME/KEY: misc_feature
<222> LOCATION: (1)..(1)
<223> OTHER INFORMATION: (PEG) hexaethyleneglycol linker attached to 5'
      end of SEQ ID NO: 36
<220> FEATURE:
<221> NAME/KEY: misc_feature
<222> LOCATION: (14)..(14)
<223> OTHER INFORMATION: C3 linker attached to 5' end of SEQ ID NO: 48

<400> SEQUENCE: 35
cgacgaagcu cauc                                                       14

<210> SEQ ID NO 36
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(12)
<223> OTHER INFORMATION: phosphorothioate backbone
<220> FEATURE:
<221> NAME/KEY: misc_feature
<222> LOCATION: (1)..(1)
<223> OTHER INFORMATION: (PEG) hexaethyleneglycol linker attached to 5'
      end of SEQ ID NO: 36
<220> FEATURE:
<221> NAME/KEY: misc_feature
<222> LOCATION: (14)..(14)
<223> OTHER INFORMATION: C3 linker attached to 5' end of SEQ ID NO: 48

<400> SEQUENCE: 36
cgacgaagcu cauc                                                       14

<210> SEQ ID NO 37
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 37
ugagggaucu cuaguuaccu u                                               21

<210> SEQ ID NO 38
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker attached to 5' end of SEQ ID NO: 38
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
```

<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 38
gguaacuaga gau                    13

<210> SEQ ID NO 39
<211> LENGTH: 16
<212> TYPE: RNA
<213> ORGANISM: Artificial sequence
<220> FEATURE:
<223> OTHER INFORMATION: Synthetic polynucleotide

<400> SEQUENCE: 39
cgacgaagag cucauc                 16

<210> SEQ ID NO 40
<211> LENGTH: 14
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 40
gatctctagt tacc                   14

<210> SEQ ID NO 41
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 41
ggtaactaga gatccctcag a           21

<210> SEQ ID NO 42
<211> LENGTH: 13
<212> TYPE: RNA
<213> ORGANISM: Artificial sequence
<220> FEATURE:
<223> OTHER INFORMATION: Synthetic polynucleotide

<400> SEQUENCE: 42
ccucagacgc aag                    13

<210> SEQ ID NO 43
<211> LENGTH: 14
<212> TYPE: RNA
<213> ORGANISM: Artificial sequence

```
<220> FEATURE:
<223> OTHER INFORMATION: Synthetic polynucleotide
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (14)..(14)
<223> OTHER INFORMATION: cm

<400> SEQUENCE: 43
gguaacuaga gauc                                                        14

<210> SEQ ID NO 44
<211> LENGTH: 8
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: gm

<400> SEQUENCE: 44 cuugcguc                                                                8

<210> SEQ ID NO 45
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 45
ugagggaucu cuaguuaccu u                                                21

<210> SEQ ID NO 46
<211> LENGTH: 16
<212> TYPE: RNA
<213> ORGANISM: Artificial sequence
<220> FEATURE:
<223> OTHER INFORMATION: Synthetic polynucleotide

<400> SEQUENCE: 46
cgacgaagag cucauc                                                      16

<210> SEQ ID NO 47
<211> LENGTH: 29
<212> TYPE: RNA
<213> ORGANISM: Artificial sequence
<220> FEATURE:
<223> OTHER INFORMATION: Synthetic polynucleotide
<220> FEATURE:
```

```
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um

<400> SEQUENCE: 47
cuugcgucug agggaucucu aguuaccuu                                              29

<210> SEQ ID NO 48
<211> LENGTH: 3
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (1)..(1)
<223> OTHER INFORMATION: C3 linker attached to 3' end of SEQ ID NO: 35
     & 36
<220> FEATURE:
<221> NAME/KEY: modified_base
<222> LOCATION: (3)..(3)
<223> OTHER INFORMATION: um

<400> SEQUENCE: 48 ggu                                                                           3

<210> SEQ ID NO 49
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: X is attached to the 5' end of SEQ ID NO: 49;
     X is a non-nucleic acid polymer and in particular can be an alkyl,
     polyether or polypeptide polymer, more particularly a C2-C6 alkyl,
     a 2xPEG to 3xPEG or a two amino acid polypeptide
<220> FEATURE:
<221> NAME/KEY: misc_feature
<222> LOCATION: (1)..(1)
<223> OTHER INFORMATION: n is attached to X which, in turn, is attached
     to the 5' end of SEQ ID NO: 49; n can be 0 or 1, wherein each A1
     and the base sequence are lined to X through a phosphodiester
     linkage
<220> FEATURE:
<221> NAME/KEY: misc_feature
<222> LOCATION: (1)..(1)
<223> OTHER INFORMATION: A1 is attached to n which, in turn, is attached
     to X which, in turn, is attached to the 5' end of SEQ ID NO: 49;
     A1 is an oligonucleotide comprising any number of modified/
     unmodified nucleotides and can comprise 2 to 10 Kb or more
     possibly up to 100 bases
<220> FEATURE:
<221> NAME/KEY: misc_feature
<222> LOCATION: (1)..(3)
<223> OTHER INFORMATION: n = any nucleotide
<220> FEATURE:
<221> NAME/KEY: misc_feature
<222> LOCATION: (3)..(3)
<223> OTHER INFORMATION: A2 is attached to the 3' end of SEQ ID NO: 49;
     A2 is any number of modified/unmodified bases; A2 can be up to 100
     modified/unmodified bases and from 2-67 modified/unmodified bases

<400> SEQUENCE: 49
```

```
nnn                                                                    3
```

```
<210> SEQ ID NO 50
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: X is attached to the 5' end of SEQ ID NO: 50;
      X is a non-nucleic acid polymer and in particular can be an alkyl,
      polyether or polypeptide polymer, more particularly a C2-C6 alkyl,
      a 2xPEG to 3xPEG or a two amino acid polypeptide
<220> FEATURE:
<221> NAME/KEY: misc_feature
<222> LOCATION: (1)..(3)
<223> OTHER INFORMATION: n = any nucleotide
<220> FEATURE:
<221> NAME/KEY: misc_feature
<222> LOCATION: (3)..(3)
<223> OTHER INFORMATION: A2 is attached to the 3' end of SEQ ID NO: 50;
      A2 is any number of modified/unmodified bases; A2 can be up to 100
      modified/unmodified bases and from 2-67 modified/unmodified bases

<400> SEQUENCE: 50
```

```
nnn                                                                    3
```

```
<210> SEQ ID NO 51
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: X is attached to the 5' end of SEQ ID NO: 51;
      X is a non-nucleic acid polymer and in particular can be an alkyl,
      polyether or polypeptide polymer, more particularly a C2-C6 alkyl,
      a 2xPEG to 3xPEG or a two amino acid polypeptide
<220> FEATURE:
<221> NAME/KEY: misc_feature
<222> LOCATION: (1)..(3)
<223> OTHER INFORMATION: n = any nucleotide
<220> FEATURE:
<221> NAME/KEY: misc_feature
<222> LOCATION: (1)..(1)
<223> OTHER INFORMATION: A1 is attached to  X which, in turn, is
      attached to the 5' end of SEQ ID NO: 51; A1 is an oligonucleotide
      comprising any number of modified/unmodified nucleotides and can
      comprise 2 to 10 Kb or more possibly up to 100 bases
<220> FEATURE:
<221> NAME/KEY: misc_feature
<222> LOCATION: (3)..(3)
<223> OTHER INFORMATION: A2 is attached to the 3' end of SEQ ID NO: 51;
      A2 is any number of modified/unmodified bases; A2 can be up to 100
      modified/unmodified bases and from 2-67 modified/unmodified bases

<400> SEQUENCE: 51
```

```
nnn                                                                    3
```

What is claimed is:

1. An exonuclease resistant duplex polynucleotide comprising a duplex RNA having a length of about 19 to about 30 bp and comprising a guide strand complementary bound to a passenger strand, each of the guide strand and passenger strand having a 5' end and a 3' end, the duplex RNA being in a configuration allowing processing of the guide strand by dicer and/or an argonaute enzyme, the passenger strand comprising an exonuclease resistant polynucleotide having a 5' end and a 3' end and comprising a blocker domain having a non-nucleic acid polymer segment and a phosphorothioate segment, wherein the non-nucleic acid polymer segment comprises a non-nucleic acid linear polymer having a first end and a second end, the non-nucleic acid linear polymer having two to six residues linked one to another by a residue-to-residue bond, with an end-to-end distance for the non-nucleic acid linear polymer in a fully extended conformation of up to about 1 nm, the non-nucleic acid linear polymer having a persistence length up to about 0.5 nm;

the phosphorothioate segment comprises one to five nucleotides linked by phosphorothioate linkages to form a phosphorothioate sequence having a 5' and a 3' end;

the phosphorothioate segment attaches the first end of the non-nucleic acid polymer segment at the 5' end of phosphorothioate sequence through a phosphodiester linkage; and the second end of the non-nucleic acid polymer segment is presented at the 5' end of the exonuclease resistant polynucleotide, the exonuclease resistant polynucleotide in a configuration in which the second end of the non-nucleic acid polymer is presented at the 5' end of the passenger strand.

2. The exonuclease resistant duplex polynucleotide of claim 1, wherein the passenger strand is nicked to allow the exonuclease resistant polynucleotide to have at least one configuration allowing processing of the guide strand by dicer and/or an argonaute enzyme and at least one configuration minimizes processing of the guide strand by dicer and/or an argonaute enzyme.

3. The exonuclease resistant duplex polynucleotide of claim 1, wherein the exonuclease resistant polynucleotide comprises a 5' overhang region having modified nucleotides and/or phosphodiester linkages to control the degradation rate of the exonuclease resistant polynucleotide.

4. The exonuclease resistant duplex polynucleotide of claim 3, wherein the 5' overhang region has modified nucleotides and/or phosphodiester linkages in a pattern associated with a set degradation rate of the exonuclease resistant polynucleotide.

5. A molecular construct comprising the exonuclease resistant duplex polynucleotide of claim 1, attached to at least one additional moiety, the molecular construct having at least one configuration of the exonuclease resistant molecular construct in which the 5' passenger strand of the exonuclease resistant duplex polynucleotide is presented for binding to an exonuclease.

6. A method to provide the exonuclease resistant duplex polynucleotide of claim 1, the method comprising providing a duplex polynucleotide comprising an exonuclease resistant polynucleotide of claim 1 wherein, the duplex polynucleotide has a length of about 19 to about 30 bp and comprising a guide strand complementary bound to a passenger strand, each of the guide strand and passenger strand having a 5' end and a 3' end, the duplex RNA being in a configuration allowing processing of the guide strand by dicer and/or an argonaute enzyme and wherein the providing is performed to have the second end of non-nucleic acid polymer presented at the 5' end of the passenger strand.

7. A method to provide a molecular construct having an exonuclease resistant moiety, the method comprising, providing an exonuclease resistant duplex polynucleotide of claim 1 attaching at least one additional moiety in at least one configuration of the exonuclease resistant molecular construct in which the 5' passenger strand of the exonuclease resistant duplex polynucleotide is presented for binding to an exonuclease.

8. A composition comprising one or more exonuclease resistant duplex polynucleotides of claim 1 together with a suitable vehicle.

9. A composition comprising an exonuclease resistant molecular construct of claim 5, together with a suitable vehicle.

10. The exonuclease resistant duplex polynucleotide of claim 1, wherein the end-to-end distance for the non-nucleic acid linear polymer in a fully extended conformation is about 0.4 nm, about 0.5 nm, about 0.65, about 0.8 nm, or about 0.9 nm.

11. The exonuclease resistant duplex polynucleotide of claim 1, wherein the persistence length of the non-nucleic acid linear polymer is about 0.38 nm.

12. The exonuclease resistant duplex polynucleotide of claim 1, wherein the non-nucleic acid linear polymer comprises a substituted or unsubstituted alkyl chain, a polyether or a polypeptide.

13. The exonuclease resistant duplex polynucleotide of claim 1, wherein the one to five nucleotides of the phosphorothioate segment are modified nucleotides.

14. The exonuclease resistant duplex polynucleotide of claim 1, wherein the phosphorothioate segment comprises two to three nucleotides.

15. The exonuclease resistant duplex polynucleotide of claim 1, further comprising a 5' overhang domain having a 5' end and a 3' end, the 5' overhang domain being presented on the 5' end of the exonuclease resistant polynucleotide, the 5' overhang domain attached to the second end of the non-nucleic acid polymer segment.

16. The exonuclease resistant duplex polynucleotide of claim 15, wherein the overhang domain comprises one or more modified nucleotide and/or phosphorothioeter linkages.

17. The exonuclease resistant duplex polynucleotide of claim 15, wherein the one or more modified nucleotide and/or phosphorothioeter linkages are comprised in the 5' overhang domain in a pattern associated with a set degradation rate of the 5' overhang domain.

18. The exonuclease resistant duplex polynucleotide of claim 1, wherein the exonuclease resistant polynucleotide has formula

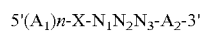    (I)

wherein $A_1$ is an oligonucleotide comprising 2 to 10 Kb modified or unmodified nucleotides;

$N_1$ $N_2$ and $N_3$ are independently any modified or unmodified nucleotides, each of $N_1$ and $N_3$ being linked to $N_2$ through a phosphorothioate linkage, $X_1$ is a non-nucleic acid polymer linked to each of A1 and N1 through a phosphodiester linkage n, can be 0 or 1, and moiety 5'X-$N_1$-$N_2$-$N_3$-3' is the blocker domain is formed by in which X is the non-nucleic acid polymer segment and moiety 5'$N_1$-$N_2$-$N_3$3' is the phosphorothioate segment, and A2 is a sequence of the passenger domain upstream to the blocker domain.

19. The exonuclease resistant duplex polynucleotide of claim 18, wherein n=1 and A1 is a 5' overhang region having modified nucleotides and/or phosphodiester linkages to control the degradation rate of the exonuclease resistant polynucleotide.

20. The exonuclease resistant duplex polynucleotide of claim 19, wherein $A_1$ is an oligonucleotide up to 100 nucleotides.

21. The exonuclease resistant duplex polynucleotide of claim 18, wherein N1, N2, N3 are independently 2' O-methyl, 2'F, 2'NH4 or an LNA residue.

22. The exonuclease resistant duplex polynucleotide of claim 21, wherein $N_1$, $N_2$ and $N_3$ are 2-O-methyl nucleotides.

23. The exonuclease resistant duplex polynucleotide of claim 21, wherein at least one of $N_1$, N2 and $N_3$ is 2'-F, or LNA.

24. The exonuclease resistant duplex polynucleotide of claim 18, wherein $X_1$ is an alkyl, polyether or polypeptide polymer.

25. The exonuclease resistant duplex polynucleotide of claim 24, wherein $X_1$ is a C2-C6 alkyl, a Poly Ethylene Glycol, or a two amino acid polypeptide.

26. The exonuclease resistant duplex polynucleotide of claim 24, wherein $X_1$ is a $C_3$ alkyl chain, a tri-ethylene glycol, or a hexa-ethylene glycol.

\* \* \* \* \*